United States Patent [19]

Basu et al.

[11] Patent Number: 5,880,161
[45] Date of Patent: Mar. 9, 1999

[54] THERAPEUTIC POLYAMINES

[75] Inventors: Hirak Subhra Basu, Pacifica; Burt Feuerstein, San Francisco, both of Calif.; Keijiro Samejima, Kokubunji, Japan; Laurence Marton, Fitchburg, Wis.

[73] Assignee: The United States of America as represented by the Department of Health and Human Services, Washington, D.C.

[21] Appl. No.: 690,648

[22] Filed: Jul. 29, 1996

Related U.S. Application Data

[62] Division of Ser. No. 147,527, Nov. 5, 1993, Pat. No. 5,541,230.

[51] Int. Cl.⁶ .......................... A61K 31/14; A61K 33/24; A61K 31/13
[52] U.S. Cl. .......................... 514/642; 424/649; 514/674
[58] Field of Search .................... 514/642, 674; 424/649

[56] References Cited

U.S. PATENT DOCUMENTS

| | | | |
|---|---|---|---|
| 4,987,253 | 1/1991 | Bergeron | 562/623 |
| 5,091,576 | 2/1992 | Bergeron | 564/367 |
| 5,342,945 | 8/1994 | Bergeron | 544/296 |

OTHER PUBLICATIONS

Basu et al., *Biochem. J.* 244:243–46 (1987).
Basu et al., *Cancer Res.* 49:5591–97 (1989).
Basu et al., *Biochem. J.* 269:329–34 (1990).
Deen et al., *Int'l J. Rad. Oncol. Biol. Phys.* 5:1663–67 (1979).
Basu et al., *Int'l J. Cancer* 48:873–78 (1991).
Feurstein et al., *J. Cell. Biochem.* 46:37–47 (1991).
Ghoda et al., *Mol. Pharmacol.* 42:302–06 (1992).
Basu et al., *Cancer Res.* 50:3137–40 (1990).
Basu et al., *Cancer. Res.* 49:5591–97 (1989).
Basu et al., *Cancer Res.* 53:3948–55 (1993).
Basu et al., *Biochem. J.* 282:723–27 (1992).
Pegg et al., *Biochem. J.*, vol. 267(2), pp. 331–38 (1990).
Pegg et al., *Biochem. J.*, vol. 269(3), p. 839 (1990).

*Primary Examiner*—Jerome D. Goldberg
*Attorney, Agent, or Firm*—Klarquist Sparkman Campbell Leigh & Whinston, LLP

[57] ABSTRACT

Therapeutic polyamines useful as a cancer chemotherapeutic agents, including molecules having a formula $R_1$—NH—$(CH_2)_w$—NH—$(CH_2)_x$—NH—$(CH_2)_y$—NH—$(CH_2)_z$—NH—R, wherein $R_1$ and $R_2$ are hydrocarbon chains having 1 to 5 carbons and w, x, y and z are integer of 1 to 10, are disclosed. One such molecule is $N^1$, $N^{19}$-bis(ethylamino)-5,10,15-triazanonadecane, which is longer than spermine. This preferred compound may be used alone or in combination with other therapeutic agents, such as 1,3-bis(2-chloroethyl)-1-nitrosourea or cis-Pt.

11 Claims, 39 Drawing Sheets

FIG. 1
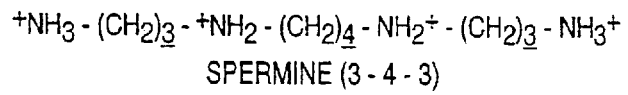
SPERMINE (3 - 4 - 3)
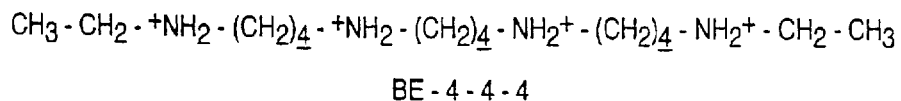
BE - 4 - 4 - 4
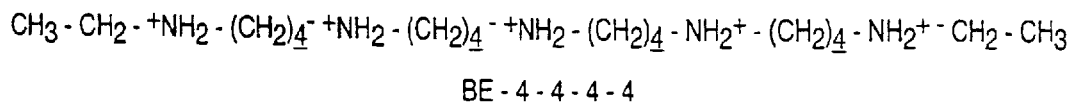
BE - 4 - 4 - 4 - 4
FIG. 2
| POLYAMINE | $K_h \times 10^4$ $(M^{-1})$ | CONCENTRATION AT THE ONSET OF AGGREGRATION (mM) |
|---|---|---|
| SPERMINE | 5.70 | 0.015 |
| BE - 4 - 4 - 4 | 15.77 | 0.390 |
| BE - 4 - 4 - 4 - 4 | 20.00 | 0.020 |

FIG. 17A

| CELL LINES | CONCENTRATION OF BE-4-4-4-4 (μM) | DAY OF TREATMENT | POLYAMINE LEVELS (nmoles/$10^6$ CELLS) | | | |
|---|---|---|---|---|---|---|
| | | | Pu | Sd | Sm | BE-4-4-4-4 |
| U-87 MG | | 1 | 0.68 | 4.19 | 4.29 | - |
| | 0 | 3 | 0.23 | 3.21 | 3.76 | - |
| | 0 | 5 | 0.09 | 2.17 | 3.68 | - |
| | 0 | 7 | ND | 2.47 | 3.45 | - |
| | 5 | 3 | ND | 0.18 | 1.26 | 6.71 |
| | 5 | 5 | ND | 0.17 | 0.57 | 6.36 |
| | 5 | 7 | ND | 0.12 | 0.05 | 10.11 |
| | 10 | 3 | ND | 0.27 | 1.07 | 5.36 |
| | 10 | 5 | ND | ND | 0.70 | 7.66 |
| | 10 | 7 | ND | 0.64 | ND | 13.40 |
| | 50 | 3 | ND | 0.30 | 1.13 | 5.89 |
| | 50 | 5 | ND | 0.12 | 0.47 | 6.90 |
| | 50 | 7 | ND | ND | ND | 18.90 |
| SF-126 | | 1 | 2.16 | 2.17 | 1.51 | - |
| | 0 | 3 | 0.43 | 1.21 | 0.85 | - |
| | 0 | 5 | 0.46 | 1.81 | 1.13 | - |
| | 0 | 7 | 0.21 | 1.10 | 0.77 | - |
| | 5 | 3 | ND | ND | 0.31 | 1.70 |
| | 5 | 5 | ND | ND | 1.08 | 2.89 |
| | 5 | 7 | ND | ND | ND | 3.50 |
| | 10 | 3 | ND | ND | 0.24 | 1.75 |
| | 10 | 5 | ND | ND | 0.13 | 3.03 |
| | 10 | 7 | ND | ND | ND | 3.03 |

FIG. 17B

| CELL LINES | CONCENTRATION OF BE-4-4-4-4 (μM) | DAY OF TREATMENT | POLYAMINE LEVELS (nmoles/10⁶ CELLS) | | | |
|---|---|---|---|---|---|---|
| | | | Pu | Sd | Sm | BE-4-4-4-4 |
| SF-126 (CONTINUED) | | | | | | |
| | 50 | 3 | ND | ND | 0.33 | 1.56 |
| | 50 | 5 | ND | ND | 0.10 | 3.41 |
| | 50 | 7 | ND | ND | ND | 2.82 |
| SF-188 | | | | | | |
| | | 1 | 1.14 | 1.58 | 1.53 | - |
| | 0 | 3 | 1.68 | 2.34 | 2.75 | - |
| | 0 | 5 | 0.63 | 1.65 | 1.70 | - |
| | 0 | 7 | 0.06 | 1.10 | 1.32 | - |
| | 5 | 3 | ND | ND | 0.93 | 4.50 |
| | 5 | 5 | ND | ND | 0.37 | 4.74 |
| | 5 | 7 | ND | 0.27 | 0.51 | 6.25 |
| | 10 | 3 | ND | ND | 0.89 | 6.57 |
| | 10 | 5 | ND | ND | 0.38 | 6.75 |
| | 10 | 7 | ND | ND | 0.30 | 9.00 |
| | 50 | 3 | ND | 0.28 | 1.14 | 8.41 |
| | 50 | 5 | ND | ND | 0.45 | 7.79 |
| | 50 | 7 | ND | ND | 0.60 | 9.53 |
| SF-763 | | | | | | |
| | | 1 | 4.37 | 3.97 | 3.98 | - |
| | 0 | 3 | 3.60 | 3.17 | 3.35 | - |
| | 0 | 5 | 3.40 | 3.10 | 2.95 | - |
| | 0 | 7 | 3.05 | 2.74 | 2.62 | - |
| | 5 | 3 | 0.69 | 0.72 | 1.00 | 5.60 |
| | 5 | 5 | ND | ND | ND | 8.80 |
| | 5 | 7 | ND | ND | 0.38 | 2.80 |

FIG. 17C

| CELL LINES | CONCENTRATION OF BE-4-4-4-4 (µM) | DAY OF TREATMENT | POLYAMINE LEVELS (nmoles/10$^6$ CELLS) | | | |
|---|---|---|---|---|---|---|
| | | | Pu | Sd | Sm | BE-4-4-4-4 |
| SF-763 (CONTINUED) | | | | | | |
| | 10 | 3 | ND | ND | 0.58 | 13.9 |
| | 10 | 5 | 0.44 | 0.37 | 0.37 | 16.7 |
| | 10 | 7 | ND | ND | ND | 7.46 |
| | 50 | 3 | ND | ND | 0.65 | 11.9 |
| | 50 | 5 | ND | ND | ND | 13.2 |
| | 50 | 7 | ND | ND | ND | 5.11 |
| SF-767 | | | | | | |
| | | 1 | 0.57 | 1.35 | 0.73 | - |
| | 0 | 3 | 0.66 | 2.18 | 1.28 | - |
| | 0 | 5 | 0.45 | 1.78 | 1.36 | - |
| | 0 | 7 | 0.42 | 1.19 | 1.28 | - |
| | 5 | 3 | 0.87 | 0.25 | 0.62 | 3.41 |
| | 5 | 5 | ND | ND | 0.20 | 3.60 |
| | 5 | 7 | ND | ND | 0.10 | 3.92 |
| | 10 | 3 | ND | ND | 0.43 | 3.75 |
| | 10 | 5 | ND | ND | 0.18 | 2.48 |
| | 10 | 7 | ND | ND | 0.09 | 2.83 |
| | 50 | 3 | ND | 0.09 | 0.36 | 3.08 |
| | 50 | 5 | ND | ND | 0.21 | 4.49 |
| | 50 | 7 | ND | ND | 0.07 | 2.45 |
| DAOY | | | | | | |
| | | 1 | 4.18 | 8.95 | 2.73 | - |
| | 0 | 3 | 3.28 | 8.50 | 3.08 | - |
| | 0 | 5 | 2.72 | 8.53 | 3.15 | - |
| | 0 | 7 | 0.86 | 6.71 | 2.18 | - |

FIG. 17D

| CELL LINES | CONCENTRATION OF BE-4-4-4-4 (μM) | DAY OF TREATMENT | POLYAMINE LEVELS (nmoles/10⁶ CELLS) | | | |
|---|---|---|---|---|---|---|
| | | | Pu | Sd | Sm | BE-4-4-4-4 |
| DAOY (CONTINUED) | 5 | 3 | ND | 0.80 | 0.71 | 8.37 |
| | 5 | 5 | ND | ND | ND | 17.5 |
| | 5 | 7 | * | * | * | * |
| | 10 | 3 | ND | 0.34 | 0.64 | 11.3 |
| | 10 | 5 | ND | ND | ND | 14.6 |
| | 10 | 7 | * | * | * | * |
| | 50 | 3 | ND | 0.23 | 0.52 | 10.0 |
| | 50 | 5 | ND | ND | ND | 19.6 |
| | 50 | 7 | * | * | * | * |

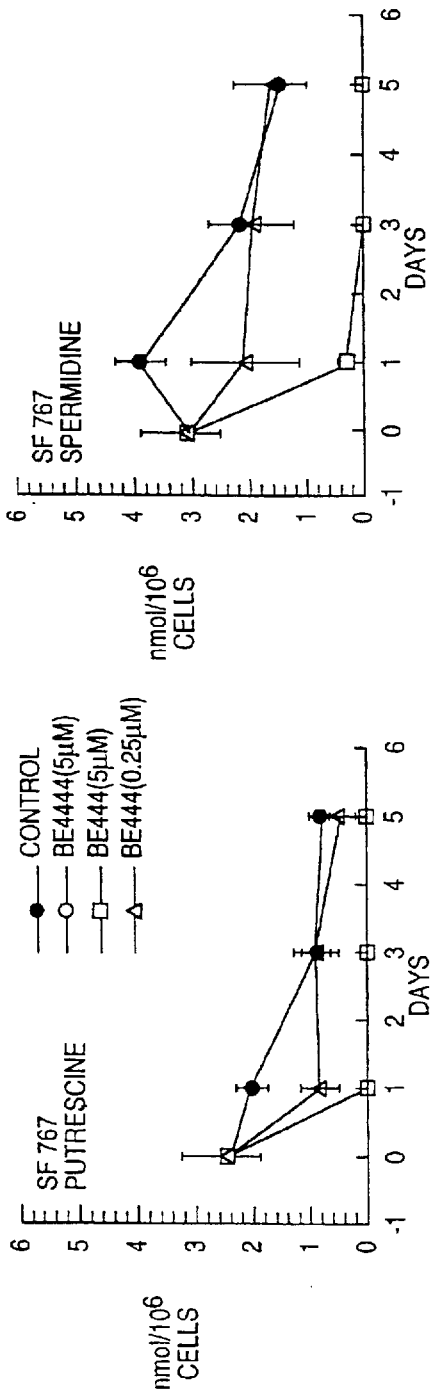
FIG. 24A
FIG. 24B
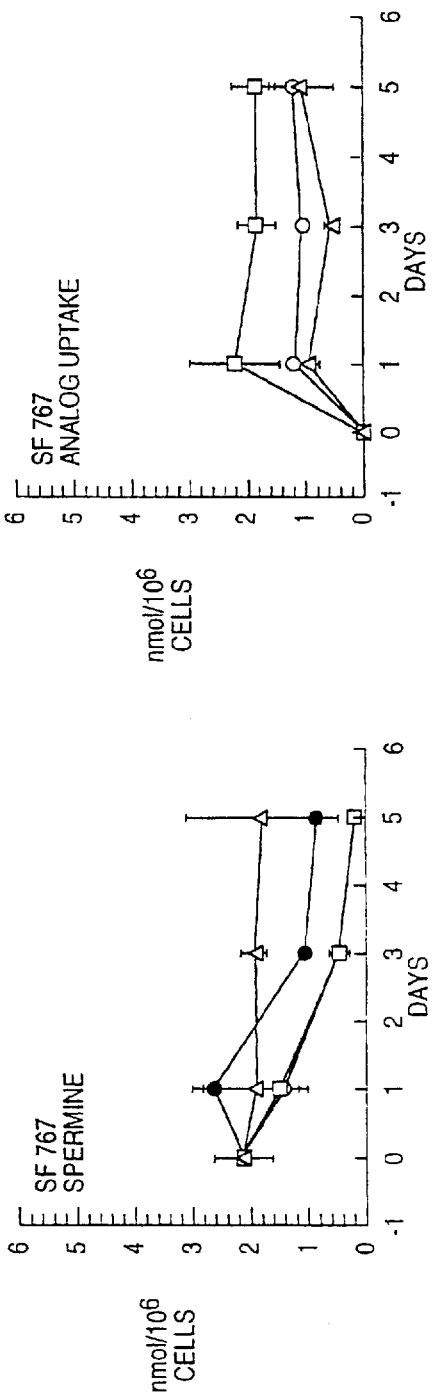
FIG. 24C
FIG. 24D

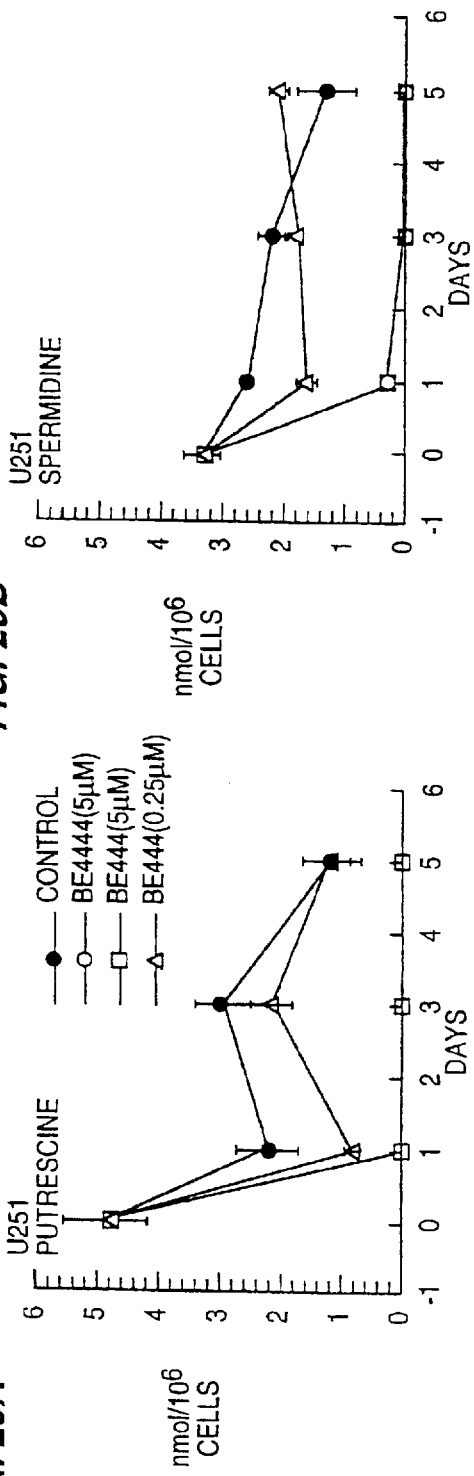
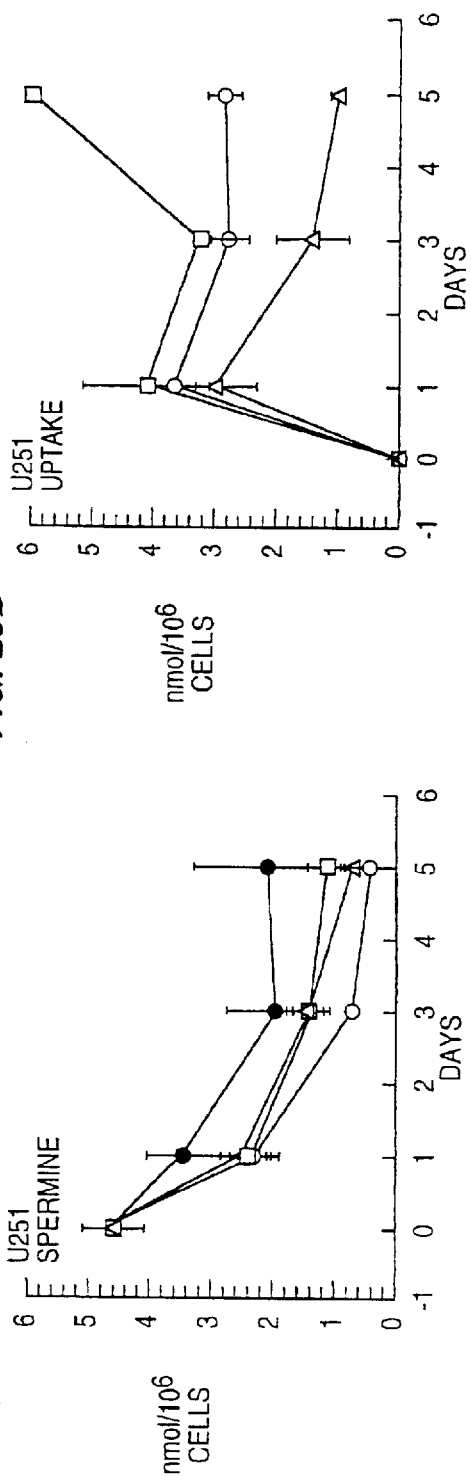
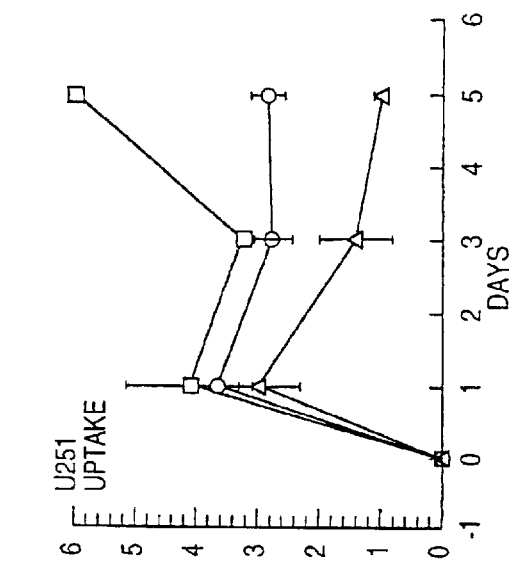
FIG. 25A  FIG. 25B  FIG. 25C  FIG. 25D

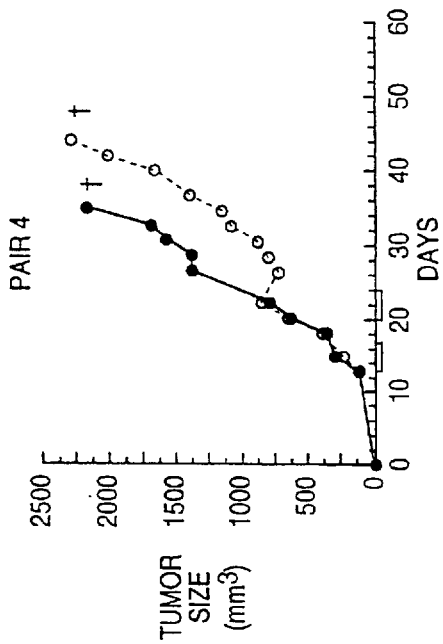
FIG. 32A PAIR 2
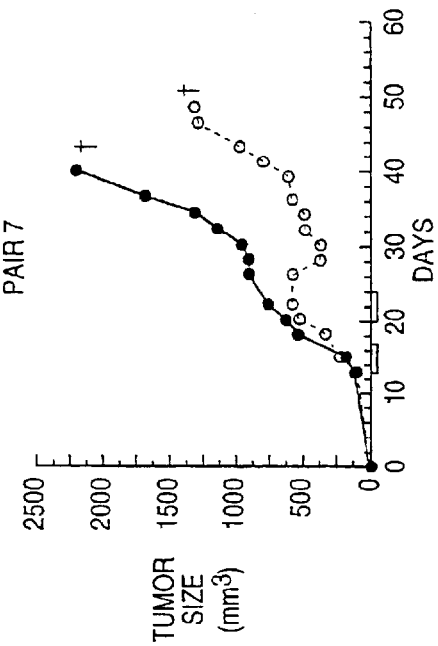
FIG. 32B PAIR 4
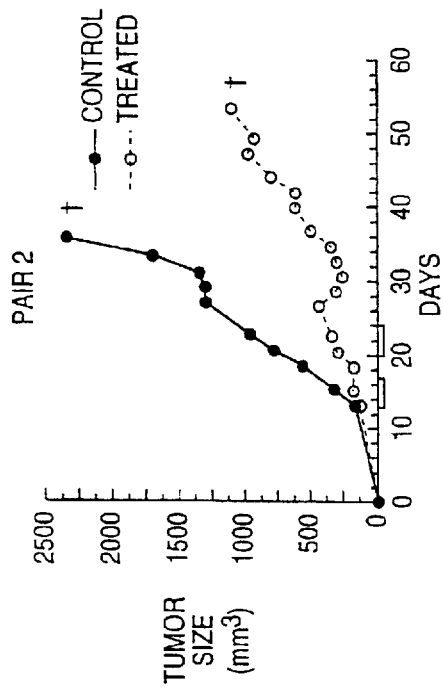
FIG. 32C PAIR 3
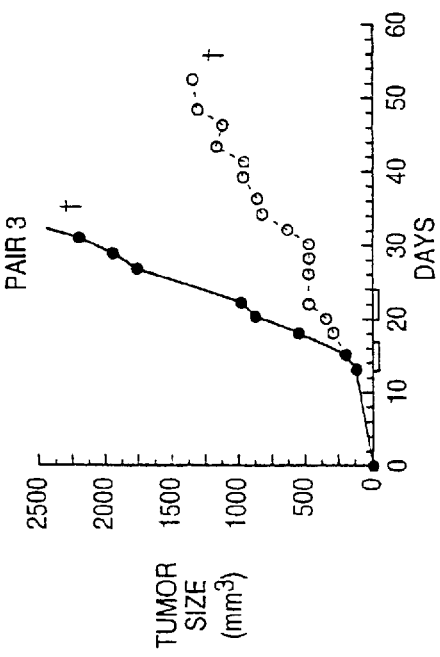
FIG. 32D PAIR 7

PAIR 2

PAIR 3

PAIR 4

PAIR 7

FIG. 35

| TUMOR AND TREATMENT[a] | REGRESSIONS[b] | | | T - C[c] |
|---|---|---|---|---|
| | CYCLE 1 | CYCLE 2 | COMPLETE | |
| SF-767 | | | | |
|   CONTROL | 0/9 | 0/9 | 0/9 | 0 |
|   BE-4-4-4-4 | 8/8 | 8/8 | 3/8 | 19 |
| U-87 MG | | | | |
|   CONTROL | 1/9 | ND[d] | 0/9 | 0 |
|   BE-4-4-4-4 | 0/10 | ND | 0/10 | 6 |
|   BCNU | 8/10 | ND | 1/10 | 22 |
|   BE-4-4-4-4/BCNU | 8/9 | ND | 0/9 | 28 |
| A549 | | | | |
|   CONTROL | 0/7 | 1/7 | 0/7 | 0 |
|   BE-4-4-4-4 | 7/7 | 3/3 | 0/7 | >54 |
|   BCNU | 1/7 | ND | 0/7 | -23 |
|   BE-4-4-4-4/BCNU | 6/7 | 3/3 | 0/7 | >54 |
| HCT116 | | | | |
|   CONTROL | 0/4 | ND | 0/4 | 0 |
|   BE-4-4-4-4 | 4/4 | ND | 0/4 | >7 |
| HT29 | | | | |
|   CONTROL | 0/8 | ND | 0/8 | 0 |
|   BE-4-4-4-4 | 0/8 | ND | 0/8 | 10 |
|   BCNU | 0/6 | ND | 0/6 | -1 |
|   BE-4-4-4-4/BCNU | 2/8 | ND | 0/8 | 16 |

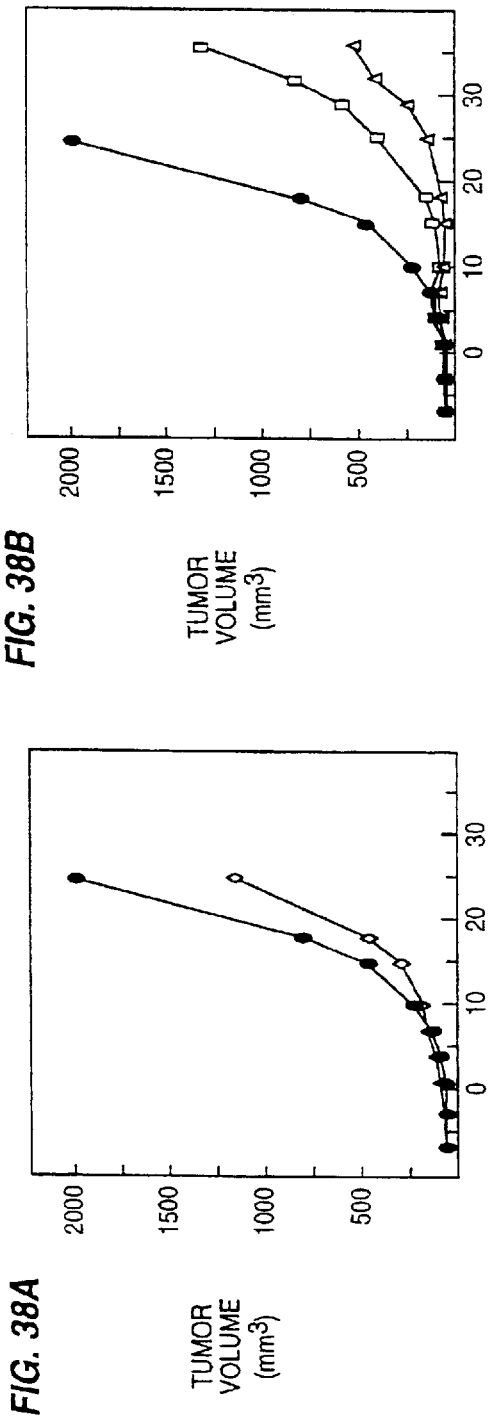
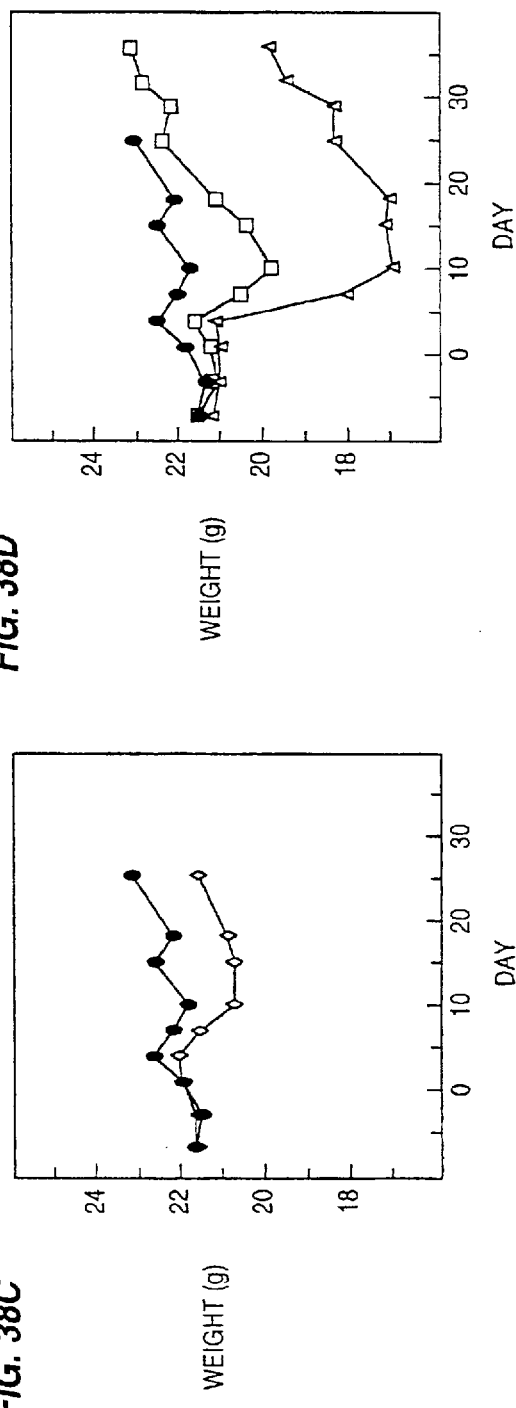
FIG. 38A
FIG. 38B
FIG. 38C
FIG. 38D

FIG. 45

| TREATMENT | NUMBER OF CYCLES | MITOTIC INDEX (NUMBER/10 hpf) |
| --- | --- | --- |
| CONTROL | | 70 |
| BE-4-4-4-4 | 1 | 5 |
| BE-4-4-4-4 | 2 | 4 |
| BE-4-4-4-4/BCNU | 1 | 4 |
| BE-4-4-4-4/BCNU | 2 | 2 |

FIG. 46

| CELL LINE | TREATMENT | SSAT ACTIVITY (pmole/min/mg PROTEIN) | SD[a] |
| --- | --- | --- | --- |
| U-251 MG | CONTROL | 3.63 | 49.53 |
| | BE-4-4-4-4 | 4.39 | 17.40 |
| SF-767 | CONTROL | 5.40 | 69.94 |
| | BE-4-4-4-4 | 74.03 | 4.97 |

THERAPEUTIC POLYAMINES

This application is a division of application Ser. No. 08/147,527, filed Nov. 5, 1993 now U.S. Pat. No. 5,541,230.

BACKGROUND OF THE INVENTION

Polyamine metabolism has long been a target of cancer chemotherapy. Natural polyamines, such as putrescine, spermidine and spermine, are simple aliphatic amines produced in eukaryotic cells by a highly regulated metabolic apparatus. Spermine is the largest of the three major polyamines involved in polyamine-dependent cell growth, and has a formula of $NH_2(CH_2)_3NH(CH_2)_4NH(CH_2)_3NH_2$. The formulas for putrescine and spermidine are $NH_2(CH_2)_4NH_2$ and $NH_2(CH_2)_4NH(CH_2)_3NH_2$, respectively.

Polyamine levels and the activity of the polyamine biosynthetic apparatus tend to be high in dividing mammalian cells and low in quiescent cells. Previous studies have shown that populations of cells depleted of their polyamine content stop growing and may die.

For example, α-difluoromethylornithine, often known as "DFMO" or "Eflornithine", is an inhibitor of polyamine biosynthesis. This compound depletes cellular putrescine and spermidine by inhibiting the enzyme ornithine decarboxylase. DFMO is currently in clinical trials as a chemotherapeutic agent for cancer treatment. A somewhat less specific polyamine inhibitor than DFMO, the compound methylglyoxal-bis(guanylhydrazone), known as "MGBG" or "Methyl-GAG", also is being tested as a chemotherapeutic agent. The clinical interest in these drugs reflect the conventional view that polyamine biosynthesis may be a useful target for cancer prevention and treatment. Unfortunately, these compounds have only demonstrated limited success against cancer and other growth related disorders. There are two likely reasons for this limited efficacy.

The first reason involves the extent of depletion of cellular polyamines. Although several compounds are powerful inhibitors of polyamine biosynthesis, they do not completely deplete a cell of its polyamine content. Apparently, cancerous cells are able to scavenge enough natural polyamines needed to live in spite of the use of the inhibitors.

The second reason involves the function of the polyamines. Polyamine biosynthetic inhibitors do not directly attack the functional target of the natural polyamines. Rather, these inhibitors merely reduce the levels of the natural polyamines, which are needed to promote growth.

The limited success of the polyamine inhibitors means that other strategies must be undertaken to reap the full benefit of chemotherapeutic approaches based on the polyamines. The inventive polyamine analogs described herein yield chemotherapeutic benefits not achieved by the polyamine inhibitors.

SUMMARY OF THE INVENTION

It is therefore an object of the present invention to provide a compound which mimics a natural polyamine in many interactions with other entities involved in polyamine-dependent cell growth, but that does not perform the polyamine functions needed to support cell growth.

It is another object of the present invention to provide a compound that is a polyamine analog with antineoplastic properties, that is, it prevents or retards the growth of cancerous cells and other pathological cells.

It is still another object of the present invention to provide a polyamine analog that is longer than spermine.

It is yet another object of the present invention to provide a compound, of the formula $N^1,N^{19}$-bis(ethylamino)- 5,10, 15-triazanonadecane ("BE-4-4-4-4") or related compounds for use as an antineoplastic agent.

It is still a further object to provide a method of treating cancer and other abnormalities with a polyamine analog.

It is yet a further object of the present invention to provide a method of treating cancer and other abnormalities with BE-4-4-4-4 or related compounds.

It is yet another object of the present invention to provide a combination therapy based on administration of BE-4-4-4-4 or related compounds along with other known chemotherapeutic agents.

In accomplishing these and other objects, there are herein provided polyamine analogs useful as a cancer chemotherapeutic agent. These polyamine analogs include molecules having a formula $R_1$—NH—$(CH_2)_w$—NH—$(CH_2)_x$—NH—$(CH_2)_y$—NH—$(CH_2)_z$—NH—$R_2$, wherein $R_1$ and $R_2$ are hydrocarbon chains having 1 to 5 carbons and w, x, y and z are integers of 1 to 10. More preferably, $R_1$ and $R_2$ are hydrocarbon chains having 2 to 4 carbons and w, x, y and z are an integers of 2 to 5. Even more preferable, $R_1$ and $R_2$ are hydrocarbon chains having 2 carbons and w, x, y and z are integers of 3 to 4. Additionally, substitutions of certain hydrogens and carbons with other atoms or molecules may be undertaken without departing from the scope of the present invention.

The preferred polyamine analog is longer than spermine, and comprises at least four subunits of methylene groups separated by amine groups. This preferred compound, BE-4-4-4-4, may be used alone or in combination with other therapeutic agents, such as 1,3-bis(2-chloroethyl)-1-nitrosourea ("BCNU") or platinum containing compounds, such as cis-diamminedichloroplatinum (II) ("cis-Pt") and related entities. The other compounds of the present invention may also be employed in combination with other therapeutic agents.

A therapeutic regimen for using polyamine analogs, such as BE-4-4-4-4, is provided. Additionally, the combination therapies mention above may be administered in a concurrent or sequential manner.

BRIEF DESCRIPTION OF FIGURES

FIG. 1 depicts the formulas of spermine, $N^1$, $N^{14}$-bis-(ethyl)-amino-5,10-diazatetradecane ("BE-4-4-4") and $N^1$, $N^{19}$-bis-(ethylamino)-5,10,15-triazanonadecane ("BE-4-4-4-4").

FIG. 2 depicts in chart form the aggregation of calf thymus DNA by spermine, BE-4-4-4 and BE-4-4-4-4.

FIG. 17 sets forth the polyamine level data for other cell lines. "Pu" means putrescine; "Sd" means spermidine; "Sm" means spermine; "ND" means not detectable; "*" means that no cells were found attached to the flask.

FIG. 24 depicts the polyamine and polyamine analog levels of SF-767 cells treated with BE-4-4-4-4 or BE-4-4-4. Values are based on the average of three separate experiments.

FIG. 25 depicts the polyamine and polyamine analog levels of U-251 MG cells treated with BE-4-4-4-4 or BE-4-4-4. Values without an asterisk are based on the average of three separate experiments. Values with an asterisk are based on the average of two separate experiments.

FIG. 32 depicts tumor size as a function of time in four representative pairs of nude mice bearing U-251 MG tumors. The mice were treated with 6 mg/kg b.i.d. of BE-4-4-4-4 in the 4/3/4 regimen. Crosses represent the day of death. Bars along the abscissa represent periods of therapy.

FIG. 35 lists data from the treatment of various subcutaneous human tumor xenotrafts in athymic mice with BE-4-4-4-4 with or without BCNU. "T-C" signifies the difference in days between the median time of treated ("IT") and control ("C") mice to reach a volume 5 times greater than the volume at the time of original treatment. "ND" means not determined.

FIG. 38 depicts the growth rate of U-87 MG xenografts treated with BE-4-4-4-4±BCNU. Graphs A and C concern nude mice carrying SF-767 tumors which were administered i.p. injections of saline (●) or 5 mg/kg b.i.d. of BE-4-4-4-4 on the 4/3/4 schedule for 1 cycle (◊). Graphs B and D concern mice treated with 50 mg/kg BCNU alone (□) or BE-4-4-4-4 (same treatment schedule) with BCNU 40 mg/kg for 1 cycle (Δ). Graphs A and B depict tumor volume for each group, and graphs C and D depict body weights for each group. Data points represent the mean tumor volume and body weight for 9–10 mice per group.

FIG. 45 shows the mitotic index of A549 xenografts after treatment with BE-4-4-4-4. Replicate sections for histopathological examination. The number of mitosis were counted in 10 high-power fields ("hpf").

FIG. 46 lists the activity of Spermidine/spermine-$N^1$-acetyltransferase in U-251 MG and SF-767 cells treated with BE-4-4-4-4.

DETAILED DESCRIPTION OF PREFERRED EMBODIMENTS

Figure 3:
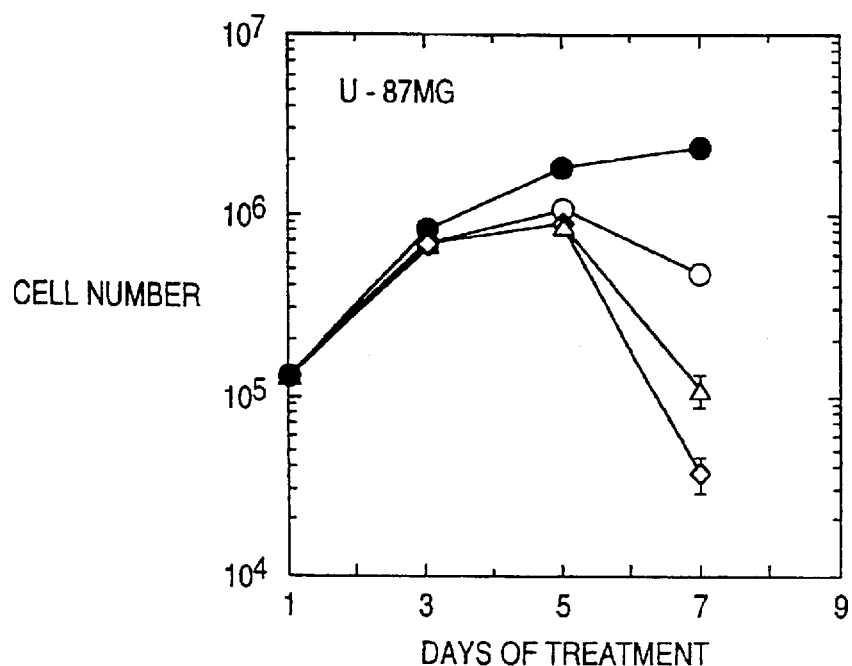
FIG. 3 depicts the effects of 0 (●),5 (○), 10 (Δ), and 50 μM (◇)BE-4-4-4-4 on the growth of U-87 MG cells. Values are an average of the results of three separate experiments. Error bars, where not visible, are smaller than symbol size.
Figure 4:
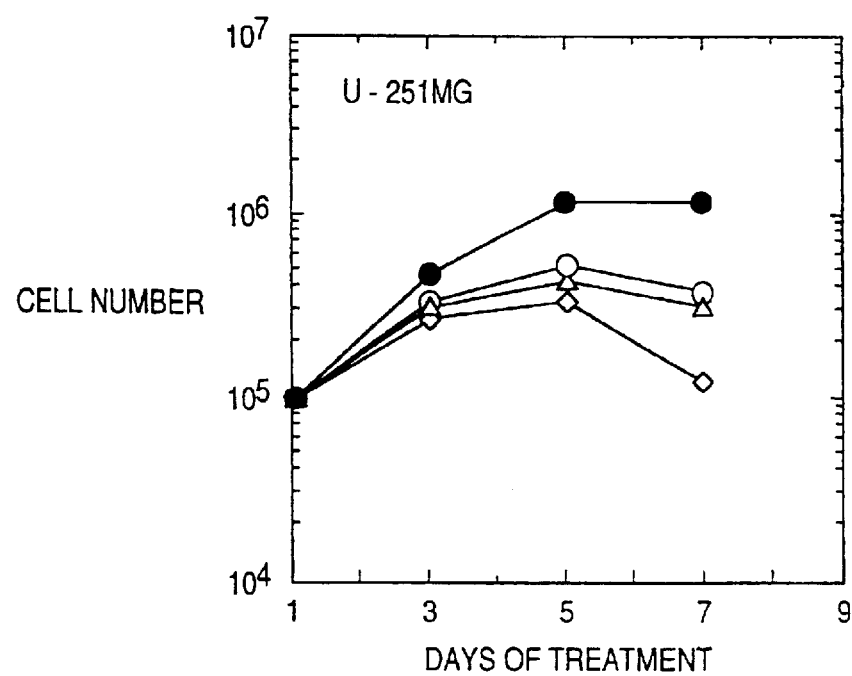
FIG. 4 depicts the effects of BE-4-4-4-4 on the growth of U-251MG cells. Symbols and explanation set forth for FIG. 3 also pertain to this figure.
Figure 5:
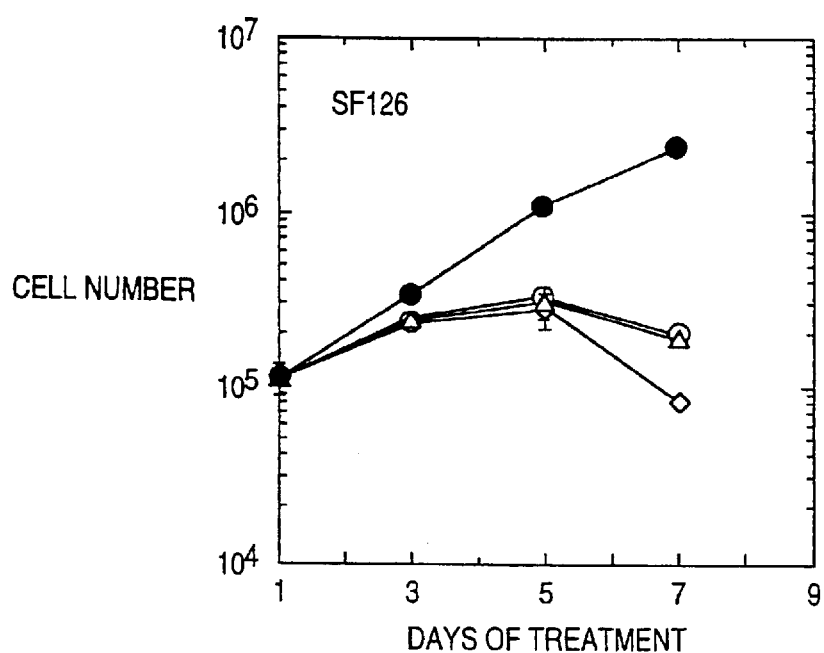
FIG. 5 depicts the effects of BE-4-4-4-4 on the growth of SF-126 cells. Symbols and explanation set forth for FIG. 3 also pertain to this figure.

In view of the limitations of polyamine inhibitors, other strategies of cancer chemotherapy were considered. One strategy was to develop compounds that mimic some of the interactions that natural polyamines have in cellular growth pathways, but that do not perform the pertinent functions of the natural polyamines. Such a compound would enter and, by their very presence, disable those pathways. Compounds thus characterized would be antineoplastic agents, that is, they would reverse, prevent or minimize the growth of cancer cells and other cell types displaying abnormal growth.

Pursuant to this strategy, attention focused on spermine, the largest of the three major polyamines implicated in cell growth. Analogs of spermine have been previously made, such as $N^1$, $N^{14}$-bis-(ethyl)-amino-5,10-diazatetradecane ("BE-4-4-4"). Limitations, however, also exist with the known spermine analogs. For example, BE-4-4-4 is quite toxic to some types of cells, but is ineffective against others. Additionally, BE-4-4-4 may present therapeutic control problems in that it is difficult to inhibit, block or reverse its effects once administered. Finally, BE-4-4-4 appears to operate by stimulating Spermidine/spermine-N1-acetyltransferase ("SSAT"), which depletes cells of their natural polyamine content. In this respect, BE-4-4-4 appears to act as the polyamine inhibitors in that it relies on reducing the natural polyamine content of cells.

Polyamine analogs that possess an additional subunit of $(CH_2)_n NH_2$ relative to spermine and BE-4-4-4 have been discovered still to possess an ability to enter and disable the cellular growth pathways. The compounds of the present invention, containing the additional subunit, have the general formula $R_1$—NH—$(CH_2)_w$—NH—$(CH_2)_x$—NH—$(CH_2)_y$—NH—$(CH_2)_z$—NH—R, wherein $R_1$ and $R_2$ are hydrocarbon chains having 1 to 5 carbons and w, x, y and z integers of 1 to 10. More preferably, $R_1$ and $R_2$ are hydrocarbon chains having 2 to 4 carbons and w, x, y and z are an integers of 2 to 5. Even more preferable, $R_1$ and $R_2$ are hydrocarbon chains having 2 carbons and w, x, y and z are integers of 3 to 4.

All of the compounds of the present invention have four subunits of $(CH_2)_n NH_2$, where n is an integer of 1 to 10. The presence of the four subunits appears to eliminates growth-promoting conformational activity in these inventive compounds, as well as increasing the their affinity for DNA as compared to the affinity of spermine. Additionally, groups $R_1$ and $R_2$ protect the inventive compounds against degradation in vivo, and appear to add to the toxicity of the compound.

Choosing a compound from among those within the above formula is influenced, for therapeutic purposes, by factors such as the (1) the ability of the cellular polyamine uptake system to recognize the analog, (2) maintaining sufficient hydrophilicity to insure proper solubility, (3) insuring that the analog has sufficient affinity to bind to DNA, but does not impart the conformational changes (aggregation) needed to promote growth and (4) protecting the analog against degradation. Simple screening based on any of the above considerations can be effected to determine other preferred compounds within the invention. For example, a compound within the above formula that has a higher affinity for DNA than spermine, but that is not able to effect growth-promoting conformational change (aggregate) DNA as well or in the same manner as spermine, is a good candidate for in vivo use. The preferred compound, $N^1$, $N^{19}$-bis-(ethylamino)-5,10, 15-triazanonadecane ("BE-4-4-4-4"), binds DNA better than spermine but does not impart the conformational changes to DNA which are caused by spermine. BE-4-4-4-4 also does not effect changes in the cellular levels of SSAT which accompany the administration of BE-4-4-4. Accordingly, depletion of natural polyamines by SSAT does not account for the antineoplastic activity of BE-4-4-4-4. Rather, by binding to DNA but not effecting growth-promoting conformational changes, BE-4-4-4-4 displaces the natural polyamines and prevents the conformational changes required for growth.

The formula of BE-4-4-4-4 as compared to those of BE-4-4-4 and spermine are depicted in FIG. 1. From FIG. 1, it is apparent that BE-4-4-4-4 is longer than spermine and BE-4-4-4. The additional length of BE-4-4-4-4, primarily through the presence of the fourth subunit, appears to account for the elimination of the conformation altering activity possessed by spermine. Additionally, BE-4-4-4-4 is a bis-ethylated compound. Bis-ethylation blocks degradation of BE-4-4-4-4 by plasma polyamine oxidases, and may also increase the antineoplastic activity of this compound.

Compounds of the invention can be produced via well-known organic synthesis techniques. These synthesis techniques can be based on the use of commercially available intermediaries or through organic modifications of existing polyamines. An exemplary synthesis protocol for the preferred compound BE-4-4-4-4 is described below.

EXAMPLE 1. SYNTHESIS OF BE-4-4-4-4

A variety of known chemical reactions can be employed to synthesize BE-4-4-4-4. One approach is to use two intermediates, namely N-p-toluenesulfonyl-N-ethyl-4-bromobutylamine and $N^1,N^5,N^9$-tribenzyl-5-aza-1,9-diaminononane.

N-p-toluenesulfonyl-N-ethyl-4-bromobutylamine

Step 1. EtNH$_2$+Tosyl-Cl→EtNH-tosyl+HCl

To synthesize N-p-toluenesulfonyl-N-ethyl-4-bromobutylamine, 18.4 mmol EtNH$_2$ HCl, 6 ml Et$_2$NH and 18.8 mmol tosyl chloride are dissolved in 60 ml CH$_2$Cl$_2$, and the mixture is stirred for 12 hours at room temperature. About 10 ml H$_2$O is added and stirring is continued for another two hours in order to decompose excess tosyl chloride. After washing with water and filtering with paper, the organic phase is evaporated. The residue (tosylated ethylamine) is then dissolved in methyl alcohol and then recrystallized.

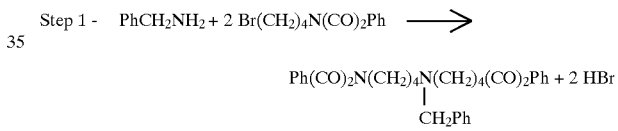

Next, 12.6 mmol tosylated ethylamine is dissolved in 36 ml dry N,N-dimethylformamide ("DMF"). Thereafter, 17 mmol NaH (60% in oil) is added to the solution at room temperature. Hydrogen gas evolves and the reaction mixture becomes sticky. Thirty minutes after adding NaH, 73.7 mmol 1,4-dibromobutane is added to the sticky solution. After vigorous stirring, the solution becomes clear. The solution is then slowly stirred overnight. The reaction mixture is then added to 200 ml of cold water and thereafter extracted twice with 200 ml ether. The ether phase is washed with water and then evaporated. The resulting oily residue is dissolved in benzene, which in turn is placed on a 120 g silica gel column equilibrated in benzene. After eluting with 500 ml benzene, the solvent is then changed to a mixture of benzene and acetone (20:1). Fractions were collected and evaporated to obtain pure oily N-p-toluenesulfonyl-N-ethyl-4-bromobutylamine.

$N^1,N^5,N^9$-tribenzyl-5-aza-1,9 diaminononane

First, N-(4-bromobutyl)phthalimide is synthesized from a mixture of 30 mmol potassium phthalimide and 100 mmol 1,4 dibromobutane in 50 ml DMF. The solution is stirred for 2 hours at 60° C., and the DMF and 1,4-dibromobutane is evaporated off in vacuo. The remaining residue is extracted with CHCl$_3$ and H$_2$O. The resulting white compound is recrystallized from ethyl alcohol. See Chem. Pharm. Bull. 32: 3428 (1984).

Step 1 - PhCH$_2$NH$_2$ + 2 Br(CH$_2$)$_4$N(CO)$_2$Ph ⟶

Ph(CO)$_2$N(CH$_2$)$_4$N(CH$_2$)$_4$(CO)$_2$Ph + 2 HBr
|
CH$_2$Ph

A stirred solution of 6 mmol benzylamine and 14 mmol N-(4-bromobutyl)phthalimide in 24 ml CH$_3$CN was refluxed for 14 hours in the presence of 2.4 g KF-Celite. After removal of the KF-Celite, the filtrate is evaporated in vacuo and the residue is dissolved in 10 ml benzene. This solution is then placed on a 20 g silica gel column equilibrated with benzene. The column is then successively eluted with 100 ml benzene and 100 ml benzene/acetone (20:1). The solvent is then removed from the last fraction. See Chem. Pharm. Bull. 34: 1032–1038 (1986).

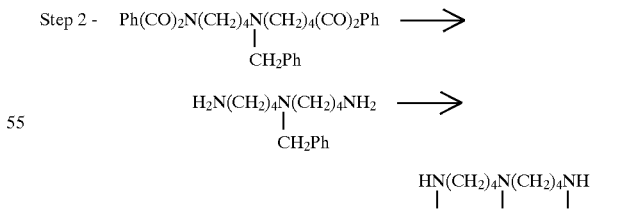

A solution of N,N-bis(4-phthalimidobutyl)benzylamine (3.7 mmol) in 34 ml methyl alcohol containing 2.8 ml NH$_2$NH$_2$ H$_2$O is refluxed for 3 hours and then evaporated in vacuo. The residue is shaken for 30 minutes with 34 ml of CHCl$_3$ and 34 ml 4N NH$_4$OH. The ammonia phase is re-extracted with 34 ml CHCl$_3$. The CHCl$_3$ fractions are combined, filtered with paper and evaporated. This yields 3.5 mmol $N^5$-benzyl-5-aza-1,9-diaminononane, which is dissolved in 14 ml methyl alcohol containing 7.0 mmol benzaldehyde and 1.1 g $MgSO_4$. The solution is stirred for one hour at room temperature. Then, the solution is placed in an ice bath, and 0.8 g $NaBH_4$ and 10 ml methyl alcohol is added to the solution over a period of 1 hour. The solution is then stirred for an additional hour. The methyl alcohol is then removed in vacuo, and the residue is extracted twice with 25 ml $Et_2O$ and once with 25 ml $H_2O$. The $Et_2O$ extracts are combined and then washed twice with 25 ml of $H_2O$. The $Et_2O$ is then removed, yielding $N^1,N^5,N^9$-tribenzyl-5-aza-1,9-diaminononane.

To synthesize BE-4-4-4-4, 35.5 mmol N-p-toluenesulfonyl-N-ethyl-4-bromobutylamine and 14.8 mmol $N^1,N^5,N^9$-tribenzyl-5-aza-1,9-diaminononane are dissolved in 60 ml $CH_3CN$, which is then stirred and refluxed in the presence of 15.3 g KF celite for 16–18 hours. The reaction mixture is filtered and the filtrate is evaporated to dryness. The residue is then dissolved in benzene, loaded on a silica gel column (300 g), and eluted with benzene/acetone (5:1). The purified product is hydrolyzed in 6M HCl at 120° C. for 5 days, followed by reductive elimination of benzyl groups with 10% palladium/carbon in a hydrogen atmosphere. The BE-4-4-4-4 obtained from this process is crystallized from aqueous ethyl alcohol as a pentahydrochloride salt.

EXAMPLE 2. IN VITRO ANALYSIS OF BE-4-4-4-4

Physico-chemical Studies

The effects of BE-4-4-4-4, BE-4-4-4 and spermine on aggregation and $T_m$ of calf-thymus DNA were studied spectroscopically in 50 mM NaCl, 1 mM Na-cacodylate (pH 7) using a Perkin-Elmer Lambda 4c uv/visible spectrophotometer equipped with a multicell transporter, an electrical heating system, and an IBM-AT-compatible personal computer using Softways (Moreno Valley, Calif.) data collection software. Basu et al., *Biochem. J.* 269: 329–34 (1990). The association parameters for the DNA-pentamine system were determined from a plot of $T_m$ versus concentration of these compounds. Basu et al., *Biochem. J.* 244: 243–46 (1987).

These studies revealed that BE-4-4-4-4 had a higher affinity for DNA than either spermine or BE-4-4-4 and was slightly less efficient than spermine but more efficient than BE-4-4-4 at aggregating DNA. See FIG. 2.

Effect on Tissue Culture Cell Lines

Human tumor cell lines U-87 MG, U-251 MG, SF-126, SF-188, SF-295, SF-763, SF-767, and DAOY were grown in monolayer culture and analyzed for polyamine and BE-4-4-4-4 content by the method of Kabra et al., *J. Chromatog. Biomed. Appl* 380: 19–32 (1986). In multiple 25 $cm^2$ plastic flasks, approximately 1×10 cells were seeded in 5 ml of minimal essential medium, supplemented with nonessential amino acids and 10% fetal calf serum. The cells were incubated for 24 hours and then treated with 5, 10, or 50 μM BE-4-4-4-4. This point is defined as "Day 1" of treatment. A stock solution of BE-4-4-4-4 was prepared in Hanks' balanced salt solution (pH adjusted to 7.2) and was sterile-filtered immediately before use. Basu et al., *Cancer Res.* 49: 5591–97 (1989). The cells were harvested in triplicate on the third, fifth, and seventh days of treatment and counted using an electronic particle counter.

Figure 6:
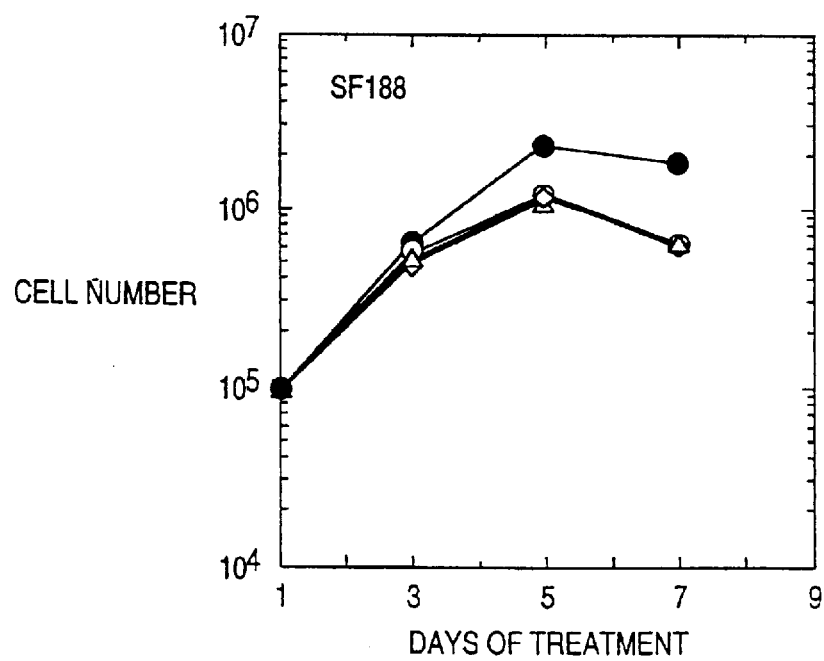
FIG. 6 depicts the effects of BE-4-4-4-4 on the growth of SF-188 cells. Symbols and explanation set forth for FIG. 3 also pertain to this figure.
Figure 7:
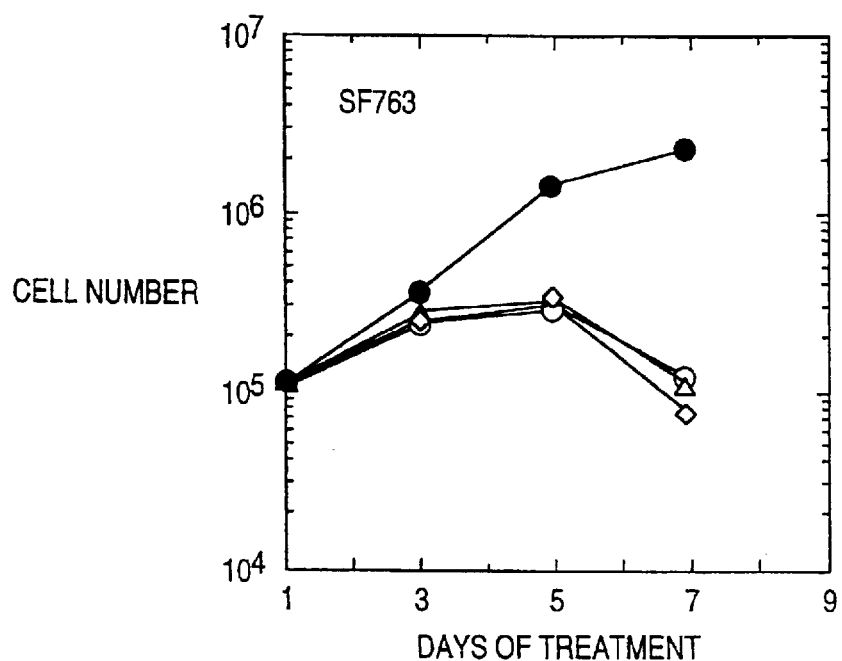
FIG. 7 depicts the effects of BE-4-4-4-4 on the growth of SF-763 cells. Symbols and explanation set forth for FIG. 3 also pertain to this figure.
Figure 8:
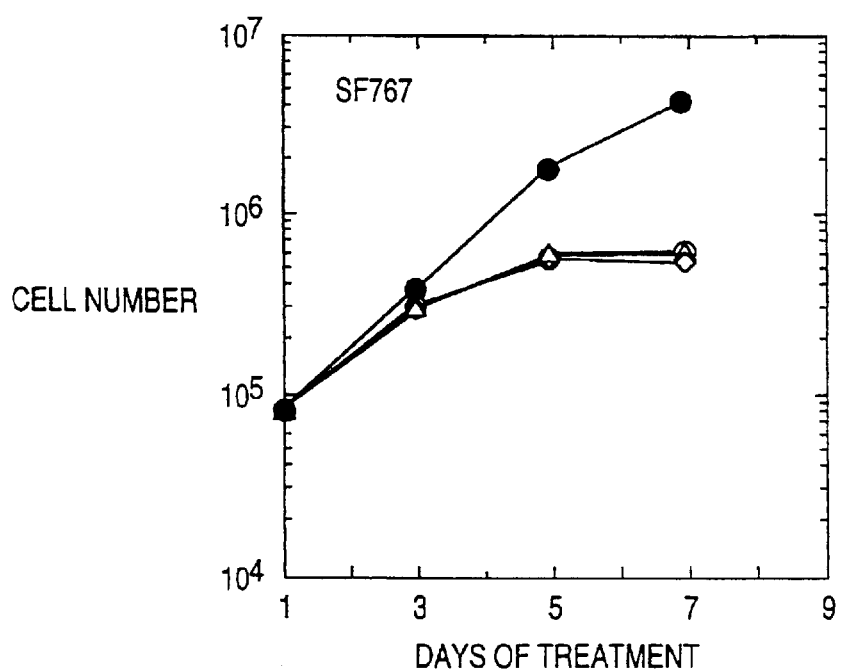
FIG. 8 depicts the effects of BE-4-4-4-4 on the growth of SF-767 cells. Symbols and explanation set forth for FIG. 3 also pertain to this figure.
Figure 9:
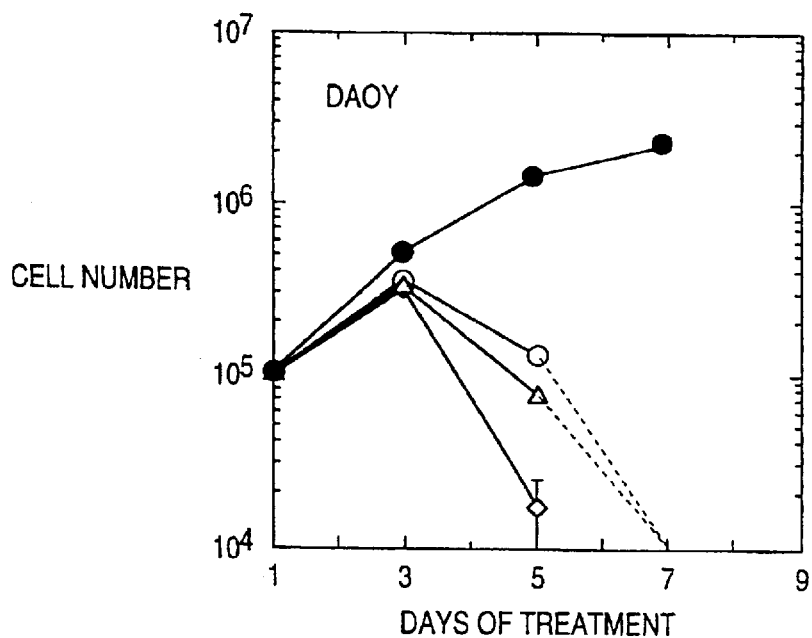
FIG. 9 depicts the effects of BE-4-4-4-4 on the growth of DAOY cells. Symbols and explanation set forth for FIG. 3 also pertain to this figure. By day 7, there were not enough cells attached for an accurate count.
Figure 10:
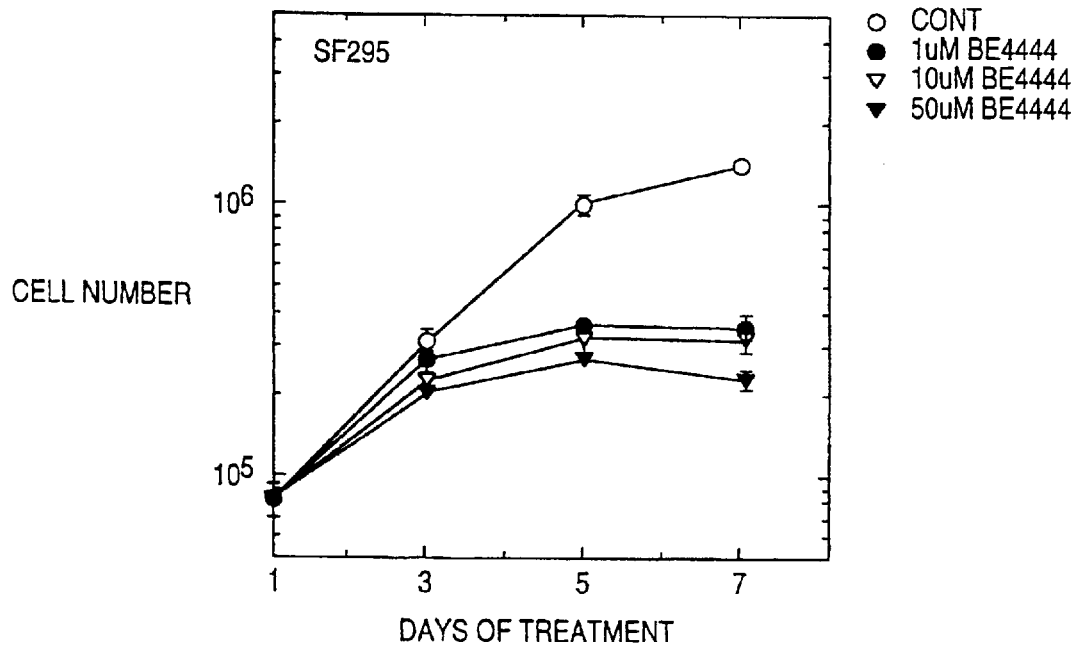
FIG. 10 depicts the effects of 1 μM(●), 10 μM (▽) and 50 μM (▼) BE-4-4-4-4 on SF295 cells.

BE-4-4-4-4 inhibited growth in each of the cell lines tested. See FIGS. 3–10. The inhibition was most pronounced in DAOY and least pronounced in SF-188. By the seventh day of treatment, no DAOY cells were attached to the drug treated flasks. See FIG. 9. The dose response for growth inhibition reached a plateau at 5 μM in SF-188, SF-763, and SF-767 cells. See FIGS. 6–8. In U-87 MG and DAOY cells, growth inhibition increased throughout the dose range, although the response was less extreme in U-87 MG cells than in DAOY cells. In U-251 MG and SF-126 cells, the inhibitory effect increased to a small degree after 7 days of treatment with 50 μM BE-4-4-4-4.

Reversal and Blocking Studies

U-251 MG and SF-763 cells were tested in reversal studies. For these studies, 1 mM putrescine or 20 μM spermidine or spermine was added to the medium 24 hours after the addition of BE-4-4-4-4 to U-251 MG or SF-763 cells. These concentrations of polyamines are sufficient to completely reverse the growth-inhibitory effect of DFMO on 9L rat brain tumor cells and U-87 MG human brain tumor cells. Basu et al., *Cancer Res.* 49: 5591–97 (1989).

Figure 11:
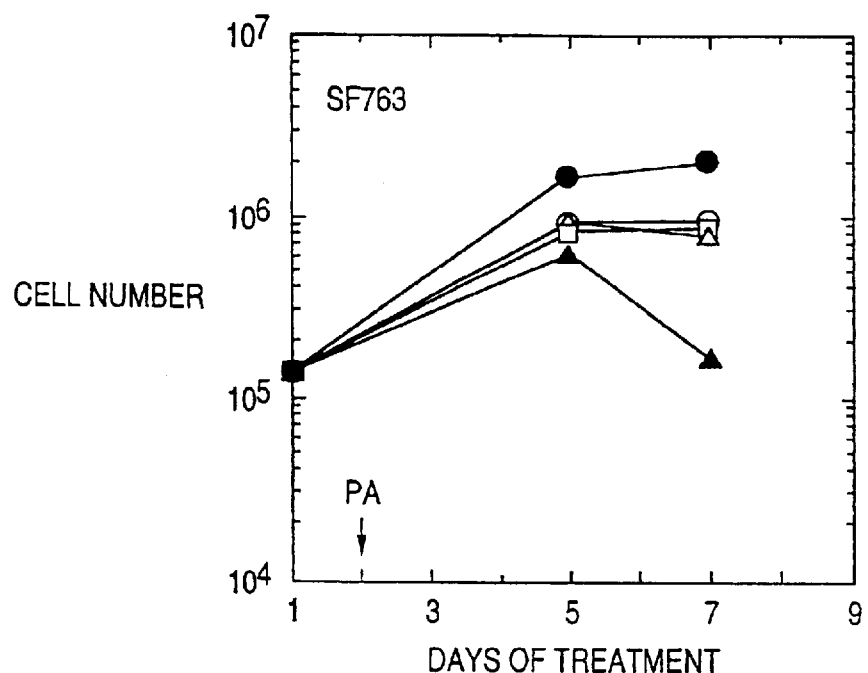
FIG. 11 depicts the reversal in SF-763 cells of growth inhibitory effects of 10 μM BE-4-4-4-4 by addition of polyamines 1 day after BE-4-4-4-4 treatment. Compounds in the following amounts were added: Control (●), BE-4-4-4-4 (▲), BE-4-4-4-4+1 mM putrescine (Δ), BE-4-4-4-4+ 20 μM spermidine (□), BE-4-4-4-4+20 μM spermine (○). Values are an average of the results of three separate experiments. Error bars are smaller than symbol size.
Figure 12:
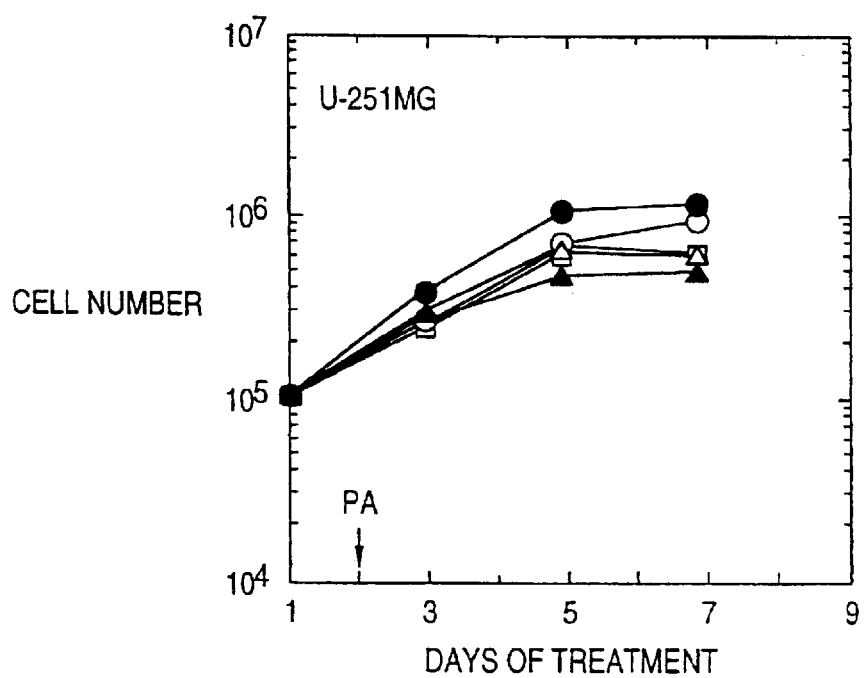
FIG. 12 depicts the reversal in U-251 MG cells growth inhibitory effects of 10 μM BE-4-4-4-4 by addition of polyamines 1 day after BE-4-4-4-4 treatment. Symbols and explanation set forth for FIG. 10 also pertain to this figure.

Addition of polyamines to SF-763 cells 24 hours after BE-4-4-4-4 treatment partially reversed growth inhibition on the seventh day of treatment. See FIG. 11. In U-251 MG cells, the inhibitory effect was completely reversed on Day 7 by spermine but not by putrescine or spermidine. See FIG. 12. In view of the above, the growth-inhibitory effect of BE-4-4-4-4 was less pronounced on U-251 MG cells than on SF-763 cells.

For blocking studies, the polyamines were added along with BE-4-4-4-4. See Basu et al., *Biochem. J.* 269: 329–34 (1990). Before spermidine or spermine addition, 1 mM aminoguanidine was added to inhibit serum amine oxidases.

Figure 13:
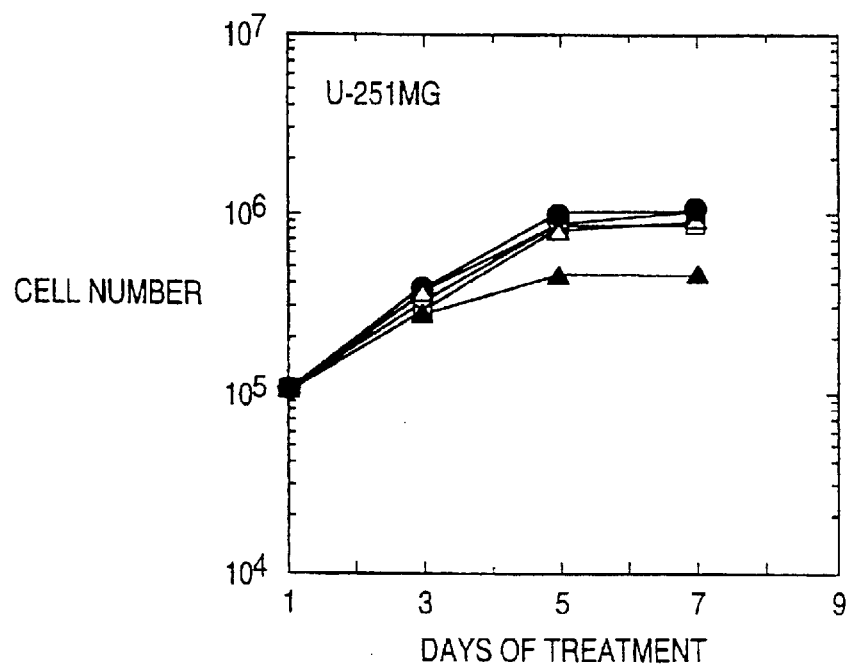
FIG. 13 depicts the blocking in UF-251 MG cells of growth inhibitory effects of 10 μM BE-4-4-4-4 by polyamines added simultaneously with BE-4-4-4-4. Control (●), BE-4-4-4-4 (▲), BE-4-4-4-4+1 mM putrescine (Δ), BE-4-4-4-4+20 μM spermidine (□), BE-4-4-4-4+20 μM spermine (○). Values are an average of the results of three separate experiments. Error bars are smaller than symbol size.
Figure 14:
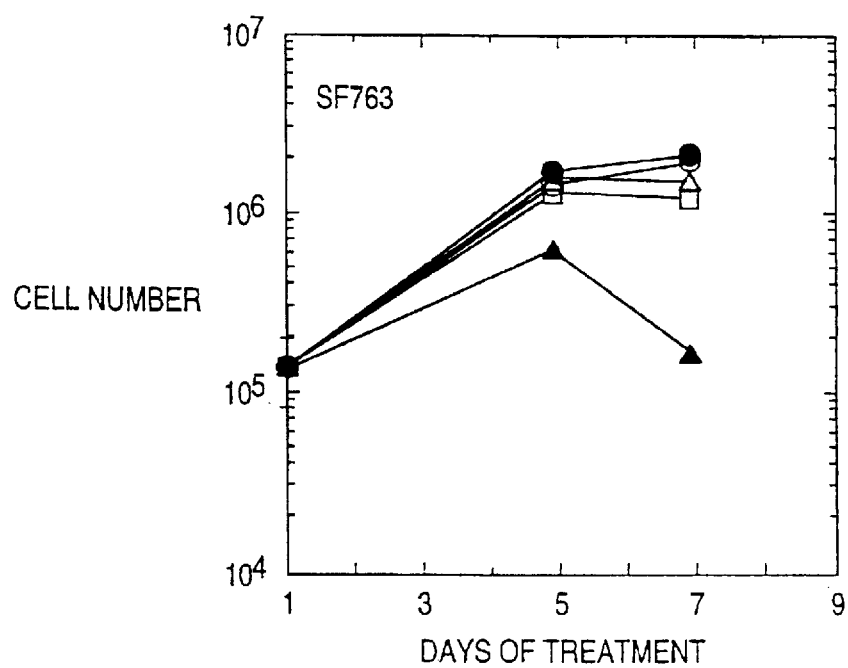
FIG. 14 depicts the blocking in SF763 cells of growth inhibitory effects of 10 μM BE-4-4-4-4 by polyamines added simultaneously with BE-4-4-4-4. Symbols and explanation set forth for FIG. 13 also pertain to this figure.

The simultaneous addition of naturally occurring polyamines blocked the growth inhibition by BE-4-4-4-4 in U-251 MG cells. See FIG. 13. Simultaneous addition of polyamines almost completely blocked growth inhibitory effects in SF-763 cells as well. See FIG. 14.

Cytotoxicity Assays

Cell survival was determined with a colony forming efficiency assay on the seventh day after drug treatment See Deen et al., *Int'l J. Rad. Oncol. Biol. Phys.* 5: 1663–67 (1979). Feeder numbers and optimal growth conditions for different cell lines were standardized separately.

Figure 15:
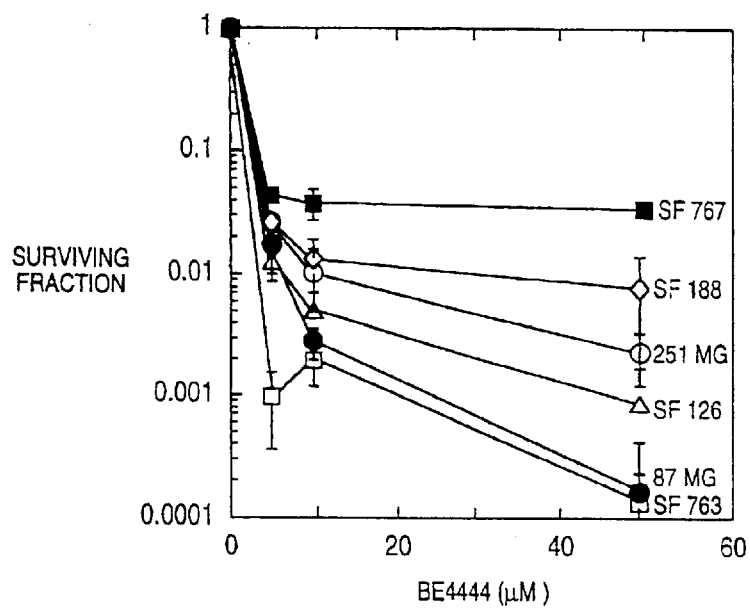
FIG. 15 depicts the effects of varying concentrations of BE-4-4-4-4 on the survival of U-87 MG (●), U-251 MG (○), SF-126 (Δ), SF-188 (◇), SF-763 (□), and SF-767 cells (■) on the seventh day of treatment as determined from the colony forming efficiency assay. Values are an average of the results of six separate experiments. Error bars, where not seen, are smaller than symbol size.

FIG. 15 shows that 5 μM BE-4-4-4-4 killed more than 90% of cells by the seventh day of treatment in all lines. In SF-767 and SF-188 cells, the dose response of survival reached a plateau at 10 μM. For the other cell lines, the surviving fraction continued to decrease even when 50 μM BE-4-4-4-4 was used. No data for DAOY cells is presented because none of these cells were attached to the flasks by the seventh day of treatment, and the floating cells present in the flask failed to attach to the surface and form viable colonies when harvested and replated with fresh medium. Floating cells from SF-126 and SF-763 cultures treated with 50 μM BE-4-4-4-4 for 6 days also failed to form viable colonies when re-seeded in fresh medium.

Polyamine Measurement

Approximately 5–10×$10^5$ cells of each cell line were collected and then washed twice with isotonic phosphate buffer (pH 7.4). Cells were sonicated in 250 μl of 8% sulfosalicylic acid and centrifuged. Then, 50–100 μl of the supernatant was dansylated and analyzed for polyamine content using high performance liquid chromatography as described by Kabra et al., *J. Chromatogr. Biomed. Appl.* 380: 19–32 (1986).

BE-4-4-4-4 uptake after 6 days of treatment varied among the cell lines from 3 to 35 nm/$10^6$ cells. The representative polyamine profiles for U-251 MG cells are presented in FIG. 16, and the data for other cell lines are summarized in FIG. 17. In all cell lines, treatment with 5 $\mu$M or more BE-4-4-4-4 depleted intracellular putrescine and spermidine to nondetectable or barely detectable levels after 4 days of treatment. Spermine levels were depleted to less than 40% of control after 6 days of treatment.

Cells were also examined after BE-4-4-4-4 treatment followed by treatment with polyamines. In SF-763 cells, intracellular levels of BE-4-4-4-4 were lower after treatment with BE-4-4-4-4 followed by polyamines than after treatment with BE-4-4-4-4 alone. See FIG. 18. In U-251 MG cells, the BE-4-4-4-4 level was also reduced by the addition of spermidine or spermine, but to a lesser extent. See FIG. 19.

In U-251 MG cells treated with putrescine or spermidine, the BE-4-4-4-4 level was significantly reduced only on the seventh day of treatment, but in spermine-treated cells, it was less than 50% of the control level by Day 5. In most cases after BE-4-4-4-4 treatment, addition of putrescine increased putrescine, spermidine, and spermine; addition of spermidine increased spermidine and spermine; and addition of spermine increased only spermine. These responses only partly correlated with polyamine-induced reversal of growth inhibition in some cell lines.

The levels of BE-4-4-4-4 were lower in both cell lines treated simultaneously with BE-4-4-4-4 (FIG. 20 for SF-763 and FIG. 21 for U-251 MG) and polyamines than in cells treated either with BE-4-4-4-4 alone (FIG. 17) or with polyamines 1 day after BE-4-4-4-4 (FIGS. 18 and 19). Polyamine levels in these cells changed similarly to those in reversal studies.

Results from the In Vitro Data

In most cell lines, growth inhibition by BE-4-4-4-4 had some correlation with drug uptake and a weak correlation with the ability of the analog to deplete cellular polyamines. For example, despite the much faster depletion of polyamines in SF-767 cells than in U-87 MG cells (FIG. 17), growth inhibition was more pronounced in U-87 MG cells (FIG. 3). Further, the intracellular BE-4-4-4-4 level was much higher in U-87 MG than in SF-763, and reversal of growth inhibition by polyamines also corresponded to differences in intracellular BE-4-4-4-4 levels. In SF-763, all three polyamines reduced BE-4-4-4-4 levels and reversed growth inhibition when added after BE-4-4-4-4 treatment, whereas in U-251 MG, all polyamines reduced BE-4-4-4-4 levels but only spermine reversed growth inhibition. Finally, simultaneous treatment with polyamines and BE-4-4-4-4 resulted in BE-4-4-4-4 levels much lower than in cells treated with BE-4-4-4-4 alone, but polyamine levels were still lower than those in control cells. This block of growth inhibition therefore appears to be related to prevention of an increase in BE-4-4-4-4 levels rather than to polyamine replenishment. Growth inhibition appears to be more closely related to BE-4-4-4-4 uptake than to reduced polyamine levels, although in no case was there growth inhibition without some measure of polyamine depletion.

In each cell line, BE-4-4-4-4 treatment resulted in uptake of the compound, polyamine depletion, and inhibition of cell growth. In five of the seven treated cell lines, cell growth reached a plateau with little or no cell loss, whereas in two (U-87 MG and DAOY), cell loss was evident.

The polyamine-induced reversal of growth inhibition seen after BE-4-4-4-4 treatment did not occur after BE-4-4-4 treatment, although both the uptake of external polyamines and the reduction of intracellular analog levels was comparable with the two analogs. Basu et al., *Biochem. J.* 269: 329–34 (1990). The reversal seen with BE-4-4-4-4 therefore indicates that a higher level of BE-4-4-4-4 than of BE-4-4-4 may be required to inhibit growth. The addition of polyamines would then lower the level of BE-4-4-4-4, but not that of BE-4-4-4 below their respective thresholds. These results strongly indicate that increases in intracellular analog concentrations are more important for growth inhibition than the depletion of polyamines. Additionally, the mechanism of growth inhibition by BE-4-4-4-4 differs from other known polyamine analogs.

In both U-251 MG and SF-763, simultaneous addition of polyamines and BE-4-4-4-4 resulted in lower BE-4-4-4-4 levels (FIGS. 20 and 21) than did addition of polyamines 1 day after BE-4-4-4-4 (FIGS. 18 and 19). This difference corresponds with similar findings with BE-4-4-4. Basu et al., *Int'l J. Cancer* 48: 873–78 (1991).

The appearance of spermidine and spermine in putrescine-treated cells and the appearance of spermine in spermidine-treated cells indicate that BE-4-4-4-4 does not appreciably affect the activities of spermidine and spermine synthetase in these cell lines. See FIGS. 18 and 19.

In SF-767 and SF-188, the cytotoxicity of BE-4-4-4-4 reached a plateau at 10 $\mu$M. See FIG. 15. Increases in BE-4-4-4-4 concentrations increased the intracellular BE-4-4-4-4 level only slightly in SF-188 and had almost no effect in SF-767. See FIG. 17. In the other cell lines, cytotoxicity continued to increase between 10 and 50 $\mu$M (FIG. 15), and in all but SF-126, increases in the concentration of added BE-4-4-4-4 continued to increase intracellular levels of the drug. Therefore, in most of these cell lines, the intracellular BE-4-4-4-4 level may be responsible for the degree of cytotoxicity as well as growth inhibition. In SF-126, however, cytotoxicity increased with no detectable increase in the intracellular BE-4-4-4-4 concentration. Depletion of intracellular polyamines may account for the additional toxicity in this cell line. Because of the large amount of cell kill in DAOY cells, no correlation was possible between cytotoxicity and intracellular levels of polyamines or analogs. It should also be noted that by day 7 of treatment, 10 and 50 $\mu$M of BE-4-4-4-4 had killed about 2 log of SF-188 cells. This cell line is relatively resistant to BE-4-4-4 and other cytotoxic agents such as BCNU. See Basu et al., *Int'l J. Cancer* 48: 873–78 (1991).

The in vitro data suggests that polyamine analogs with hydrocarbon chain lengths different from those of natural polyamines, such as BE-4-4-4-4, can inhibit growth if they are taken up by cells and have an affinity for DNA high enough to displace bound polyamines from DNA. An analog having a very high affinity for DNA may inhibit growth even if it is a better aggregator of DNA than other cytotoxic polyamine analogs. Experiments with other spermine analogs corroborate this observation. Feuerstein et al., *J. Cell. Biochem.* 46: 37–47 (1991); Basu et al., *Biochem. J.* 269: 329–44 (1990); Edwards et al., *J. Med. Chem.* 33: 1369–75 (1990); Bowlin et al., *Cancer Res.* 51: 62–66 (1991); Ohida et al., *Mol. Pharm.* 42: 302–06 (1992).

EXAMPLE 3. COMPARISON OF BE-4-4-4-4 TO OTHER POLYAMINES

Growth Inhibition

Figure 22A:
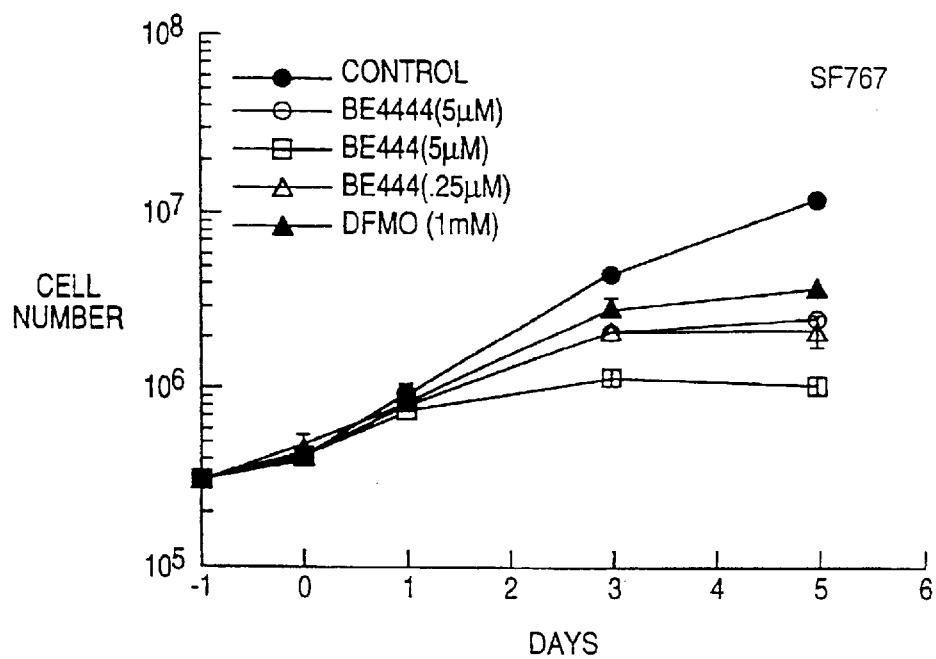
FIG. 22 depicts data from standardized studies of the effects of BE-4-4-4-4, BE-4-4-4 and DFMO on growth of SF-767 cells (top graph) and U-251 MG (bottom graph) in human brain tumor cells. Values are the average of 3 separate experiments. Error bars, where not visible, are smaller than symbol size.
Figure 22B:
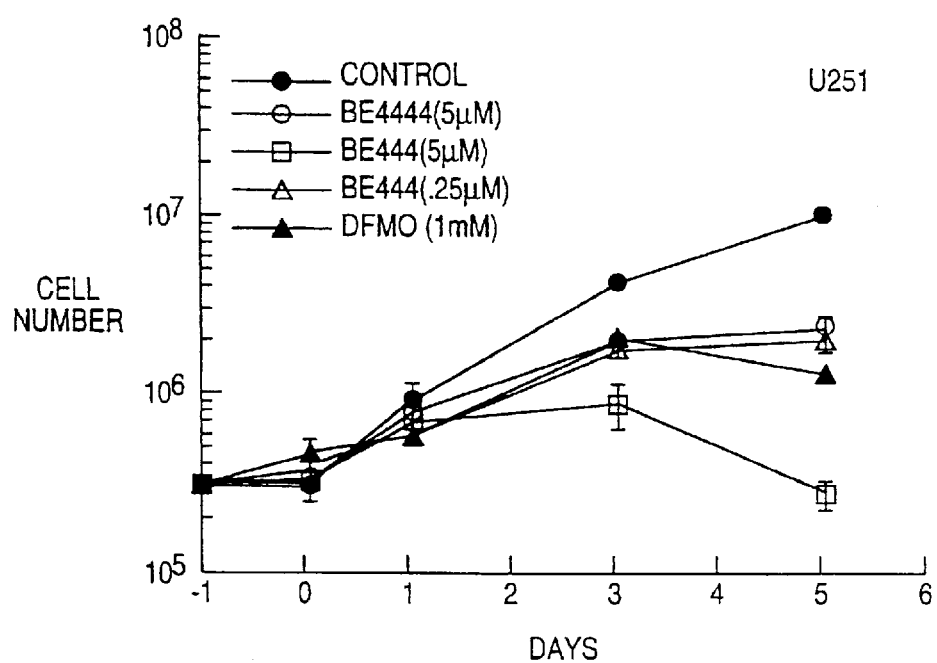

FIG. 22 depicts data from standardized studies of the effects of BE-4-4-4-4, BE-4-4-4 and DFMO on growth of U-251 MG and SF-767 cells.

Growth inhibition was apparent 3 days after addition of these compounds. Thereafter, little growth occurred in treated cells. In both cell lines, 5 $\mu$M BE-4-4-4 was more potent than 5 $\mu$M BE-4-4-4-4 in inhibiting growth. U-251 MG cultures treated with BE-4-4-4 lost cells between days 3 and 5, while SF-767 cultures did not. In both cell lines, 5 $\mu$M BE-4-4-4-4, 0.25 $\mu$M BE-4-4-4, and 1 mM DFMO inhibited growth comparably.

Cell Survival

Figure 23A:
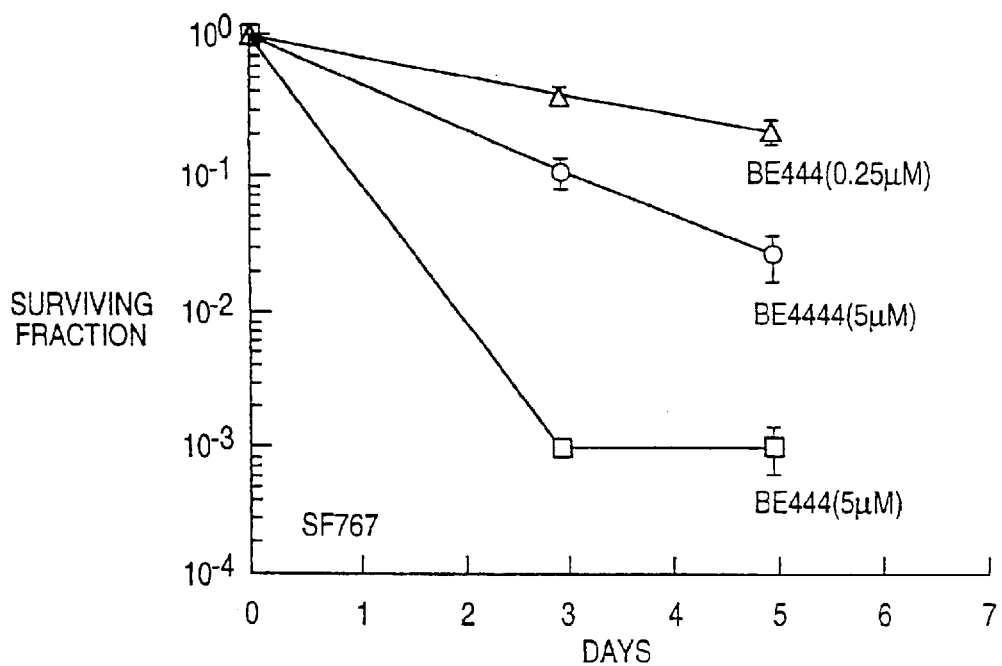
FIG. 23 depicts data from standardized studies of the survival of SF-767 cells (top graph) and U-251 MG (bottom graph) on the third and fifth days of treatment with BE-4-4-4-4 or BE-4-4-4. Values without an asterisk are the average of 3 separate experiments. Values with an asterisk are an average of 2 separate experiments.
Figure 23B:
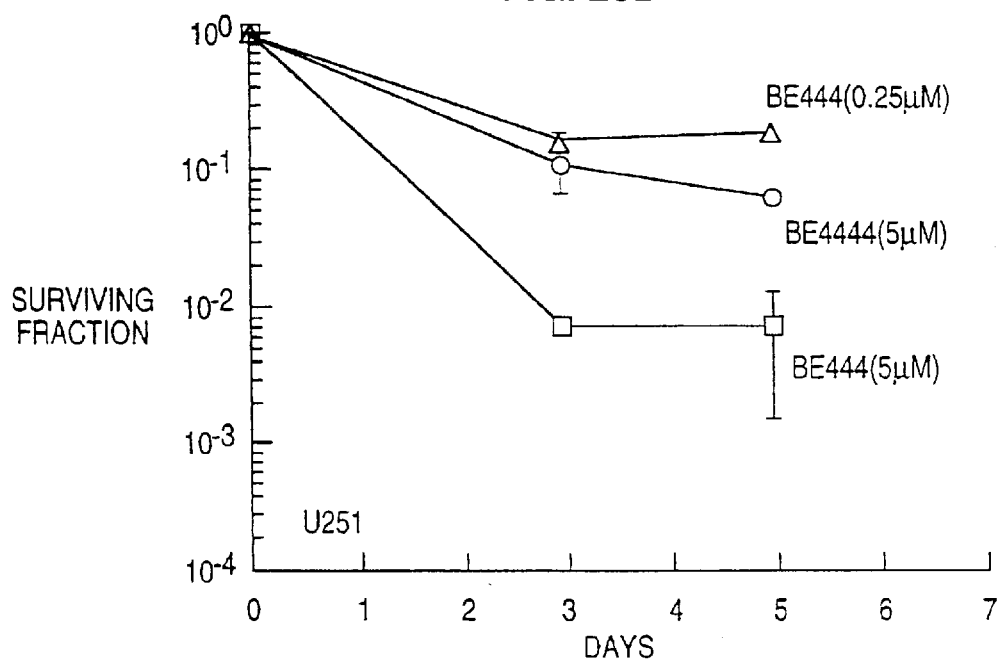

FIG. 23 depicts the surviving fractions of SF-767 and U-251 MG as a function of treatment time. In both cell lines, 0.25 $\mu$M BE-4-4-4 was less toxic than 5 $\mu$M BE-4-4-4-4, and 5 $\mu$M BE-4-4-4 was more toxic than 5 $\mu$M BE-4-4-4-4. 5 $\mu$M BE-4-4-4 was more toxic to SF-767 than to U-251 MG.

Polyamine Levels

FIGS. 24 and 25 depict polyamine and polyamine analog levels in control and treated cells. Putrescine and spermidine levels were relatively lower in control SF-767 cells than in control U-251 MG cells. In both cell lines, 24 hours of treatment with 5 $\mu$M BE-4-4-4-4 or 5 $\mu$M BE-4-4-4 decreased putrescine and spermidine levels. By Day 3, putrescine and spermidine were undetectable in both lines. Spermine levels were decreased by 5 $\mu$M BE-4-4-4-4 or 5 $\mu$M BE-4-4-4 in both cell lines, but not to undetectable levels. At a concentration of 0.25 $\mu$M, BE-4-4-4 had less effect on polyamine levels in either cell line.

In SF-767 cells, uptake of BE-4-4-4 and BE-4-4-4-4 reached a plateau 1 day after treatment. In U-251 MG cells, uptake of 5 $\mu$M BE-4-4-4 varied during the course of the experiment, whereas uptake of 0.25 $\mu$M BE-4-4-4 increased to a maximum near Day 1 and then decreased. BE-4-4-4-4 levels reached a plateau after 1 day of treatment.

Cell Cycle

Figure 26A:
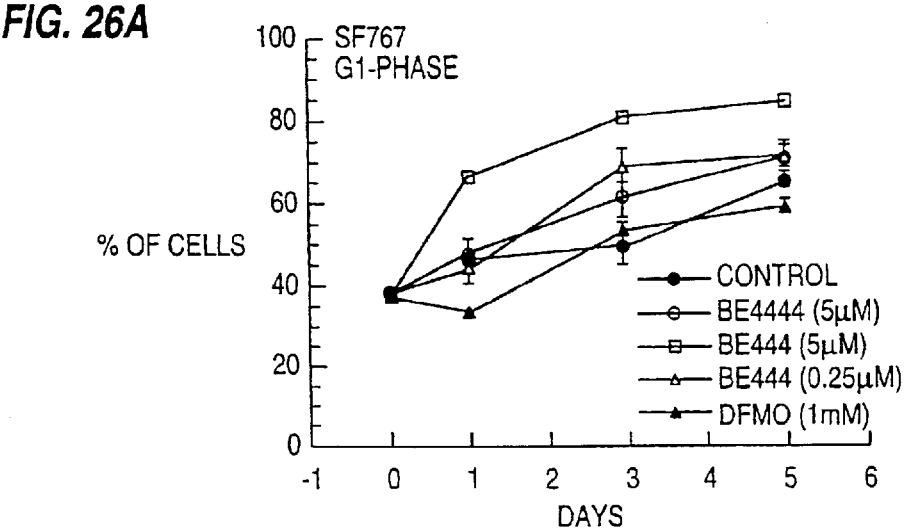
FIG. 26 depicts the cell cycle effects of BE-4-4-4, BE-4-4-4-4 or DFMO on SF-767 cells. Values with error bars are based on the average of 3 separate experiments. Value without error bars are based on an average of 2 separate experiments.
Figure 26B:
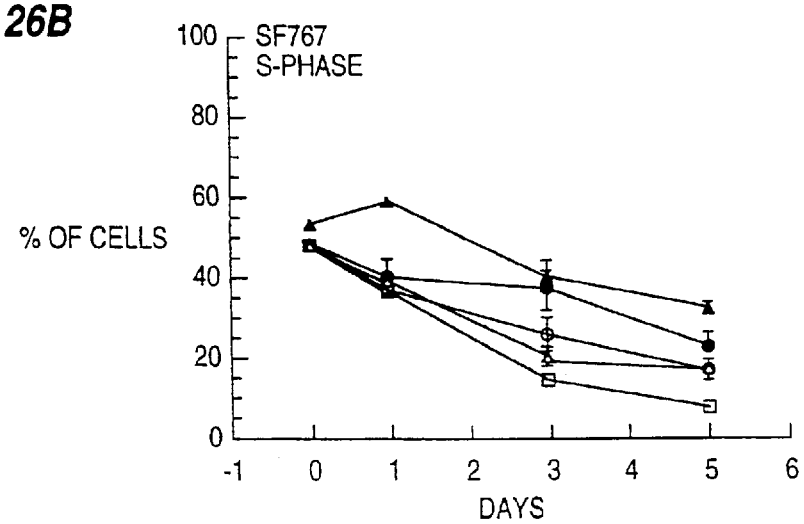
Figure 26C:
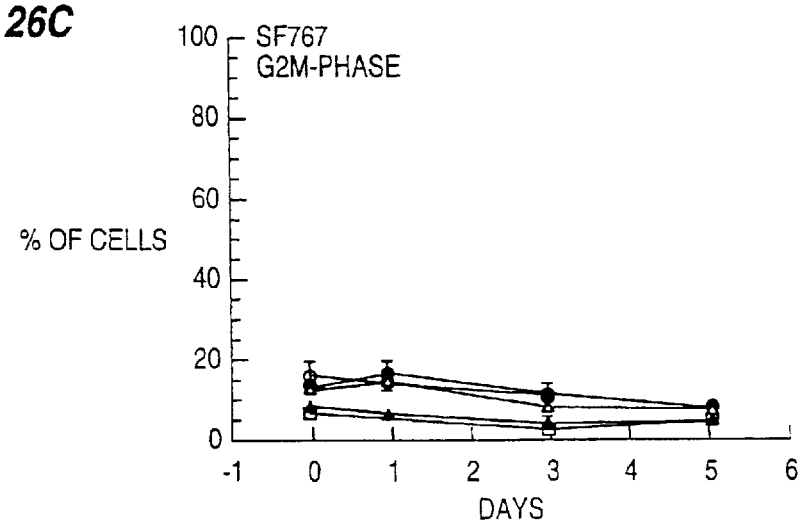
Figure 27A:
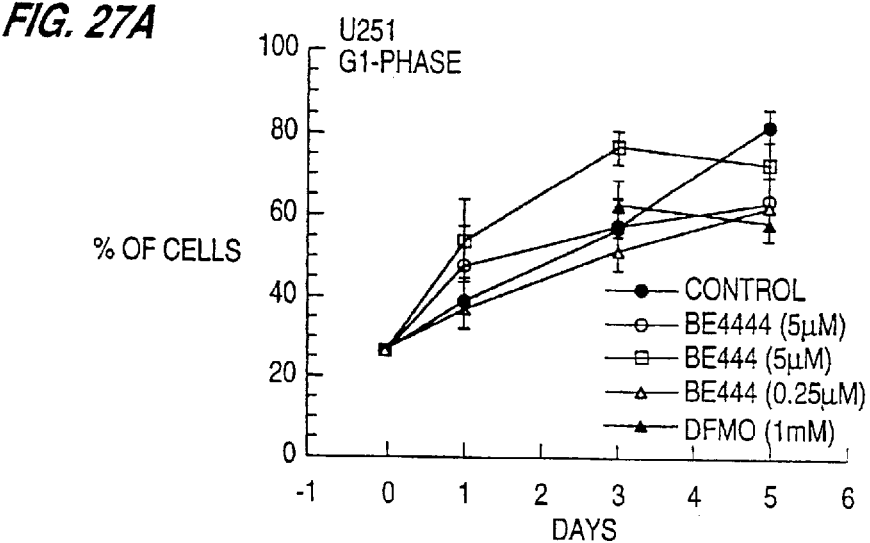
FIG. 27 depicts the cell cycle effects of BE-4-4-4, BE-4-4-4-4 or DFMO on U-251 MG cells. Values with error bars are based on the average of 3 separate experiments. Value without error bars are based on an average of 2 separate experiments.
Figure 27B:
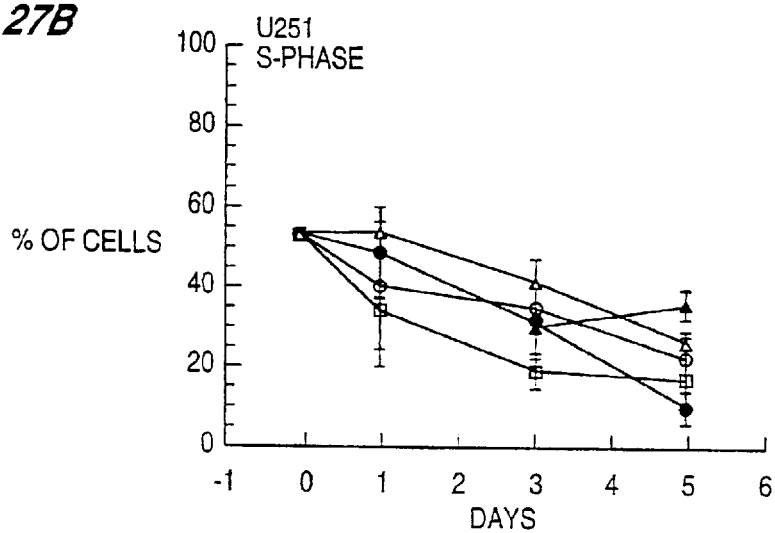
Figure 27C:
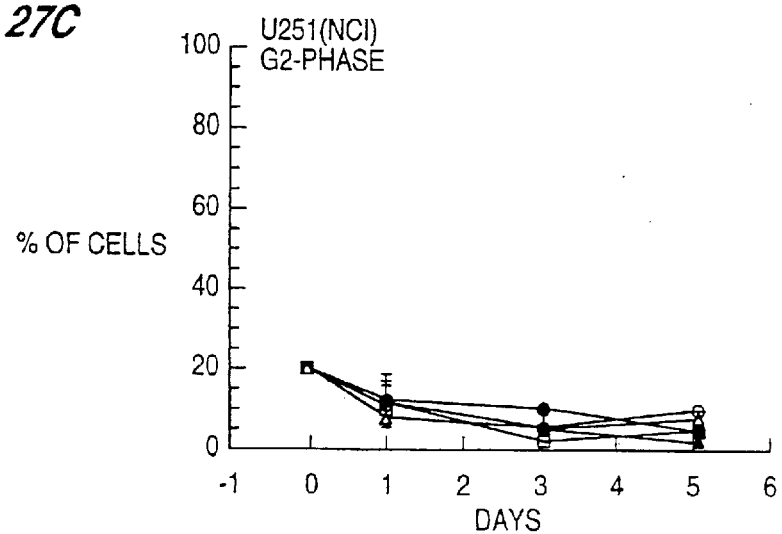

FIGS. 26 and 27 depict the effects of drug treatment on the fractions of cells in the $G_1$, S, and $G_2$/M phases over time. In SF-767 cultures, 5 $\mu$M BE-4-4-4-4 and 0.25 $\mu$M BE-4-4-4 had similar effects on the cell cycle. The number of $G_1$-phase cells increased and reached a maximum by the third day of treatment. This increase corresponded to a decrease in the S-phase fraction. There was no detectable change in the fraction of $G_2$/M-phase cells. Treatment with 5 $\mu$M BE-4-4-4 accentuated these effects, and also resulted in a small decrease in the $G_2$/M fraction. DFMO caused a slight decrease in the $G_2$/M fraction and a slight increase in the S-phase fraction.

In U-251 MG cultures, 5 $\mu$M BE-4-4-4-4 and 0.25 $\mu$M BE-4-4-4 had no effect on the cell cycle. Five micromolar BE-4-4-4 increased the $G_1$ fraction and decreased the S-phase fraction between 1 and 5 days of treatment. The high percentage of cells in $G_1$ on Day 5 in control cells probably occurred because the culture had reached confluence. DFMO had no effect on the cell cycle in U-251 MG cultures.

These findings provide further support for the view that polyamine depletion alone is not primarily responsible for alterations in cell cycle, survival, and growth produced in SF-767 and U-251 MG human brain tumor cell lines by the polyamine analogs BE-4-4-4-4 and BE-4-4-4. See Ghoda et al., *Mol. Pharmacol.* 42: 302–06 (1992). This conclusion is based largely upon comparisons between patterns of polyamine depletion and patterns of cell cycle, survival, and growth in cells treated with polyamine analogs. It is also supported by evidence that the presence of polyamine analogs, not simple polyamine depletion, directly inhibits the growth of CHO cells and various brain tumor cell lines. Basu et al., *Cancer Res.* 50: 3137–40 (1990); Basu et al., *Cancer Res.* 49: 5591–97 (1989); Basu et al., *Cancer Res.* 53: 3948–55 (1993); Basu et al., *Biochem. J.* 282: 723–27 (1992); Ghoda et al., supra.

In regard to the effects of BE-4-4-4 and BE-4-4-4-4 on the cell cycle, the observed $G_1$/S cell cycle block in SF-767 and U-251 MG cells treated with 5 $\mu$M BE-4-4-4 is consistent with data in other tumor cell lines showing that both BE-4-4-4 and DFMO produce a $G_1$/S block, although other patterns of cell cycle progression have been reported with DFMO. In the analog-treated, polyamine-depleted cells, the relationship between polyamine depletion and cell cycle progression reported for DFMO was not observed. Both 5 $\mu$M BE-4-4-4 and 5 $\mu$M BE-4-4-4-4 depleted putrescine, spermidine, and spermine in U-251 MG and SF-767 with nearly identical kinetics. Five micromolar BE-4-4-4 blocked both SF-767 and U-251 MG at the $G_1$/S border, while 5 $\mu$M BE-4-4-4-4 blocked each line much less or not at all (FIGS. 26 and 27). Moreover, 0.25 $\mu$M BE-4-4-4 decreased putrescine and spermidine only slightly compared with control, but caused an accumulation of $G_1$ phase cells. Thus, the very similar patterns of polyamine depletion produced by 5 $\mu$M BE-4-4-4 and 5 $\mu$M BE-4-4-4-4 did not lead to similar cell cycle effects, and the very different patterns of polyamine depletion produced by 0.25 $\mu$M BE-4-4-4 and 5 $\mu$M BE-4-4-4-4 led to very similar alterations in cell cycle progression. This is strong evidence that polyamine depletion associated with BE-4-4-4 and BE-4-4-4-4 is not directly linked to cell cycle progression.

Polyamine depletion also did not correlate with growth inhibition or with survival in either cell line studied. Although 5 $\mu$M BE-4-4-4 and 5 $\mu$M BE-4-4-4-4 produced similar kinetics and magnitudes of polyamine depletion in SF-767 and U-251 MG cells, the former treatment inhibited growth and was more cytotoxic than the latter. Furthermore, although 5 $\mu$M BE-4-4-4-4 and 0.25 $\mu$m BE-4-4-4 differed in their ability to deplete polyamines, they induced only small differences in growth or survival of SF-767 or U-251 MG cells.

The alterations in cell cycle progression, however, did correlate with growth inhibition and with survival in both cell lines. Five micromolar BE-4-4-4 induced a $G_1$/S block in both cell lines while 5 $\mu$m BE-4-4-4-4 and 0.25 $\mu$m BE-4-4-4 did not; and 5 $\mu$m BE-4-4-4 had more growth inhibitory and cell killing activity than either of the other treatments.

In view of the above, it is clear that depletion of natural polyamines is not the cytotoxic mechanism of the polyamine analogs of the present invention. Rather, it is apparent that the polyamine analogs of the present invention bind to the physiologic sites that usually mediate polyamine-dependent growth, but do not allow these sites to actually mediate growth.

As explained above, the natural polyamines bind to and change the conformation of the DNA. The polyamine analogs also bind DNA, thereby displacing the natural polyamines, but do not effect the conformational changes needed to promote growth.

One possible way of altering the effects of polyamines on DNA is to change polyamine binding to DNA. Thus, altering hydrocarbon length of the polyamines can affect their binding to DNA and their ability to cause DNA conformational changes. In order to prevent the conformational changes needed to support growth, a polyamine analog could have a hydrocarbon length that is different than natural polyamines. Thus, the functions of the natural polyamines were targeted for pharmacologic intervention. Based on this criteria, BE-4-4-4-4 was developed for further study. A complete understanding of the mode operation of the polyamines and polyamine analogs is not necessary for the practice of the present invention, however.

EXAMPLE 4 IN VIVO ANIMAL STUDIES ON BE-4-4-4-4

Animal studies were undertaken with BE-4-4-4-4 to test its in vivo properties.

Toxicity Studies

Before in vivo efficacy studies were conducted, a BE-4-4-4-4 toxicity study was performed in mice in order to ascertain the effects of various dosages and administration regimens.

Figure 28:
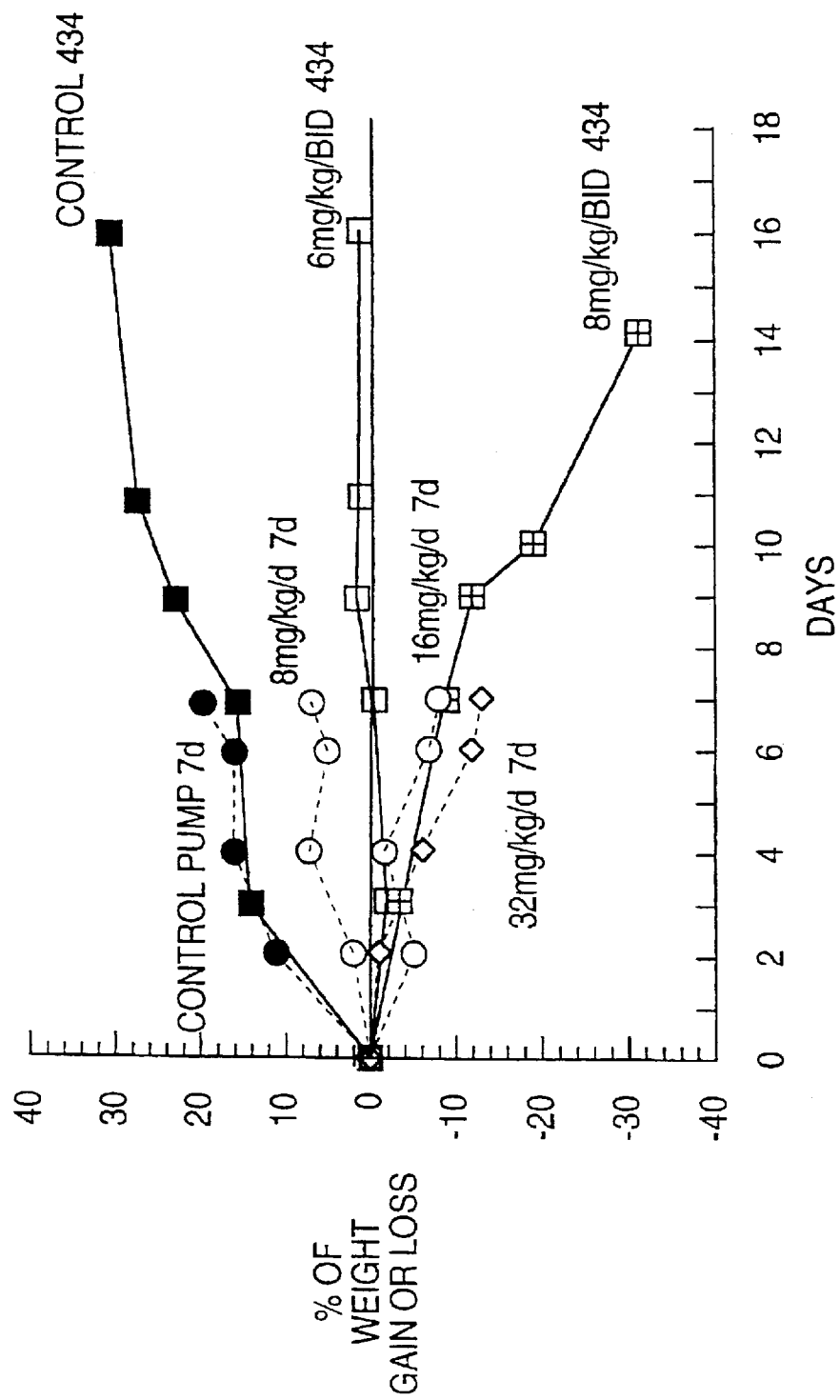
FIG. 28 depicts the effect of 0 (■), 6 (□), and 8 (+) mg/kg b.i.d. of BE-4-4-4-4 for a cycle of 4 days on, 3 days off, and 4 days on ("434" or "4/3/4") on the weight of nude mice with U-251 MG tumors. The effect of 0 (●), 8 (○), 16 (◉), 32 (◇) mg/kg of BE-4-4-4-4 for 7 days of continuous infusion on the weight of the nude mice with U-251 MG tumors is also shown. The values are an average of results in three mice and are expressed in percent of initial weight.
Figure 29B:
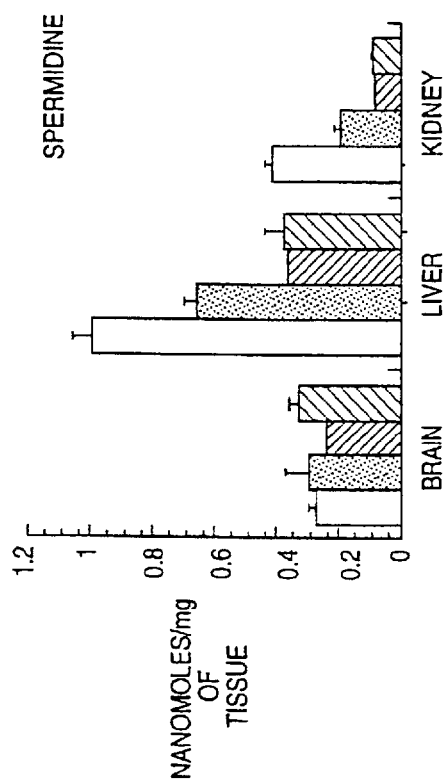
FIG. 29 depicts levels of natural polyamines and BE-4-4-4-4 after treatment with a continuous infusion of BE-4-4-4-4 for 7 days. The depicted values are an average of the results for three different mice. Error bars represent standard deviations. No data are shown for levels which were not detectable.
Figure 29D:
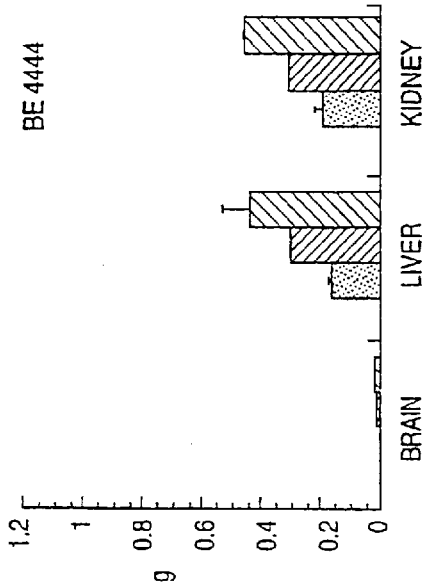
Figure 29A:
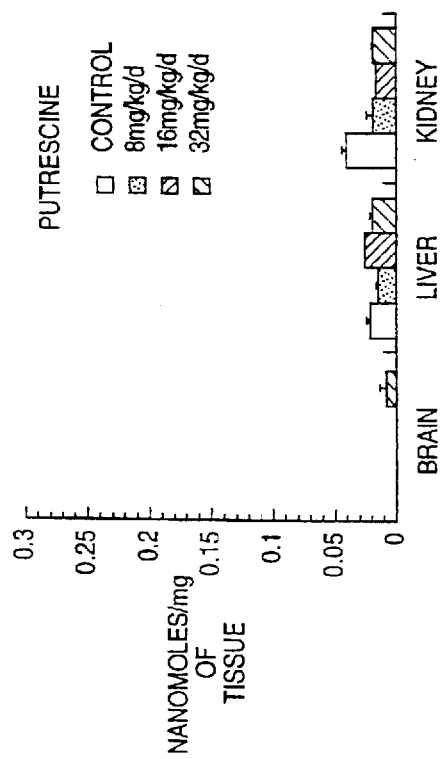
Figure 29C:
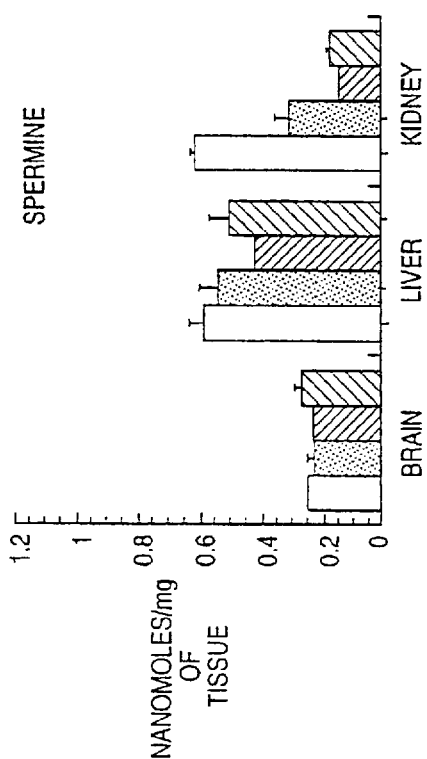
Figure 30A:
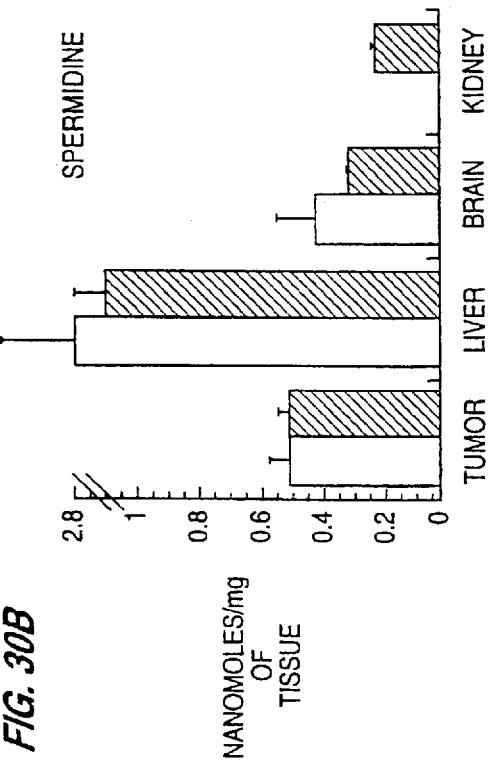
FIG. 30 depicts levels of natural polyamines and BE-4-4-4-4 in nude mice bearing U-251 MG tumors after treatment with 4 mg/kg b.i.d. of BE-4-4-4-4 for 4 days. The depicted values are an average of the results for three different mice. Error bars represent standard deviations. Asterisks represents measurements not taken. No data are shown for levels which were not detectable.
Figure 30B:
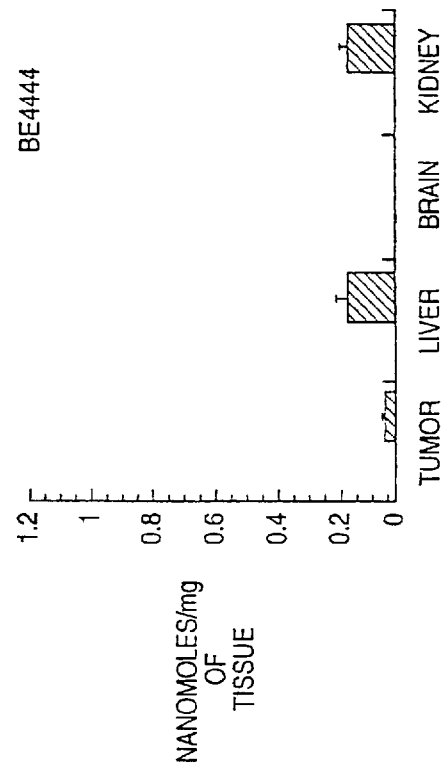
Figure 30C:
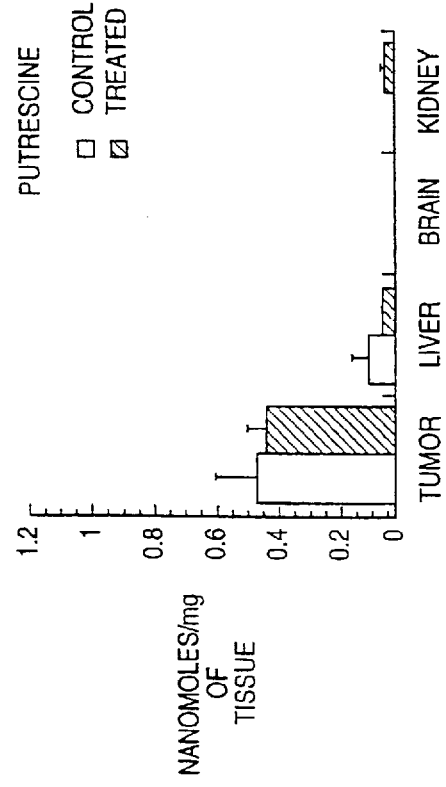
Figure 30D:
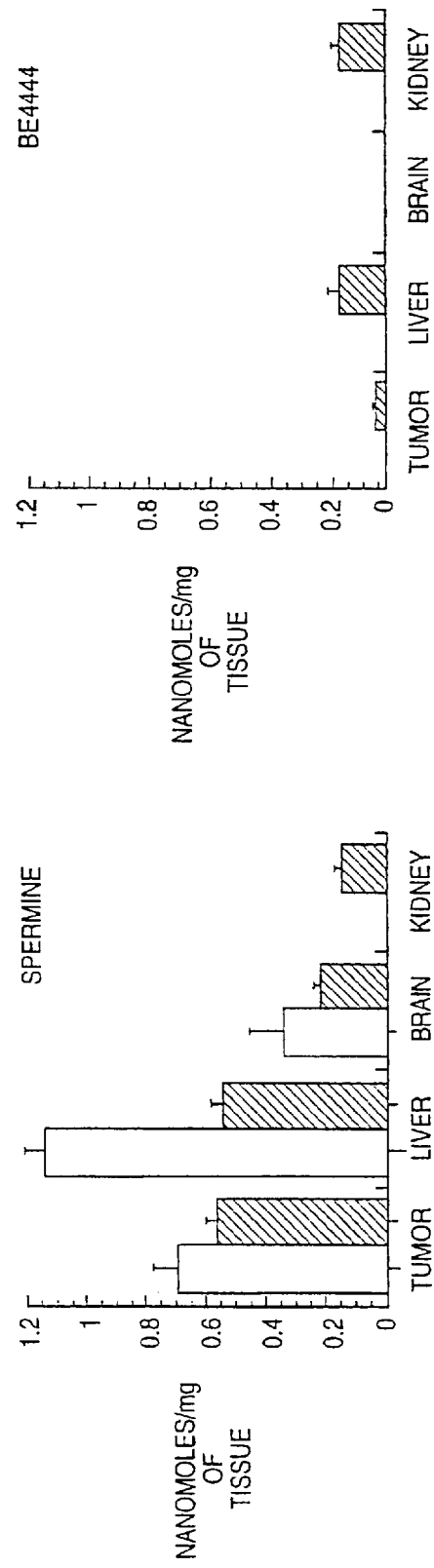

A single dose of 50 mg/kg of BE-4-4-4-4 killed the mice in 4 days. The mice died more quickly after larger single doses. The results of several continuous infusion experiments and b.i.d. dosing experiments are plotted in FIG. 28. As the dose of BE-4-4-4-4 increased, weight gain generally decreased.

Controls gained considerable weight (more than 20% of their original body weight) over 2 weeks, and mice given a 7-day continuous 8 mg/kg/day infusion gained considerably less (less than 10% of their original body weight). Mice given 6 mg/kg b.i.d. on a 4/3/4 schedule did not gain or lose weight. At higher doses, there appeared to be nearly equivalent weight loss. At 7 days, all mice lost approximately 10% of their body weight. A 7-day continuous 16 mg/kg/day infusion did not differ from an 8 mg/kg b.i.d. 4/3/4 schedule or from a 7-day continuous 32 mg/kg/day infusion.

Based on the above data, the 6 mg/kg b.i.d. using the 4/3/4 schedule, the regimen in which weight was generally constant, was selected for primary use in many of the efficacy studies. See, for example, FIG. 31.

Effect of BE-4-4-4-4 on Levels of Natural Polyamines

In mice given continuous infusions of BE-4-4-4-4 for 7 days, the level of the drug in various tissues and organs was a direct function of dose. FIG. 29 shows that brain levels were much lower than liver or kidney levels. Putrescine concentration was very low in all three tissues. Spermidine levels in liver and kidney decreased by over 50% when the mice were given 16 mg/kg/day of BE-4-4-4-4, but were not altered in brain. Increasing the dose to 32 mg/kg/day did not further decrease spermidine levels. Spermine levels also decreased in kidney after 8 and 16 mg/kg/day of BE-4-4-4-4, however, treatment with 32 mg/kg/day did not cause further decreases. Spermine concentrations in both brain and liver did not respond to any of these BE-4-4-4-4 treatments.

Effect of BE-4-4-4-4 on Levels of Natural Polyamines in Nude Mice bearing U-251 MG Tumors BE-4-4-4-4 levels in liver, kidney, and brain were similar in tumor-bearing mice treated with 4 mg/kg b.i.d. for 4 days (FIG. 30) and mice without tumors treated with the 7-day continuous 8-mg/kg/day infusion (FIG. 29). Control levels of putrescine, spermidine, and spermine were higher in mice with tumors than in mice without tumors. BE-4-4-4-4 had no effect on polyamine levels in tumor or brain, but lowered spermidine and spermine levels in liver.

Antitumor Activity of BE-4-4-4-4

Figure 31A:
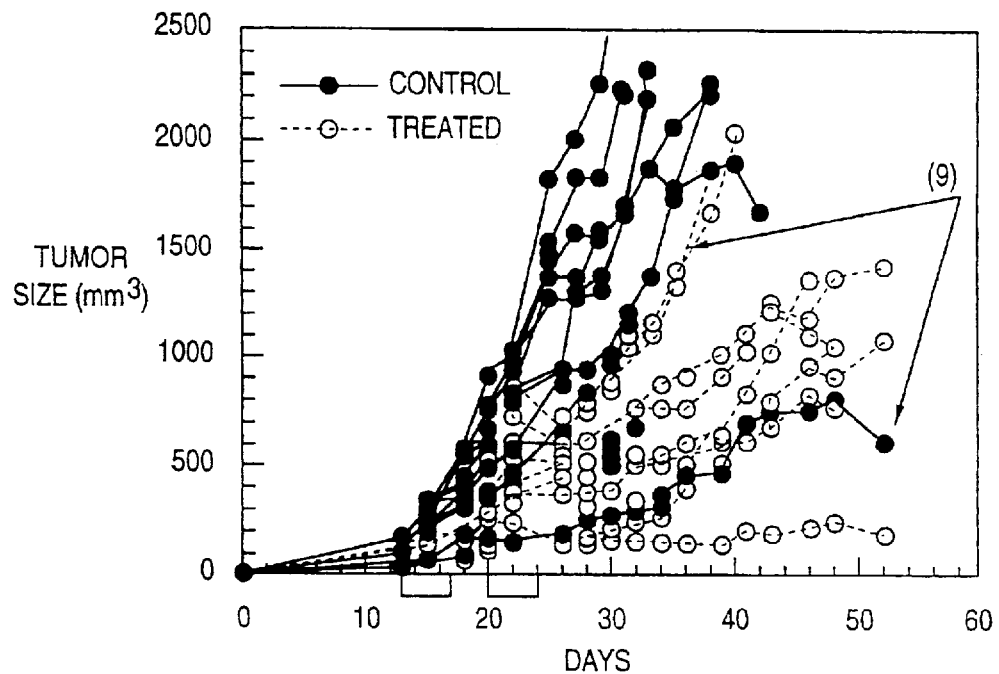
FIG. 31 depicts the growth inhibitory effect of 6 mg/kg b.i.d. on the 4/3/4 regimen in nude mice bearing U-251 MG tumors. The top graph plots tumor sizes for all of the pairs. The bottom graph plots average tumor sizes of the pairs. The numbers in parentheses refer to the number of mice measured at a particular time. Bars along the abscissa represent the periods of therapy.
Figure 31B:
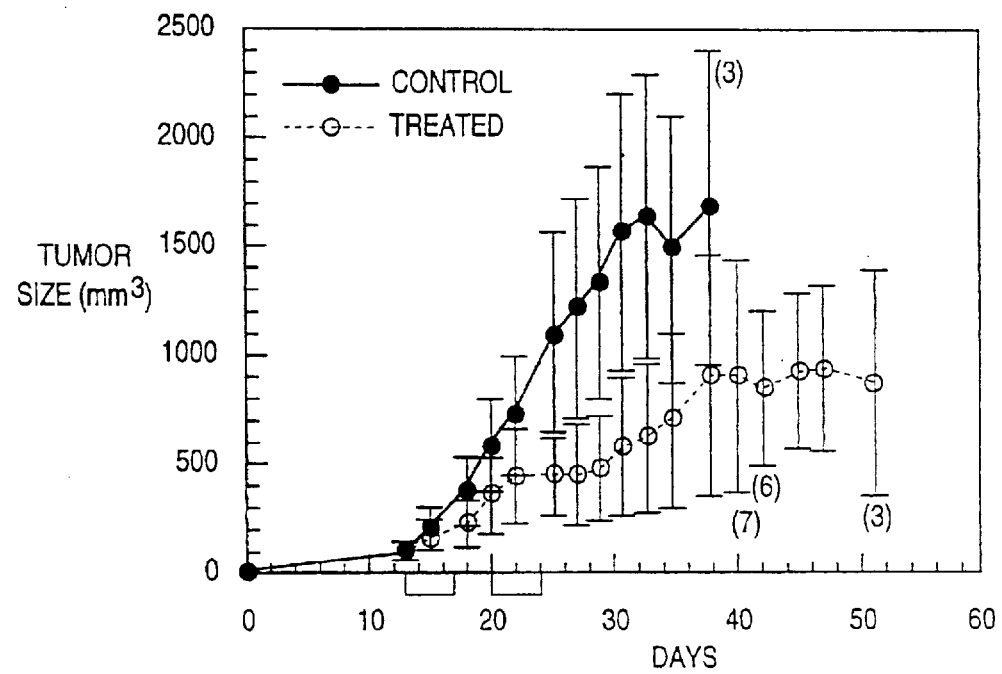
Figure 33A:
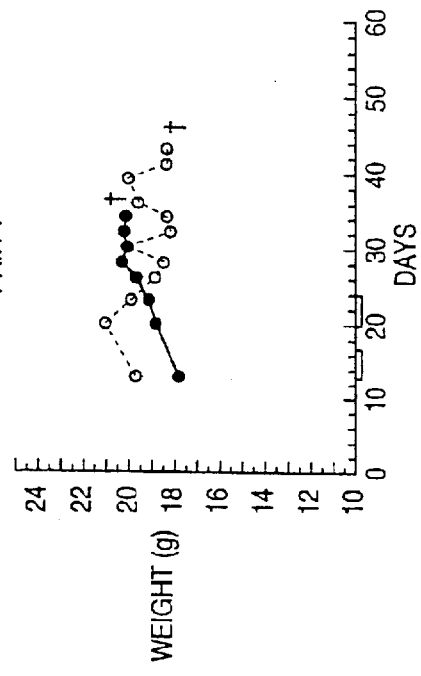
FIG. 33 depicts body weight as a function of time in the four pairs of nude mice that were the subject of FIG. 31. The mice were treated with 6 mg/kg b.i.d. of BE-4-4-4-4 in the 4/3/4 regimen. Crosses represent the day of death. Bars along the abscissa represent periods of therapy.
Figure 33C:
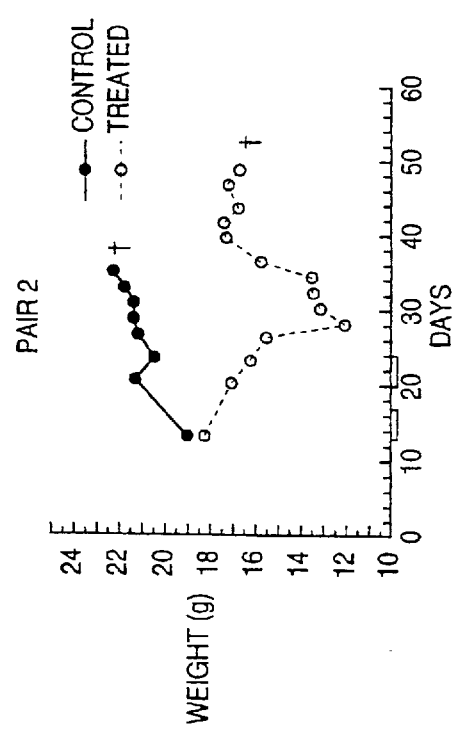
Figure 33B:
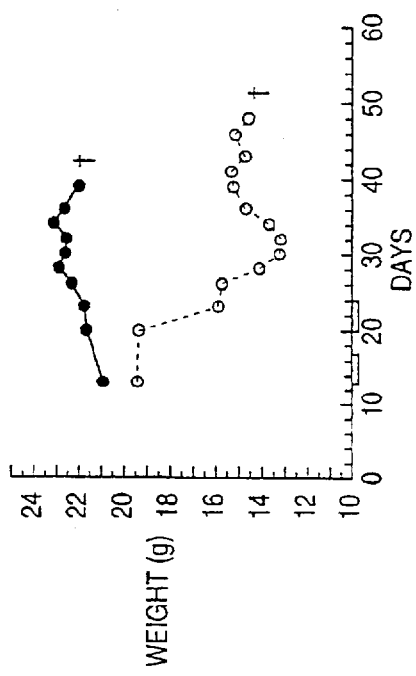
Figure 33D:
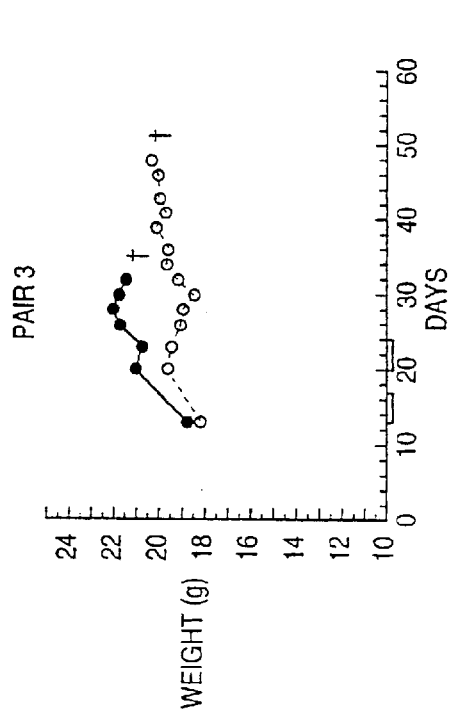

In nine of the ten pairs of mice with U-251 MG glioblastoma xenografts, tumor grew slower in the mouse treated with 6 mg/kg b.i.d. BE-4-4-4-4 on the 4/3/4 schedule than in the control mouse (FIG. 31). In each of the four representative pairs of mice shown in FIG. 32, the growth of treated tumors was delayed after drug treatment. Growth resumed after a variable time period (range: Day 26 to Day 40). This effect was observed in all but one pair of mice (FIG. 31).

Figure 34:
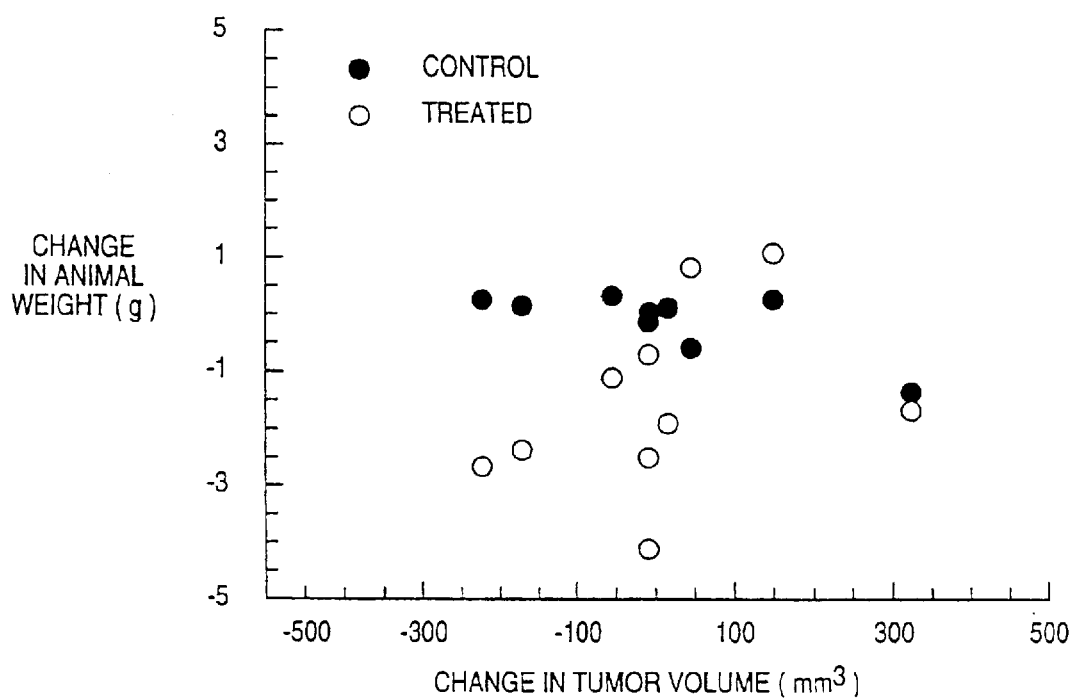
FIG. 34 is a scatter-plot of the changes in tumor volume and weight between days 26 and 30 in tumor-bearing mice treated with BE-4-4-4-4. Tumor volume and animal weight did not correlate in the tumor-bearing mice or the control mice.
Figure 16A:
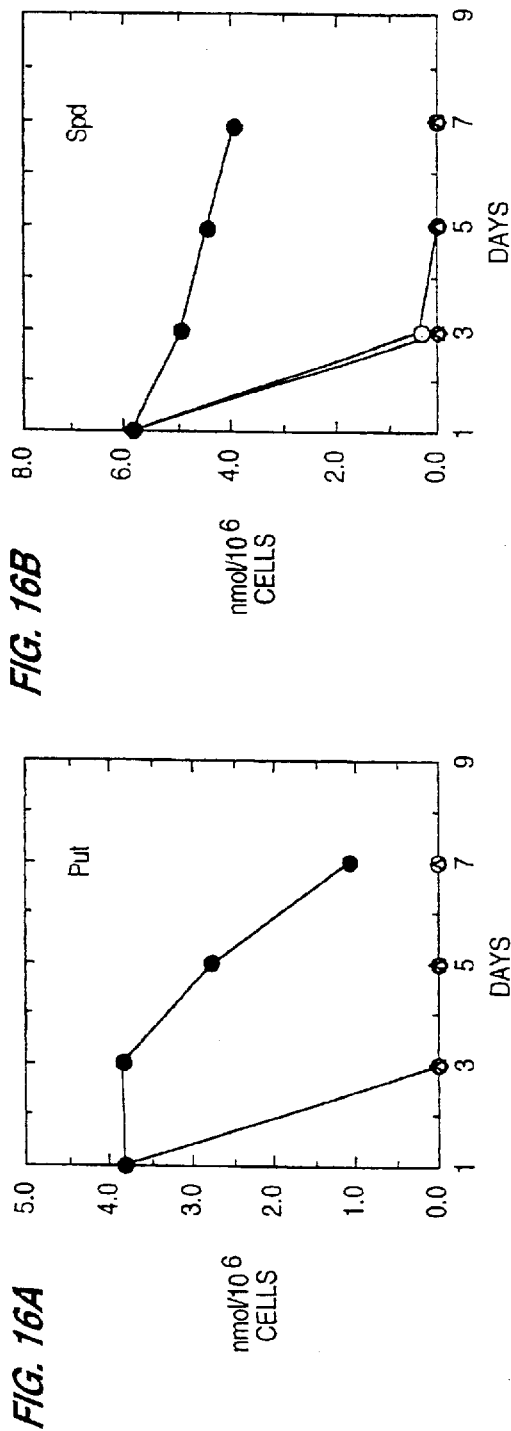
FIG. 16 depicts the polyamine levels of U-251 MG cells treated with 0 (●), 5 (○), 10 (Δ), and 50 μM BE-4-4-4-4 (◇). "Put" means putrescine; "Spd" means spermidine and "Spm" means spermine in this figure and the figures which follow. Values are based on an average of two determinations.
Figure 16B:
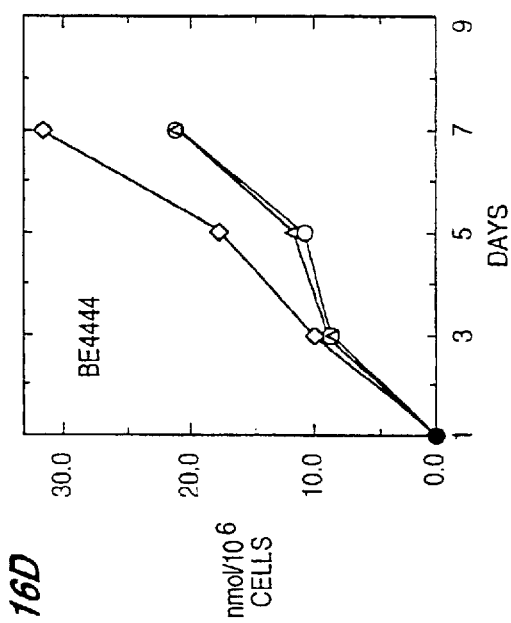
Figure 16C:
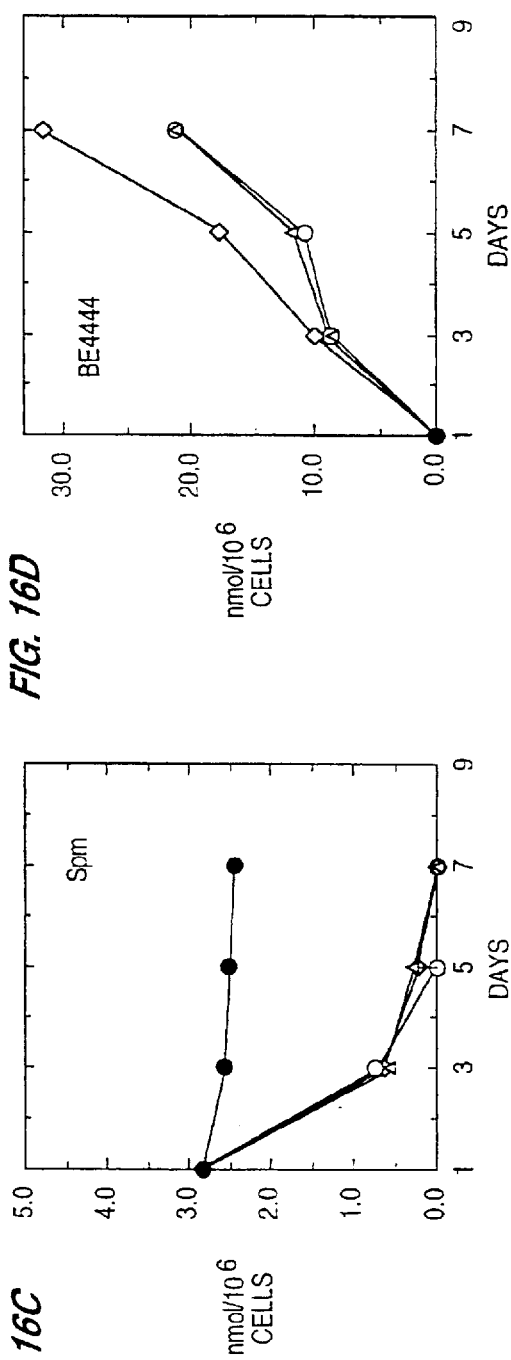
Figure 16D:
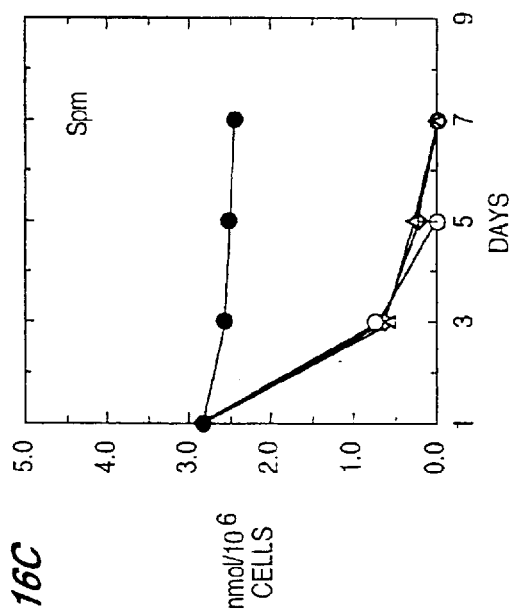
Figure 18B:
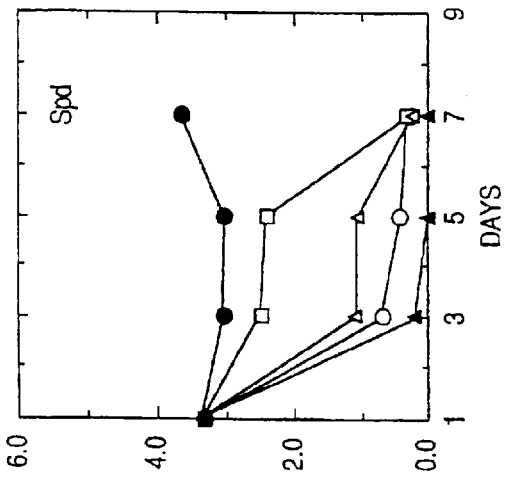
FIG. 18 depicts polyamine levels of SF-763 cells treated with 10 μM BE-4-4-4-4 and polyamines. Control (●), BE-4-4-4-4 (▲), BE-4-4-4-4+1 mM putrescine (Δ), BE-4-4-4-4+20 μM spermidine (□), BE-4-4-4-4+20 μM spermine (○). Values are based on an average of two determinations. Polyamines were added 24 hours after BE-4-4-4-4 addition.
Figure 18D:
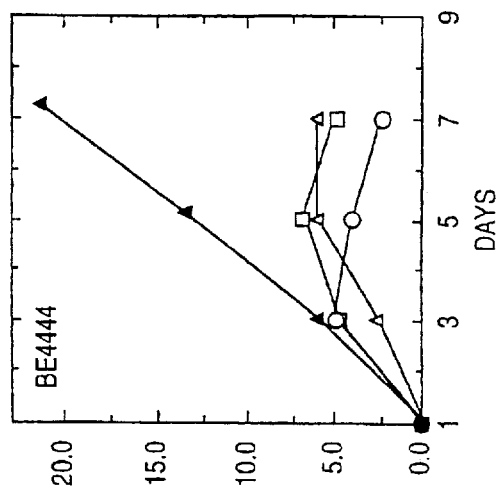
Figure 18A:
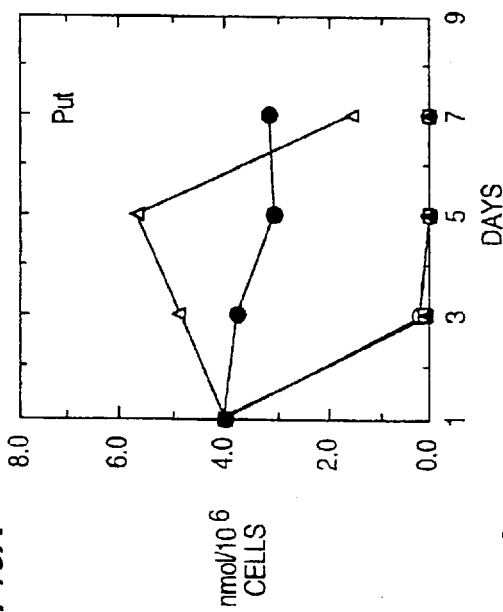
Figure 18C:
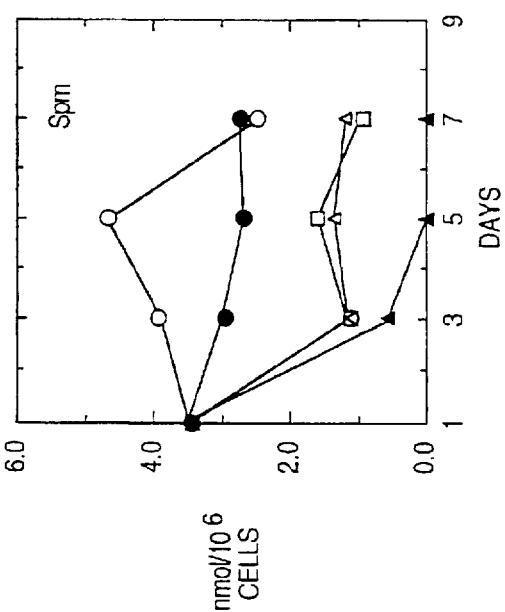
Figure 19A:
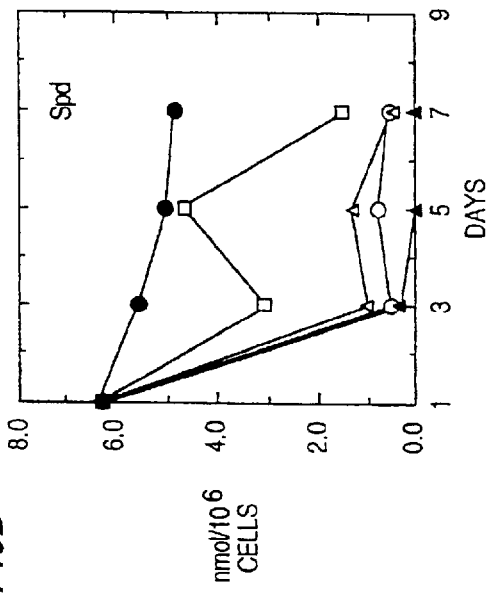
FIG. 19 depicts polyamine levels of U-251 cells treated with 10 μM BE-4-4-4-4 and polyamines. Symbols and explanation set forth for FIG. 18 also pertain to this figure.
Figure 19B:
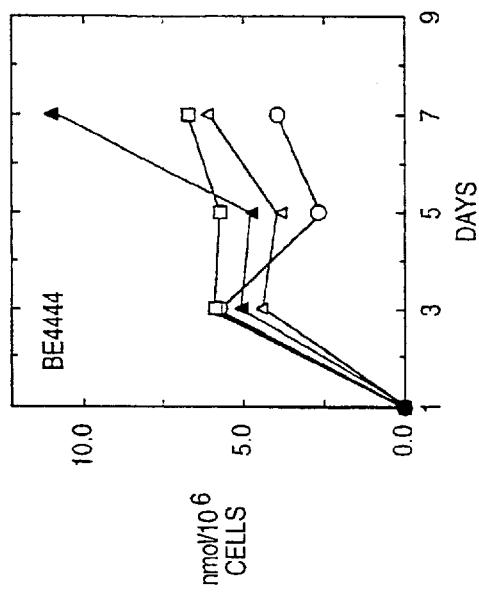
Figure 19C:
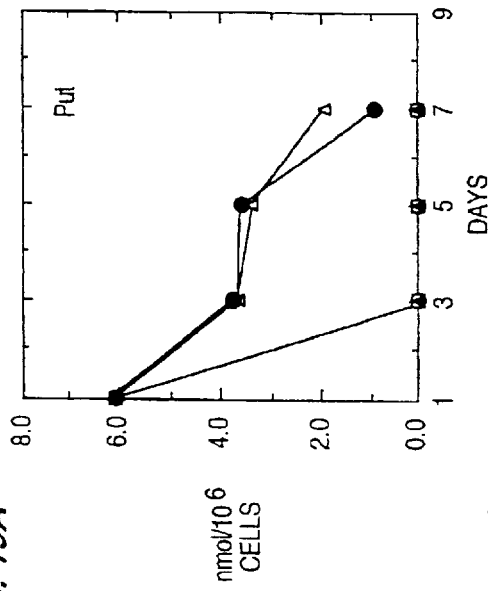
Figure 19D:
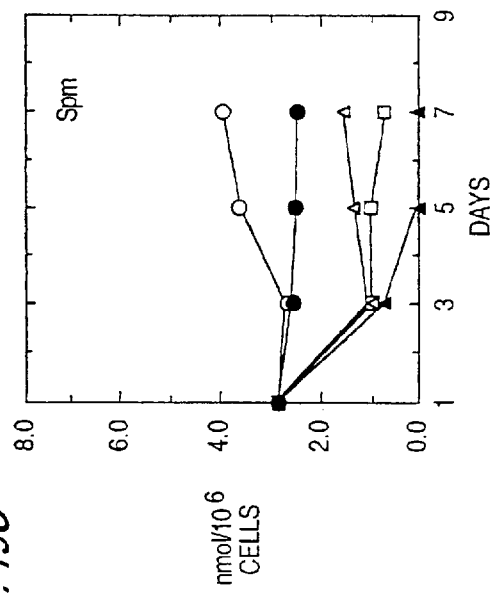
Figure 20B:
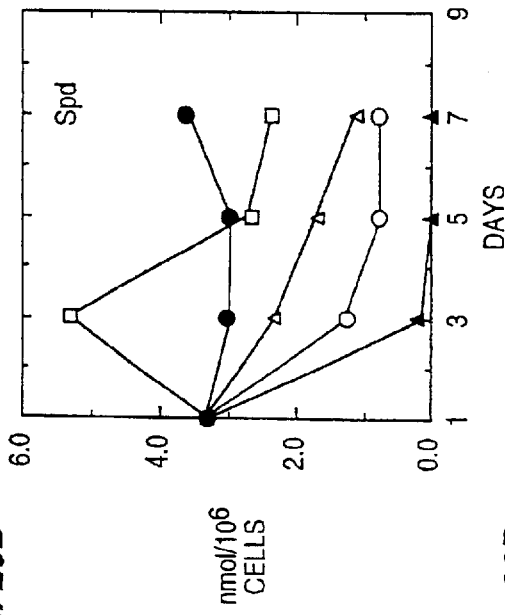
FIG. 20 depicts polyamine levels of SF-763 cells treated with 10 μM BE-4-4-4-4 and polyamines. Control (●), BE-4-4-4-4 (▲), BE-4-4-4-4+1 mM putrescine (Δ), BE-4-4-4-4+20 μM spermidine (□), BE-4-4-4-4+20 μM spermine (○). Values are based on an average of two determinations. Polyamines were added simultaneously with BE-4-4-4-4.
Figure 20D:
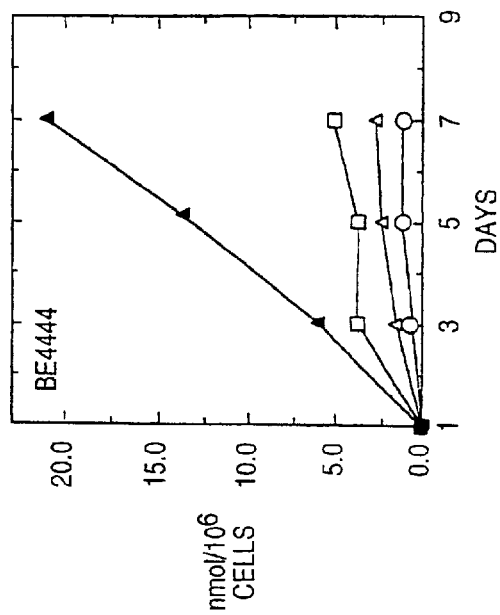
Figure 20A:
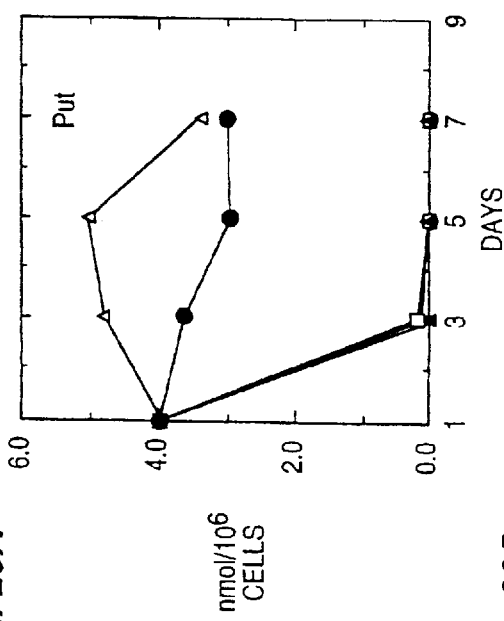
Figure 20C:
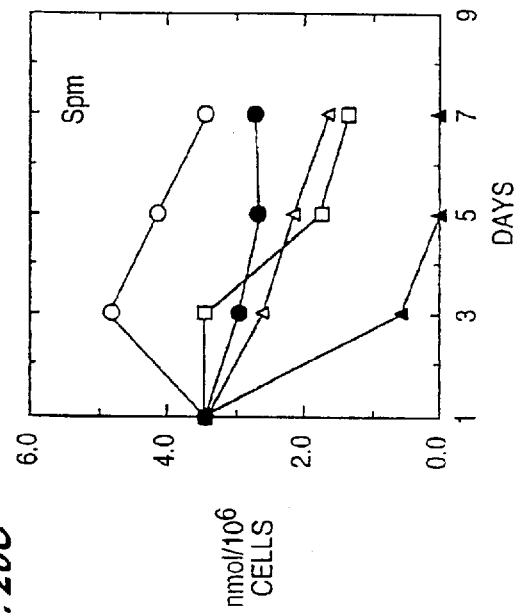
Figure 21B:
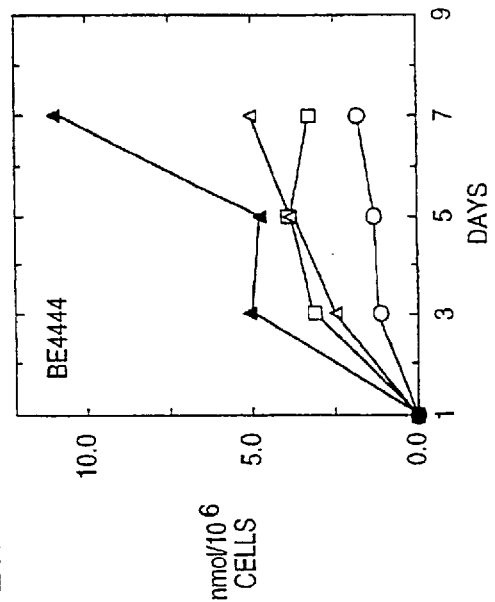
FIG. 21 depicts polyamine levels of U-251 cells treated with 10 μM BE-4-4-4-4 and polyamines. Symbols and explanation set forth for FIG. 19 also pertain to this figure.
Figure 21D:
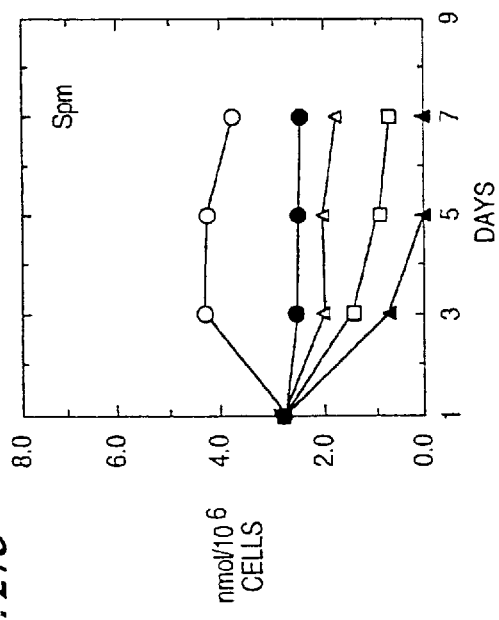
Figure 21A:
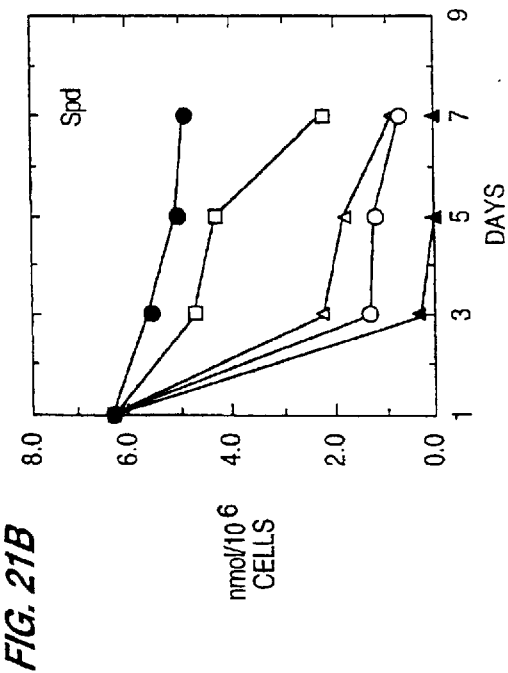
Figure 21C:
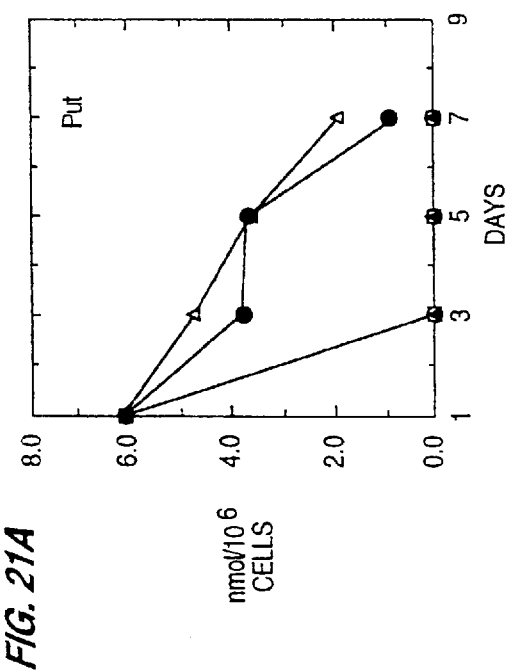

Body weight was affected by BE-4-4-4-4 treatment in mice paired by tumor size (FIG. 33). Five of the 10 pairs lost more than 10% of their body weight (note, for example, pairs 2 and 7). The other pairs showed little evidence of weight loss. A special wet biscuit and apple chip diet enabled four of the five pairs that lost weight to survive. One pair was excluded from analysis because the treated animal died before it could be placed on the special diet. There was no correlation between loss of weight and tumor volume (FIG. 34).

The above experiments establish conditions for treating human tumor xenografts in nude mice with BE-4-4-4-4. A single cycle of BE-4-4-4-4 given to nude mice at 6 mg/kg b.i.d. in a 4/3/4 schedule allowed tumor-free nude mice to maintain a stable weight, delayed the growth of U-251 MG tumor xenografts in nude mice, and only produced a variable weight loss in nude mice bearing U-251 MG tumors.

EXAMPLE 5 EFFECT OF BE-4-4-4-4 ON VARIOUS TUMORS

Mice were injected with tumor cells from 1 of 5 human tumor cell lines: glioblastoma (SF-767, $2.5 \times 10^6$, or U-87 MG, $7.9 \times 10^6$); lung adenocarcinoma (A549, $2.7 \times 10^6$); colon carcinoma (HCT116, $10 \times 10^6$, or HT29, $10.2 \times 10^6$). Body weight and tumor size were monitored 2 times per week until the tumor reached a volume greater than 2000 $mm^3$, a criterion for euthanasia. Two perpendicular tumor diameters, width (the smallest dimension) and length (the largest dimension) were measured with calipers. Tumor growth data are expressed as tumor volumes ($mm^3$) calculated from the following equation: length×width$^2$×0.52. The doubling time from 500 $mm^3$ to 1000 $mm^3$ was 11 days for the SF-767 tumor, 3 days for the U-87 MG tumor, 26 days for the A549 tumor, 12 days for the HCT116 tumor, and 9 days for the HT29 tumor.

Treatment began 8 days (for Ht29), 14 days (for SF-767), 16 days (for U-87 MG), 17 days (for HCT116), and 32 days (for A549) after mice received injections. At these times, the tumors reached average volumes of 127, 67, 53, 11, and 74 $mm^3$, respectively.

The effect of BE-4-4-4-4 was evaluated in all 5 tumor xenografts. BE-4-4-4-4 with a 0.5 mg/ml saline vehicle (0.9% NaCl, pH adjusted to 7.4 with 100 mM NaHCO$_3$), was administered i.p. in a dose of 5 mg/kg (0.2 ml/20 g mouse) twice daily in the 4/3/4 schedule (cycle 1). On day 42, mice initially treated with BE-4-4-4-4 were split into a control group and a group that was retreated on days 42 to 49 (cycle 2). Mice with U-87 MG, HT29, or HCT116 tumors received only 1 cycle of BE-4-4-4-4.

Combination Therapies

A 1,3-bis(2-chloroethyl)-1-nitrosourea ("BCNU") solution was prepared in 10% ethanol/saline immediately before injection and was administered i.p. in a dose of 50 mg/kg (5 mg/ml solution) for mice receiving BCNU alone, and 40 mg/kg (4 mg/ml) for mice receiving BE-4-4-4-4 with BCNU on day 4 (cycle 1) and day 46 (cycle 2). These were the maximum tolerated doses of BCNU.

Mice with SF-767 and HCT116 tumors were randomized to receive vehicle alone (same schedule as BE-4-4-4-4) or BE-4-4-4-4 alone. Mice with A549, HT29, or U-87 MG tumors were randomized to receive vehicle alone, BE-4-4-4-4 alone, BCNU alone, or BE-4-4-4-4 and BCNU in combination. Tumor regression was defined as 3 consecutive measurements, each of which was less than the previous one. Complete regression was defined as no visible tumor. The number of tumor regressions for each tumor xenograft is listed in FIG. 35.

SF-767 and U-87 MG Gliomas

Figure 36A:
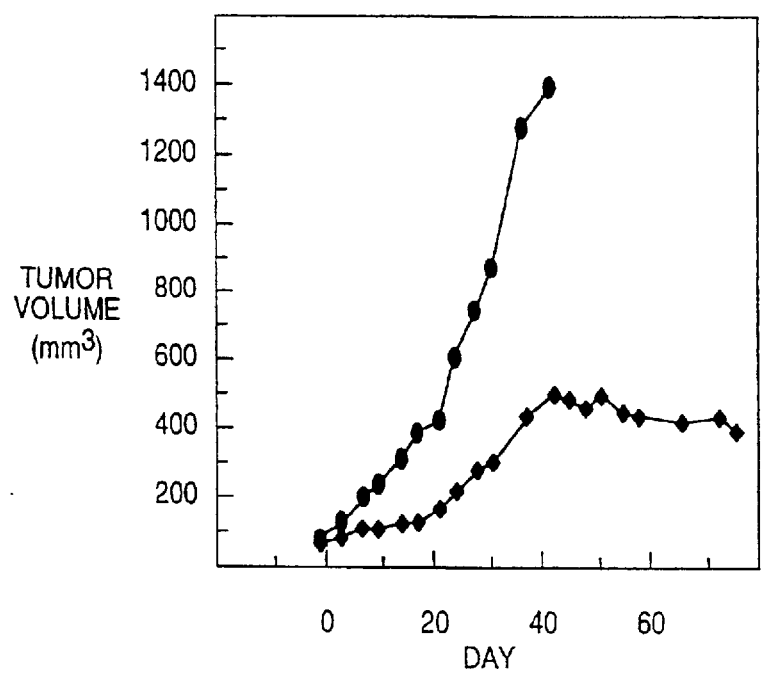
FIG. 36 depicts the growth rate of SF-767 xenografts treated with BE-4-4-4-4. Nude mice carrying SF-767 tumors were administered i.p. injections of saline (●)or 5 mg/kg b.i.d. of BE-4-4-4-4 on the 4/3/4 schedule for 2 cycles (♦). Graph A depicts tumor volume and graph B depicts body weights for each group. Data points represent the mean tumor volume and body weight for 8–9 mice per group.
Figure 36B:
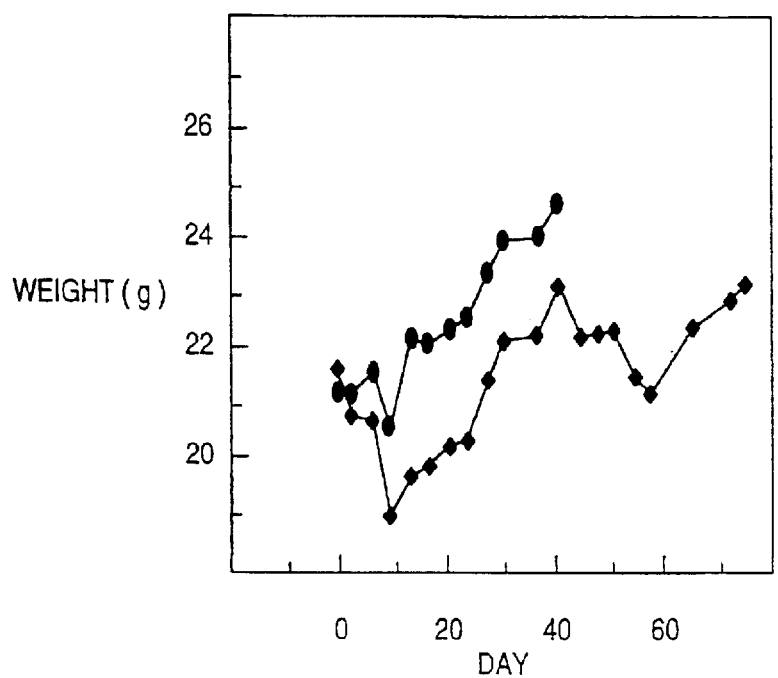
Figure 37:
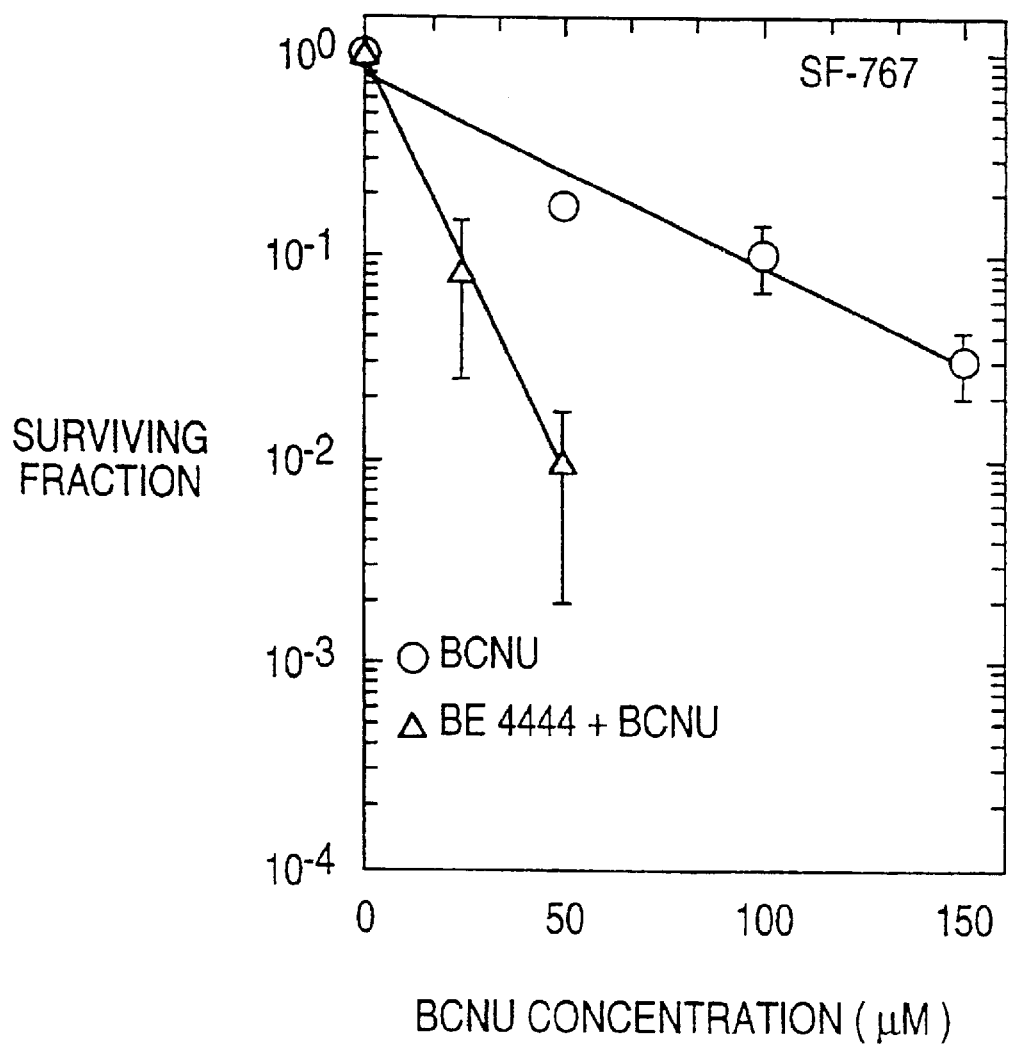
FIG. 37 depicts the effect of combined BE-4-4-4-4/BCNU as compared to BCNU alone on SF-767 cells.
Figure 39B:
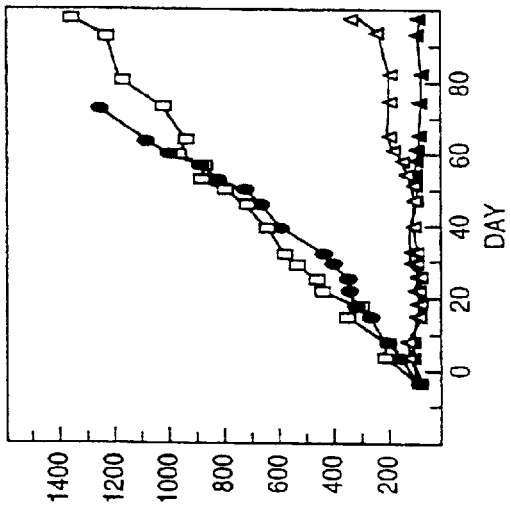
FIG. 39 depicts the growth rate of A549 xenografts treated with BE-4-4-4-4±BCNU. Graphs A and C concern nude mice carrying A549 tumors which were administered i.p. injections of saline (●) or 5 mg/kg b.i.d. of BE-4-4-4-4 on the 4/3/4 schedule for 1 cycle (◊) or 2 cycles (♦). Graphs B and D concern mice treated with 50 mg/kg BCNU alone (□) or BE-4-4-4-4 (same treatment schedule) with BCNU 40 mg/kg for 1 cycle (Δ) or 2 cycles (▲). Graphs A and B depict tumor volume for each group, and graphs C and D depict body weights for each group. Data points represent the mean tumor volume and body weight for 3–7 mice per group.
Figure 39A:
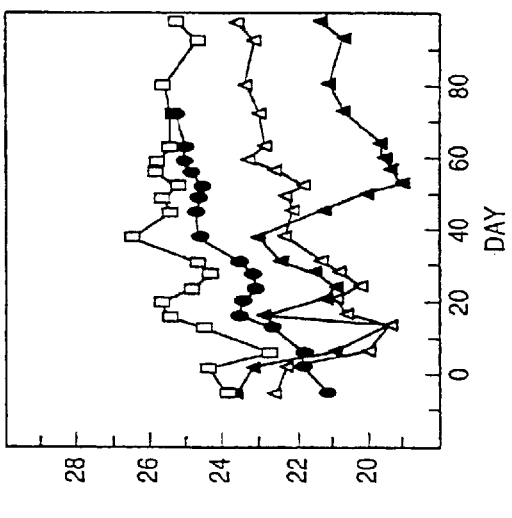
Figure 39D:
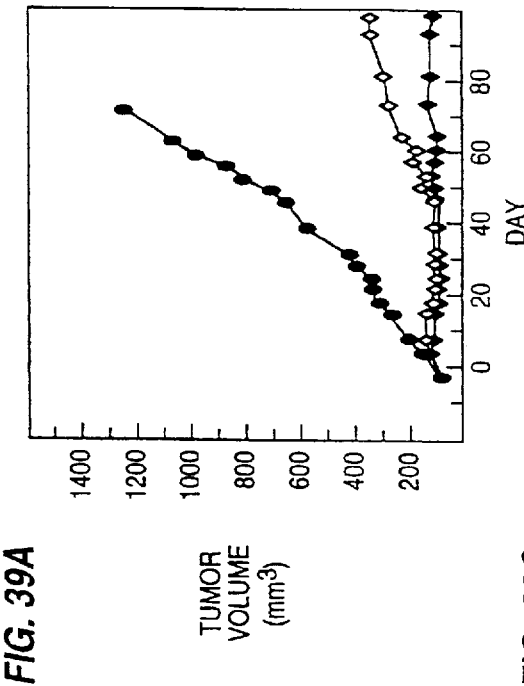
Figure 39C:
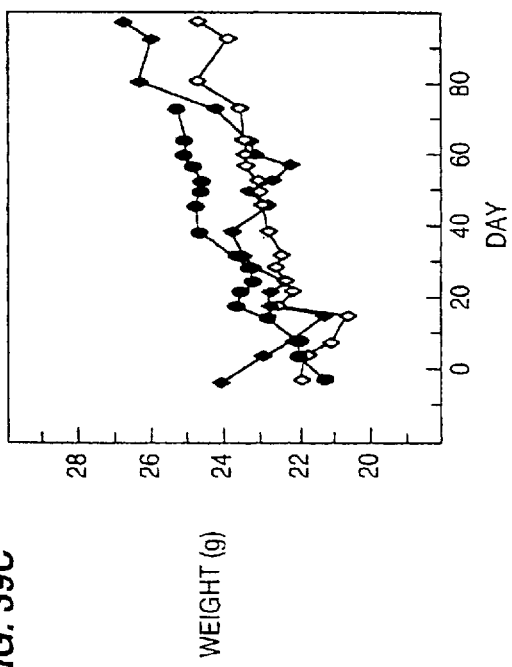

BE-4-4-4-4 was very effective in the SF-767 tumors (FIG. 36 at A). It produced 8/8 tumor regressions after 1 cycle, and 8/8 regressions and 3/8 complete regressions (cures) after 2 cycles (FIG. 35). The greatest weight loss (12% of total body weight) was observed at day 10. However, mice recovered after the drug was discontinued and did not display any overt toxic reactions (FIG. 36 at B). FIG. 37 compares BE-4-4-4-4/BCNU to BCNU alone in SF-767 cells. The curve is normalized for BE-4-4-4-4 alone.

The U-87 MG tumors were not as responsive as the SF-767 tumors to BE-4-4-4-4 alone. The number of tumor regressions was greater for control mice (1/9 versus 0/10 of treated mice (FIG. 35). The tumor growth rate was slightly less in treated mice than in controls (FIG. 38 at A). BCNU had a dramatic effect, resulting in 8/10 regressions. However, the combination of BE-4-4-4-4 and BCNU (8/9 regressions) was not much different than BCNU alone (FIG. 38 at B). Weight loss was much greater for the combination of BE-4-4-4-4 and BCNU than for either treatment alone (FIG. 38 at C and D).

A549 Lung Carcinoma

BE-4-4-4-4 was very effective on A549 tumors. It inhibited tumor growth for up to 98 days after treatment (FIG. 39 at A). A slight (6%) weight loss was observed at 15 days for mice treated with 1 cycle, and a second weight loss was observed at 57 days for those treated with 2 cycles (FIG. 39 at C). After 1 cycle of BE-4-4-4-4, 7/7 mice had tumor regressions; after 2 cycles, 3/3 mice had regressions (FIG. 35). The average tumor size at day 98 was markedly larger in mice that received only 1 cycle of BE-4-4-4-4 than those receiving 2 cycles (347 mm$^3$ versus 107 mm$^3$; FIG. 39 at A). The maximum tolerated dose of BCNU produced little response in A549 tumors (FIG. 39 at B). The combination of BE-4-4-4-4 with 40 mg/kg BCNU produced a significantly better response than BCNU alone, but was not better than BE-4-4-4-4 alone. More weight loss (20%) occurred after 2 cycles of the combined treatment (FIG. 39 at D), but there were no additional tumor regressions (FIG. 39 at B).

HCT116 and HT29 Colon Carcinomas

Figure 40A:
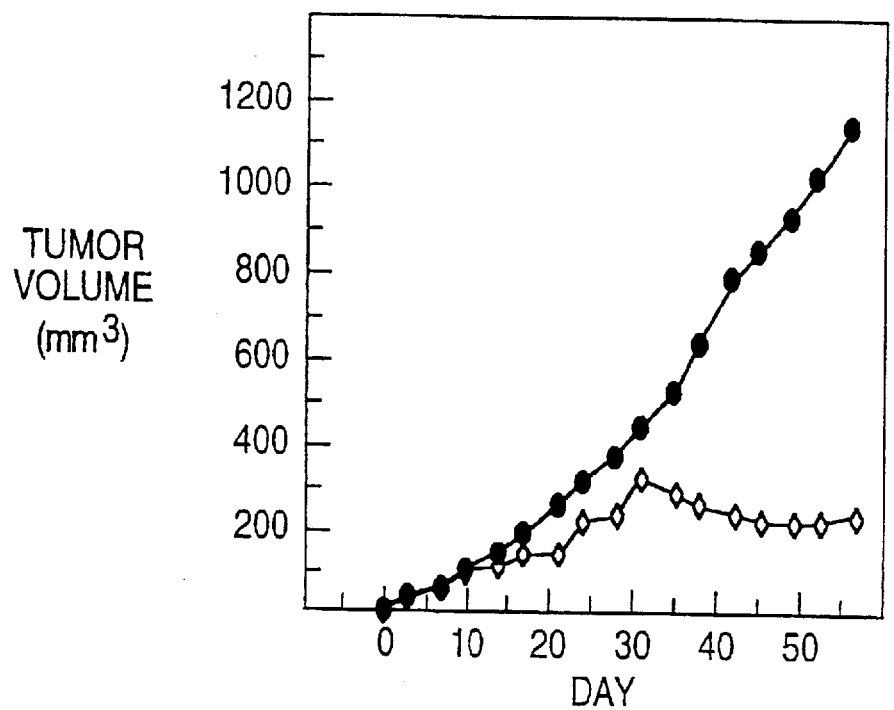
FIG. 40 depicts the growth of HCT116 xenograft treated with BE-4-4-4-4. Nude mice carrying HCT116 xenograft tumors were administered i.p. injections of saline (●) or 5 mg/kg b.i.d. of BE-4-4-4-4 on the 4/3/4 schedule for 1 cycle (◊). Graph A depicts tumor volume and graph B depicts body weights for each group. Data points represent the mean tumor volume and body weight for 4 mice per group.
Figure 40B:
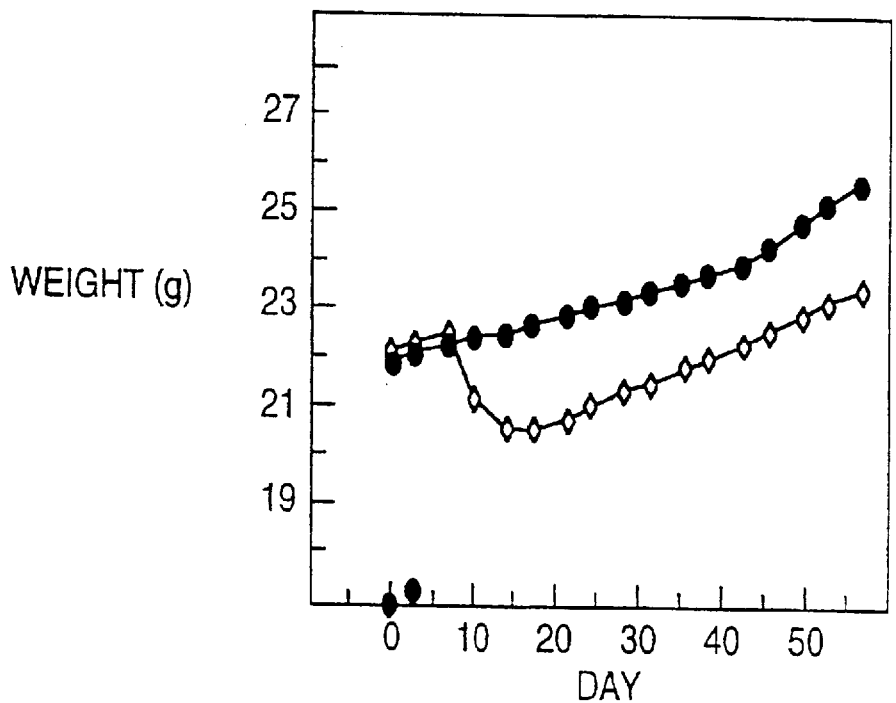
Figure 41B:
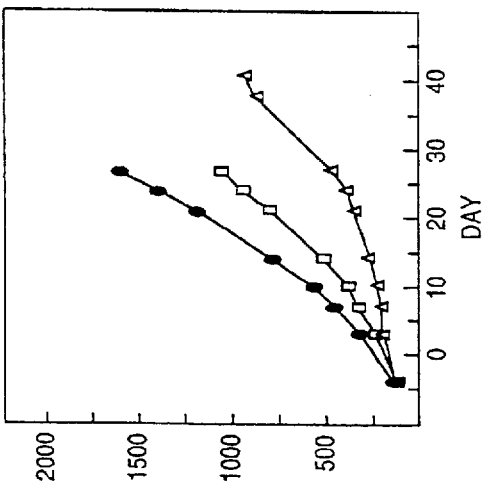
FIG. 41 depicts the growth rate of HT29 xenografts treated with BE-4-4-4-4±BCNU. Graphs A and C concern nude mice carrying HT29 tumors which were administered i.p. injections of saline (●) or 5 mg/kg b.i.d. of BE-4-4-4-4 on the 4/3/4 schedule for 1 cycle (◊). Graphs B and D concern mice treated with 50 mg/kg BCNU alone (□) or BE-4-4-4-4 (same treatment schedule) with BCNU 40 mg/kg for 1 cycle (Δ). Graphs A and B depict tumor volume for each group, and graphs C and D depict body weights for each group. Data points represent the mean tumor volume and body weight for 6–8 mice per group.
Figure 41D:
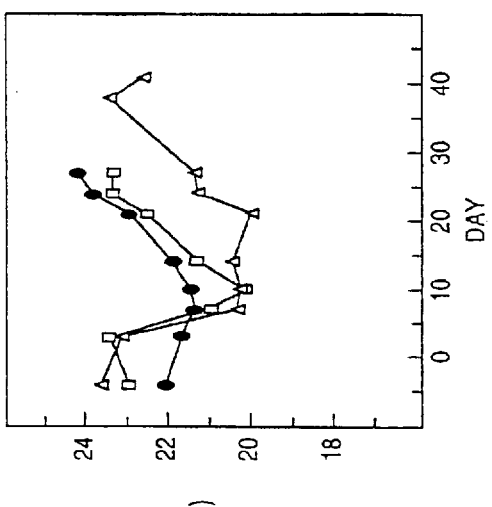
Figure 41A:
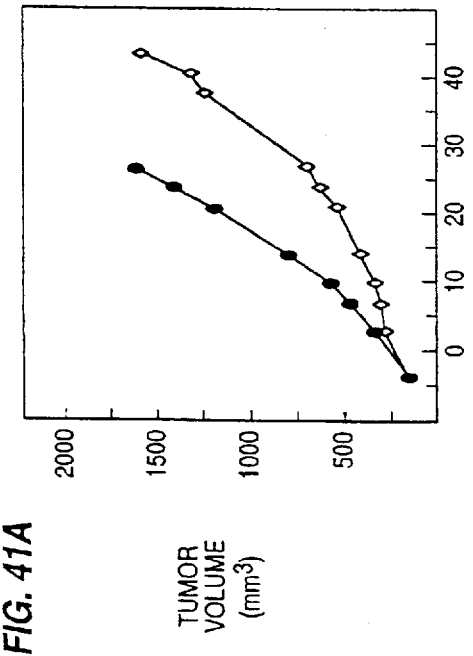
Figure 41C:
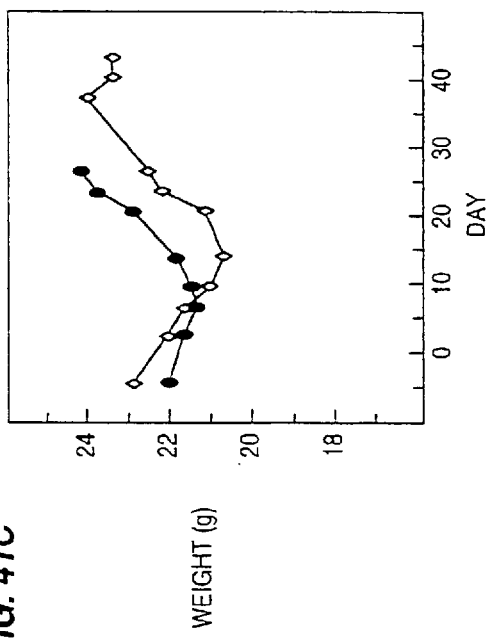

The HCT116 tumors responded well to BE-4-4-4-4 (FIG. 40, top graph). 4/4 mice had tumor regressions after 1 cycle. Growth inhibition was evident at 10–14 days and was maintained until day 56. The greatest weight loss (6–9%) occurred between days 10 and 17; weight gain resumed by days 21–24 (FIG. 40, bottom graph).

The HT29 tumors did not respond as well to BE-4-4-4-4. There were 0/8 regressions after 1 cycle (FIG. 41 at A). No growth delay was observed with BCNU alone, but the combination of BCNU and BE-4-4-4-4 produced a 16-day growth delay (FIG. 41 at B), and resulted in 2/8 regressions, compared with 0/8 for BE-4-4-4-4 alone, and 0/6 for BCNU alone. Again, all mice except controls had a transient weight loss of about 10% (FIG. 41 at C and D).

Figure 42A:
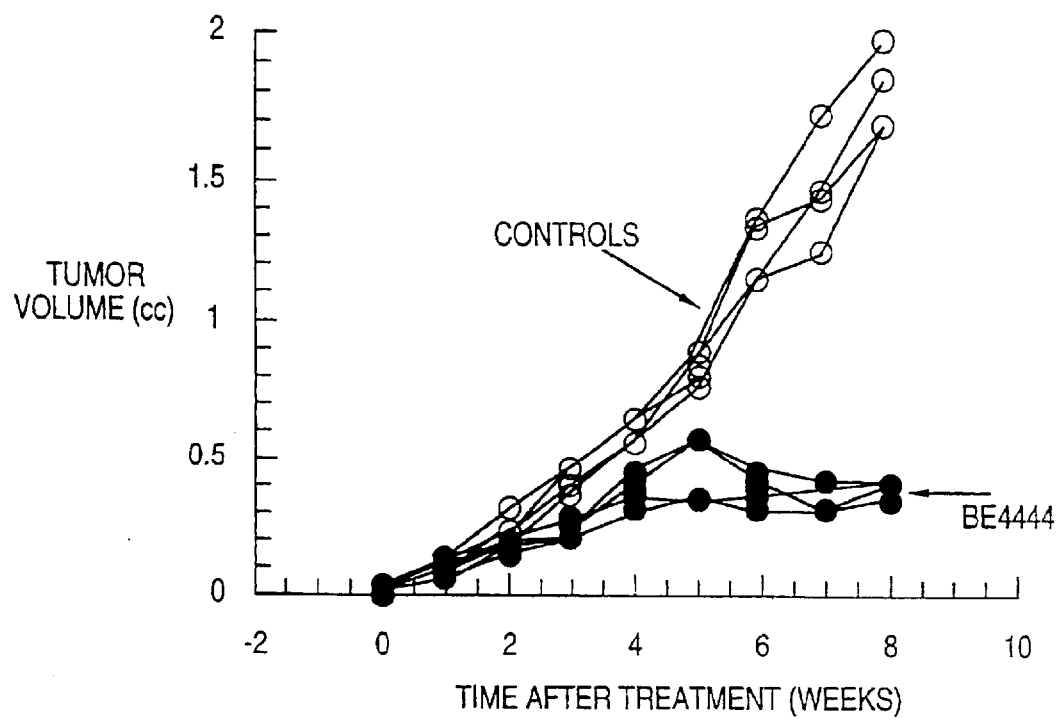
FIG. 42 depicts the inhibitory effects of BE-4-4-4-4 therapy xenografts of HCT116 cells, a human colon cancer cell line (top graph). The bottom graph shows the average effects of these therapies on tumor volume.
Figure 42B:
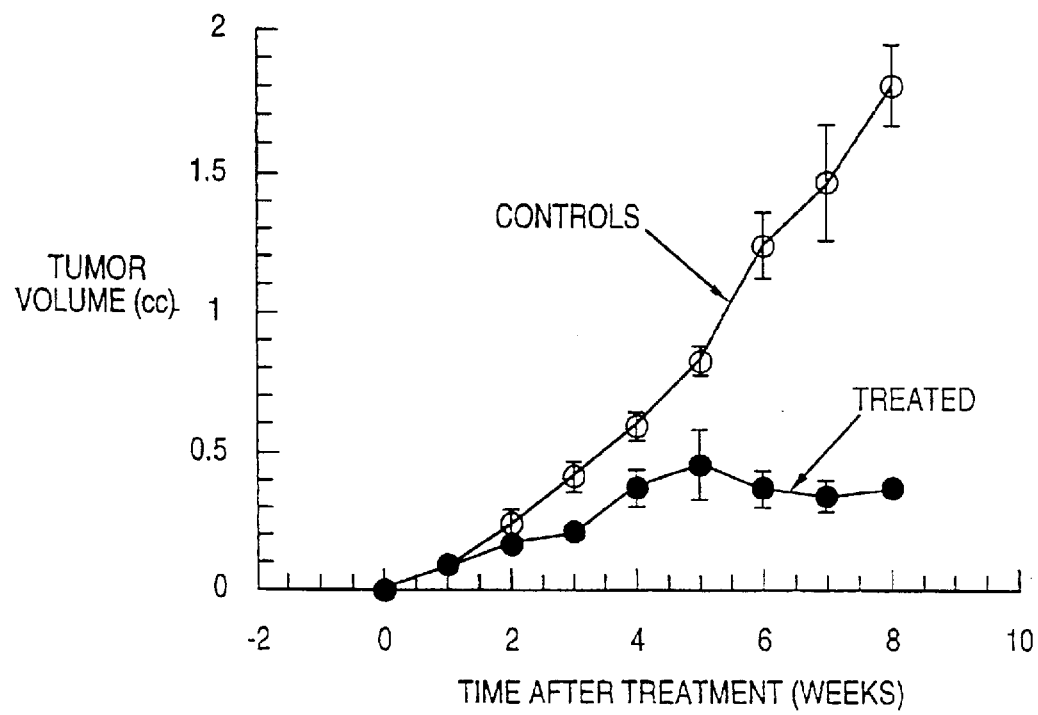

FIG. 42 depicts the effects of BE-4-4-4-4, BCNU and combined BE-4-4-4-4 and BCNU therapy on HCT116 cells. The data depicted in FIG. 42 show that BE-4-4-4-4 alone and in combination with BCNU had a dramatic inhibitory effect on the tumors (top graphs), yet weight variations were kept to a minimum (bottom graphs).

Figure 43:
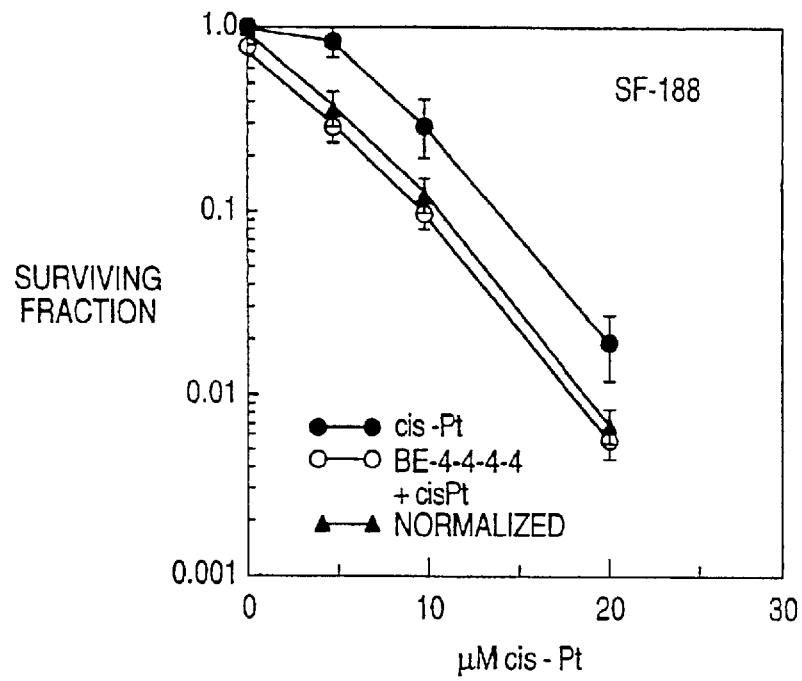
FIG. 43 depicts the effect of combined BE-4-4-4-4/cis-Pt as compared to cis-Pt alone in SF-188 cells in culture.

A combined therapy study was also undertaken with BE-4-4-4-4 and cis-Pt. As was the case with BCNU, BE-4-4-4-4 potentiates the action of cis-Pt. See FIG. 43.

Figure 44:
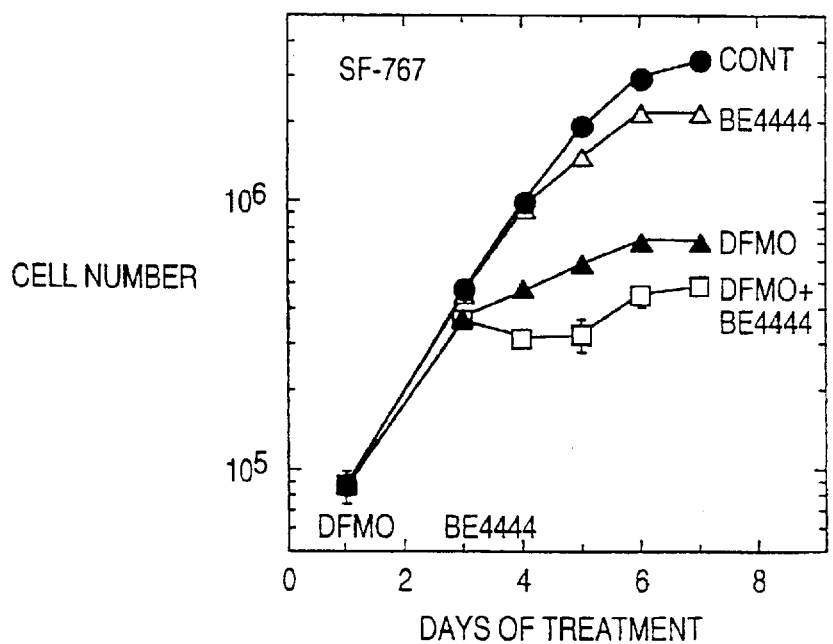
FIG. 44 depicts data from a reversal study of DFMO by BE-4-4-4-4.

FIG. 44 depicts results from a study to determine whether BE-4-4-4-4 can reverse the effects of DFMO. Because BE-4-4-4-4 is an analog of spermine, the possibility that it could be behave like spermine in the context of DFMO activity was investigated. The data of FIG. 44 shows that BE-4-4-4-4 does not reverse or prevent the inhibitory effects of DFMO.

Histopathological Evaluation

On day 99, mice with A549 tumors were sacrificed and tumors were cut into 2–11 pieces. Twelve to 18 sections of each were made for histopathological examination. The number of mitoses were counted in 10 high-power fields per slide.

Histopathological examination of representative tumors from A549 control and treated mice showed that the mitotic indices were 18-times lower in the treated group than in the control group (FIG. 45). Control tumors had a much higher incidence of polymorphous nuclei, such as multioblate, cleaved, doughnut, and horseshoe-shaped. More lymphocytes with plasma cells and Mott cells were found in mice treated with the combination of BE-4-4-4-4 and BCNU for 1 or 2 cycles than in controls or mice receiving 1 or 2 cycles of BE-4-4-4-4 alone (data not shown).

Activity of Spermidine/spermine-N1-acetyltransferase

The activity of Spermidine/spermine-N1-acetyltransferase ("SSAT") was measured according to reported procedures. Casero et al., Cancer Res. 49: 3829–33 (1989). First, approximately 2×10$^6$ cells were seeded in T-175 flasks in 35 ml MEM with 10% FCS. BE-4-4-4-4 was added 1 day after cell seeding. Twenty-four hours after analog treatment, cells were harvested by scraping, washed once in phosphate-buffered saline and suspended at a concentration of approximately 2×10$^7$ cells/ml in 5 mM HEPES and 1 mM dithiothreitol, pH 7.2. This suspension was homogenized by brief sonication and centrifuged in a refrigerated minifuge at 12,000×g for 30 minutes. The resulting supernatant was used as a source of SSAT. Aliquots of this cytosol were incubated in 100 mM HEPES, pH 7.8, 0.15 nmol spermidine, and 0.05 nmol 1-[$^{14}$C]acetyl CoA in a final volume of 50 μl for 5 min at 37° C. The reaction was stopped by the addition of 20 μl 0.5M NH$_2$OH—HCl and then heated in a boiling water bath for 3 min. The resulting samples were centrifuged, aliquots were spotted onto P-81 phosphocellulose discs, and radioactivity was quantitated by scintillation counting. The amount of cytosol added to the final reaction mixture was adjusted to maintain the enzyme/substrate concentrations in the linear range. Each enzyme determination was-performed on replicates, each of which contained cytosolic extracts from $2\times10^6$ viable cells. Enzyme activity was expressed as pmol/[$^{14}$C]acetylspermidine formed/minute/mg protein. Protein was quantitated using the methods of Bradford, *Analyt. Chem.* 72: 248–54 (1976).

SSAT activity in SF-767 and U-251 MG cells treated with 10 μm BE-4-4-4-4 for 24 hrs is shown in FIG. 46. No significant difference in SSAT activity was found between treated and untreated cells. This differs from mechanisms implicated for other growth inhibitory polyamine analogs, such as BE-4-4-4. BE-4-4-4 has been shown to greatly increase levels of SSAT, which decrease cellular levels of the natural polyamines. In this respect, BE-4-4-4 functions much like the polyamine inhibitors.

The above in vitro and in vivo data demonstrate that BE-4-4-4-4 has antitumor effects against cellular abnormalities such as human glioma, lung, and colon tumor xenografts. The benefit of 1 or 2 cycles of treatment was especially dramatic in SF-767 glioma and A549 lung tumor xenografts. The growth rate of SF-767 tumors slowed after a second cycle, indicating that tumors treated with 1 cycle of BE-4-4-4-4 were not resistant to a second.

An impressive response was also observed for the HCT116 tumors. HT29 and U-87 MG tumors were the least responsive to BE-4-4-4-4, although growth inhibition was observed in both.

The growth inhibitory effects of BCNU alone and in combination with BE-4-4-4-4 were compared to effects of BE-4-4-4-4 alone in mice with A549, HT29, and U-87 MG tumors. BCNU inhibited the growth of the U-87 MG tumors. The addition of BE-4-4-4-4 increased its efficacy only slightly. In contrast, the A549 tumors were extremely responsive to BE-4-4-4-4, and the addition of BCNU did not further delay growth. The HT29 tumors were resistant to BCNU alone and were somewhat responsive to BE-4-4-4-4, but benefitted from the combination (2/8 mice had tumor regressions).

These results show that in tumors that do not respond well to BE-4-4-4-4 or BCNU alone, the combination may be useful.

The 2 brain tumors SF-767 and U-87 MG responded very differently to treatment with BE-4-4-4-4 alone. Almost complete regressions were observed in most mice with SF-767 tumors, but those with U-87 MG tumors responded poorly and would be considered resistant to BE-4-4-4-4.

BE-4-4-4-4 proved to be efficacious against human brain, colon, and lung tumors, which usually are extremely challenging tumors to treat.

EXAMPLE 6 TREATING PATIENTS WITH BE-4-4-4-4

Preparation of BE-4-4-4-4 solutions

BE-4-4-4-4 is highly soluble in water and, therefore, is amenable to many well-known pharmaceutically acceptable carriers or vehicles. For instance, a 0.5 mg/ml saline vehicle (0.9% NaCl, pH adjusted to 7.4 with 100 mM NaHCO$_3$) can be used for injections of BE-4-4-4-4. Other appropriate carriers include aqueous solutions, non-toxic excipients, including salts, preservatives, buffers and the like, as described in REMINGTON'S PHARMACEUTICAL SCIENCES, 15th Ed. Easton: Mack Publishing Co. pp 1405–1412 and 1461–1487 (1975) and THE NATIONAL FORMULARY XIV., 14th Ed. Washington: American Pharmaceutical Association (1975), the contents of which are hereby incorporated by reference. Aqueous carriers include water, alcoholic/aqueous solutions, saline solutions, parenteral vehicles such as sodium chloride and Ringer's dextrose. Intravenous vehicles include fluid and nutrient replenishers. Preservatives include antimicrobials, antioxidants, chelating agents and inert gases. The pH and exact concentration of the various components of the binding composition are adjusted according to routine skills in the art. See GOODMAN AND GILMAN'S THE PHARMACOLOGICAL BASIS FOR THERAPEUTICS (7th ed.). These carriers can be employed with other compounds of the present invention.

Therapy

Patients could be treated with therapeutically effective amounts of BE-4-4-4-4 in a variety of ways. Established administration routes can be employed with BE-4-4-4-4, such as intravenous, subcutaneous, intramuscular and oral. Dosages and administration routes and schedules depend on the condition of the patient, the type and size of tumor afflicting the patient, and the location of the tumor. A therapeutically effective amount of a compound refers to the amount needed to attain the antineoplastic effects of the compound being administered.

An acceptable dosage for therapy includes 5–6 mg BE-4-4-4-4/kg body weight b.i.d. Typically, seven to eight treatment cycles with 1 to 2 weeks between cycles is efficacious. As stated above, these dosages and cycles can be altered based on the clinical determinations, such as progress, patient condition, and size, type and distribution of tumors. A 4 days on, 3 days off, 4 days on (4/3/4) administration schedule is also appropriate. These considerations can be employed with other compounds of the present invention.

BE-4-4-4-4, as well as the other compounds of the present invention, can also be used in combination with other therapeutic agents, such as BCNU and cis-Pt. The combined administrations can be undertaken concurrently or sequentially. The dosages, administration routes and administration schedules for combination therapies can also be altered based on the clinical determinations described above.

What is claimed is:

1. A method of treating cancers sensitive to the combination below, comprising the steps of:

administering a therapeutically effective amount of a polyamine analog $N^1,N^{19}$-bis(ethylamino)-5,10,15-triazanonadecane; and administering an enhancing effective amount of at least one other antineoplastic therapeutic agent.

2. A method according to claim 1, wherein said administering steps are performed by injection.

3. A method according to claim 1, wherein said administering steps are performed orally.

4. The method of claim 1, wherein the other antineoplastic therapeutic agent is cis-diamminedichloroplatinum (II).

5. The method of claim 1, wherein the other antineoplastic therapeutic agent is 1,3-bis(2-chloroethyl)-1-nitrosourea.

6. The method of claim 1, wherein the $N^1$, $N^{19}$-bis(ethylamino)-5,10,15-triazanonadecane and the second antineoplastic agent are administered concurrently.

7. The method of claim 1, wherein the $N^1,N^{19}$-bis(ethylamino)-5,10,15-triazanonadecane and the second antineoplastic agent are administered sequentially.

8. A therapeutic composition comprising $N^1,N^{19}$-bis(ethylamino)-5,10,15-triazanonadecane and at least one other antineoplastic agent, in a therapeutically effective amount in which the other antineoplastic agent enhances an antineoplastic activity of the $N^1,N^{19}$-bis(ethylamino)-5,10,15-triazanonadecane.

9. The therapeutic composition according to claim 8, wherein said at least one other antineoplastic therapeutic agent is selected from the group consisting of 1,3-bis(2-chloroethyl)-1-nitrosourea and cis-diamminedichloroplatinum (II).

10. The therapeutic composition according to claim 8, wherein said at least one other antineoplastic therapeutic agent is 1,3-bis(2-chloroethyl)-1-nitrosourea.

11. The therapeutic composition according to claim 8, wherein said at least one other antineoplastic therapeutic agent is cis-diamminedichloroplatinum (II).

* * * * *

UNITED STATES PATENT AND TRADEMARK OFFICE
CERTIFICATE OF CORRECTION

PATENT NO. : 5,880,161
DATED : March 9, 1999
INVENTOR(S) : Hirak Subhra Basu, Burt Feuerstein, Keijiro Samejima, Laurence Marton It is certified that error appears in the above-identified patent and that said Letters Patent is hereby corrected as shown below:

<u>Specification,</u>
<u>Column 5,</u>
Line 17, change "IT" to -- T --.

Signed and Sealed this

Ninth Day of October, 2001

*Attest:*

NICHOLAS P. GODICI
*Attesting Officer*     *Acting Director of the United States Patent and Trademark Office*